(12) United States Patent
Seeley et al.

(10) Patent No.: US 10,549,088 B2
(45) Date of Patent: Feb. 4, 2020

(54) STRUCTURES AND TECHNIQUES FOR MEDICAL LEAD FABRICATION

(71) Applicant: Medtronic, Inc., Minneapolis, MN (US)

(72) Inventors: Dale F. Seeley, Spring Park, MN (US); Evan Mark Gustafson, Seattle, WA (US); Michael T. Hegland, Mounds View, MN (US); Seth M. Humphrys, Golden Valley, MN (US); Darren A. Janzig, Center City, MN (US); Gerald G. Lindner, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 14/396,326

(22) PCT Filed: Mar. 15, 2013

(86) PCT No.: PCT/US2013/032646
§ 371 (c)(1),
(2) Date: Oct. 22, 2014

(87) PCT Pub. No.: WO2013/162775
PCT Pub. Date: Oct. 31, 2013

(65) Prior Publication Data
US 2015/0080995 A1    Mar. 19, 2015

Related U.S. Application Data

(60) Provisional application No. 61/639,518, filed on Apr. 27, 2012.

(51) Int. Cl.
*A61N 1/05* (2006.01)

(52) U.S. Cl.
CPC ........... *A61N 1/05* (2013.01); *Y10T 29/49174* (2015.01); *Y10T 29/49185* (2015.01)

(58) Field of Classification Search
CPC ....................................................... A61N 1/05
See application file for complete search history.

(56) References Cited

U.S. PATENT DOCUMENTS 4,961,434 A   10/1990  Stypulkowski
5,000,194 A    3/1991  van den Honert et al.
(Continued)

FOREIGN PATENT DOCUMENTS

| EP | 0832667 A2 | 4/1998 |
| WO | 02068042 A1 | 9/2002 |
| WO | 2006133445 A2 | 12/2006 |

OTHER PUBLICATIONS

International Preliminary Report on Patentability from International Patent Application No. PCT/US2013/032646, dated Nov. 6, 2014, 10 pp.

(Continued)

*Primary Examiner* — Carl H Layno
*Assistant Examiner* — Jennifer L Ghand
(74) *Attorney, Agent, or Firm* — Shumaker & Sieffert, P.A.

(57) ABSTRACT

A medical lead may be fabricated using an electrode fixture ((130A)-(130D)) configured to facilitate circumferential and axial alignment between electrodes of the lead. In one example, a method includes positioning an electrode fixture around at least one conductor of a plurality of conductors (122) for a medical lead, wherein the electrode fixture at least partially retains an electrode assembly. The method also includes electrically coupling a portion of the at least one conductor with at least a portion of the electrode assembly at an attachment area defined by the electrode (Continued)

assembly when the electrode assembly is at least partially retained by the electrode fixture.

20 Claims, 38 Drawing Sheets

(56) References Cited

U.S. PATENT DOCUMENTS

| | | | |
|---|---|---|---|
| 5,423,877 | A | 6/1995 | Mackey |
| 5,522,874 | A | 6/1996 | Gates |
| 5,649,970 | A | 7/1997 | Loeb et al. |
| 5,800,465 | A | 9/1998 | Thompson et al. |
| 5,843,148 | A | 12/1998 | Gijsbers et al. |
| 6,038,480 | A | 3/2000 | Hrdlicka et al. |
| 6,473,653 | B1 | 10/2002 | Schallhorn et al. |
| 6,493,590 | B1 | 12/2002 | Wessman et al. |
| 6,510,347 | B2 | 1/2003 | Borkan |
| 6,757,970 | B1 | 7/2004 | Kuzma et al. |
| 7,668,601 | B2 | 2/2010 | Hegland et al. |
| 7,761,985 | B2 | 7/2010 | Hegland et al. |
| 8,000,808 | B2 | 8/2011 | Hegland et al. |
| 2002/0183817 | A1 | 12/2002 | Van Venrooij et al. |
| 2003/0083724 | A1 | 5/2003 | Jog et al. |
| 2004/0098074 | A1 | 5/2004 | Erickson et al. |
| 2006/0168805 | A1 | 8/2006 | Hegland et al. |
| 2006/0173262 | A1* | 8/2006 | Hegland ............... A61B 5/0422 600/373 |
| 2008/0114230 | A1 | 5/2008 | Addis |
| 2009/0276021 | A1 | 11/2009 | Meadows et al. |
| 2010/0269337 | A1* | 10/2010 | Dye ..................... A61N 1/0534 29/874 |
| 2011/0005069 | A1 | 1/2011 | Pianca |
| 2011/0078900 | A1 | 4/2011 | Pianca et al. |
| 2011/0130803 | A1 | 6/2011 | McDonald |
| 2011/0130818 | A1* | 6/2011 | Chen .................... A61N 1/0534 607/116 |
| 2011/0245903 | A1 | 10/2011 | Schulte et al. |
| 2011/0313500 | A1 | 12/2011 | Barker et al. |
| 2012/0165911 | A1* | 6/2012 | Pianca ................. A61N 1/0551 607/115 |
| 2012/0203320 | A1* | 8/2012 | DiGiore ............... A61N 1/0534 607/148 |
| 2014/0180375 | A1* | 6/2014 | Pianca ................. A61N 1/0534 607/116 |

OTHER PUBLICATIONS

International Search Report and Written Opinion from International Patent Application No. PCT/US2013/032646, dated Mar. 12, 2014, 16 pp.

Examination Report from counterpart European Application No. 13716898.5, dated Mar. 6, 2018, 4 pp.

* cited by examiner

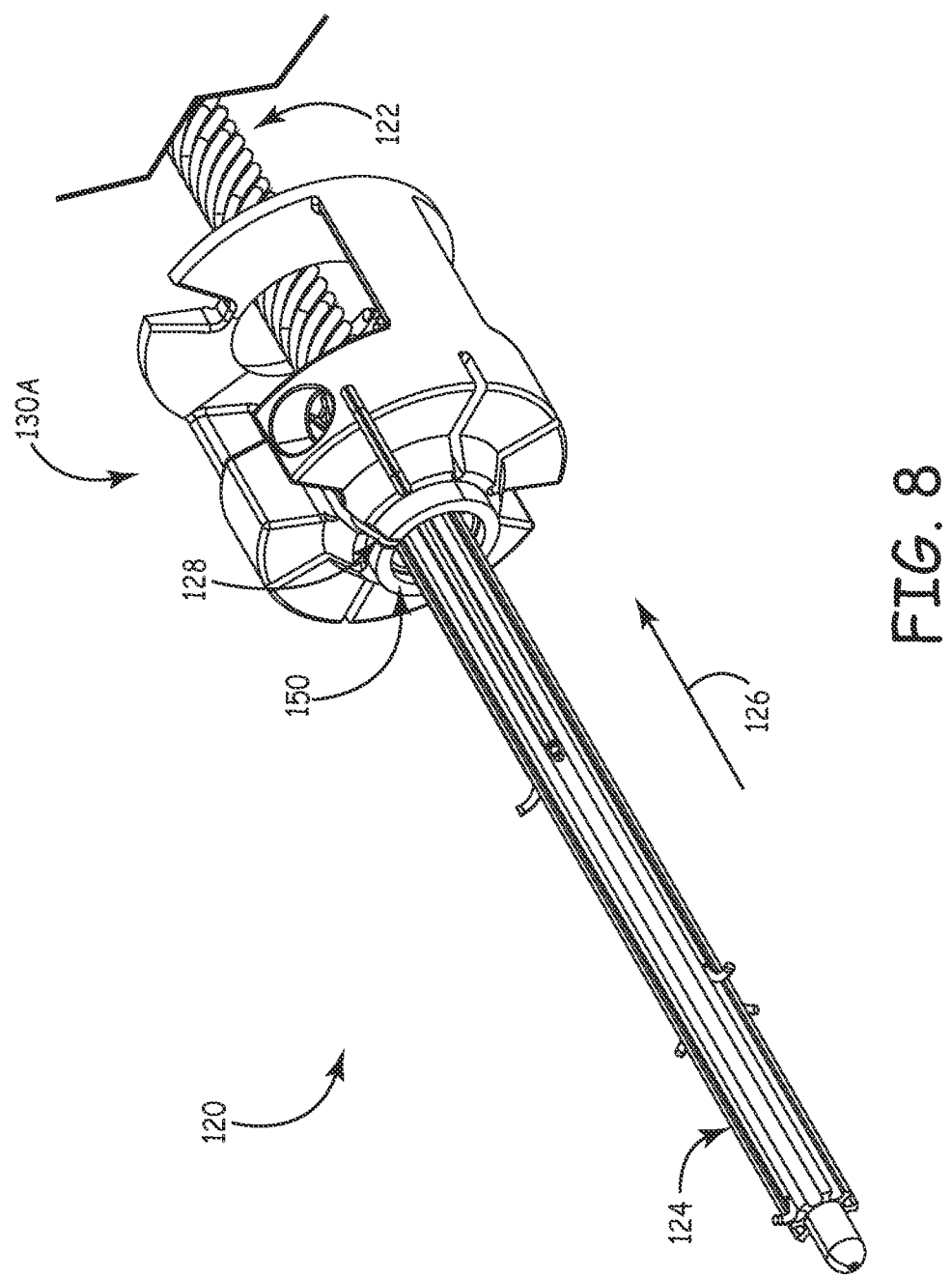

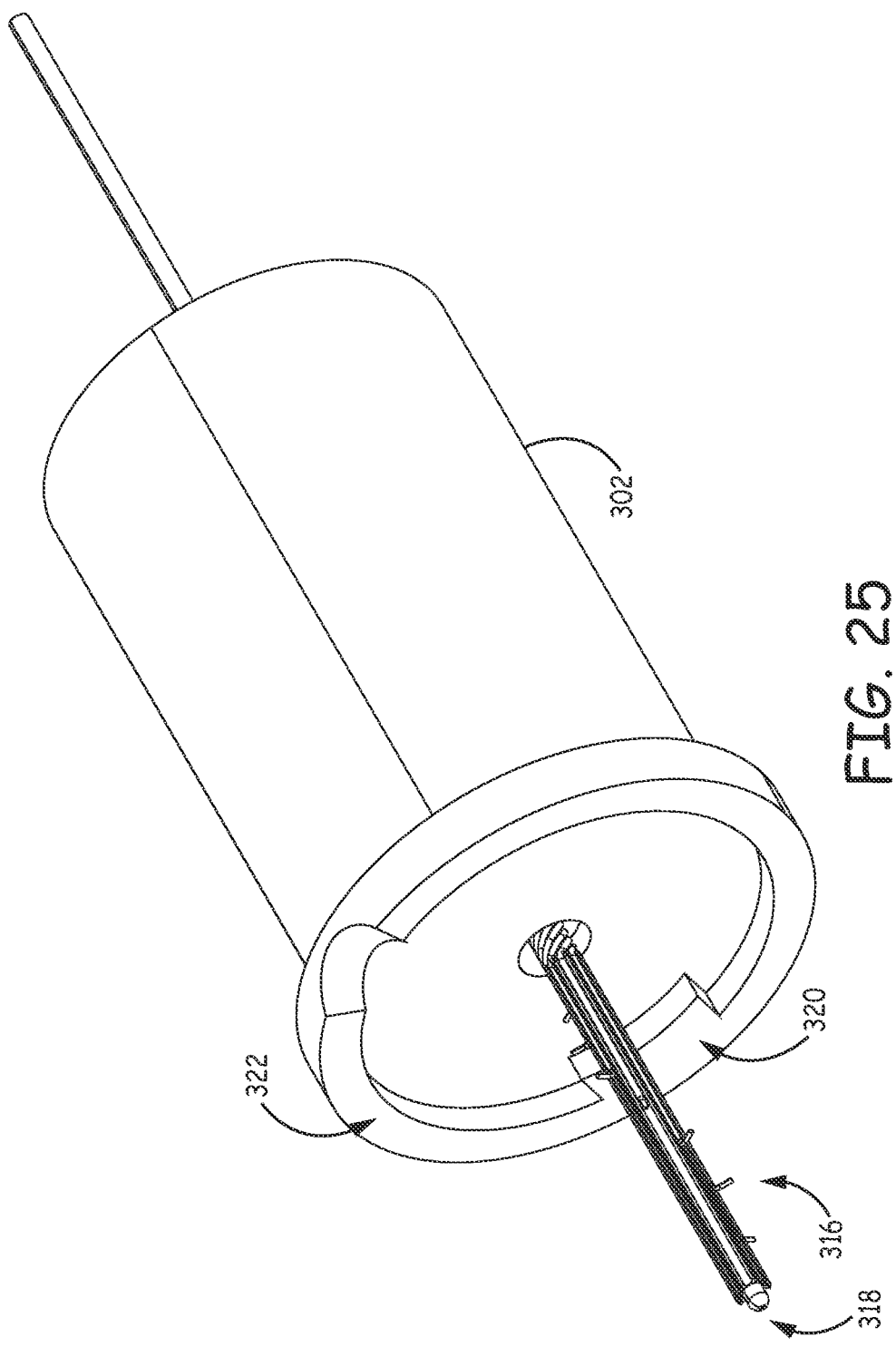

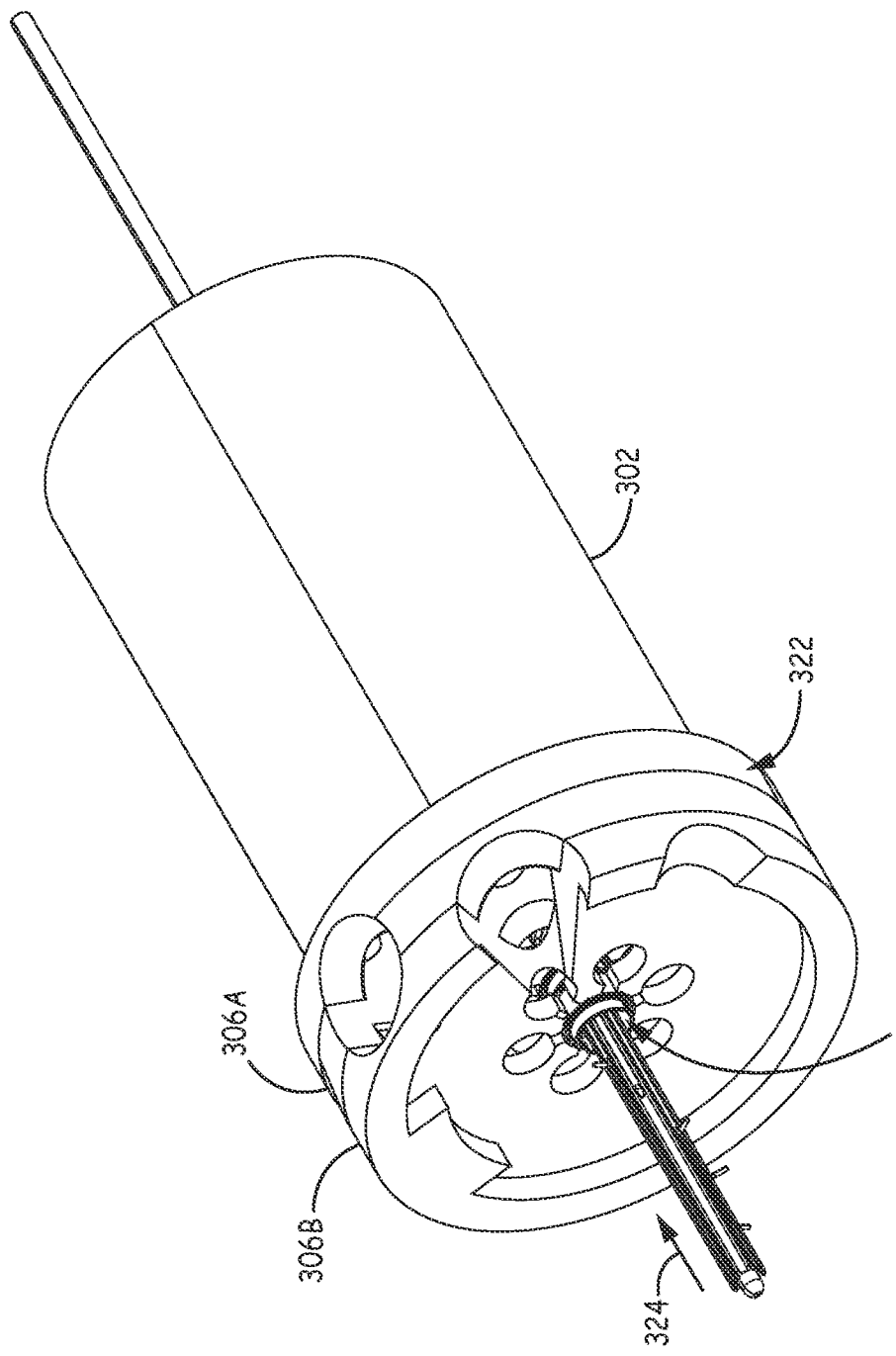

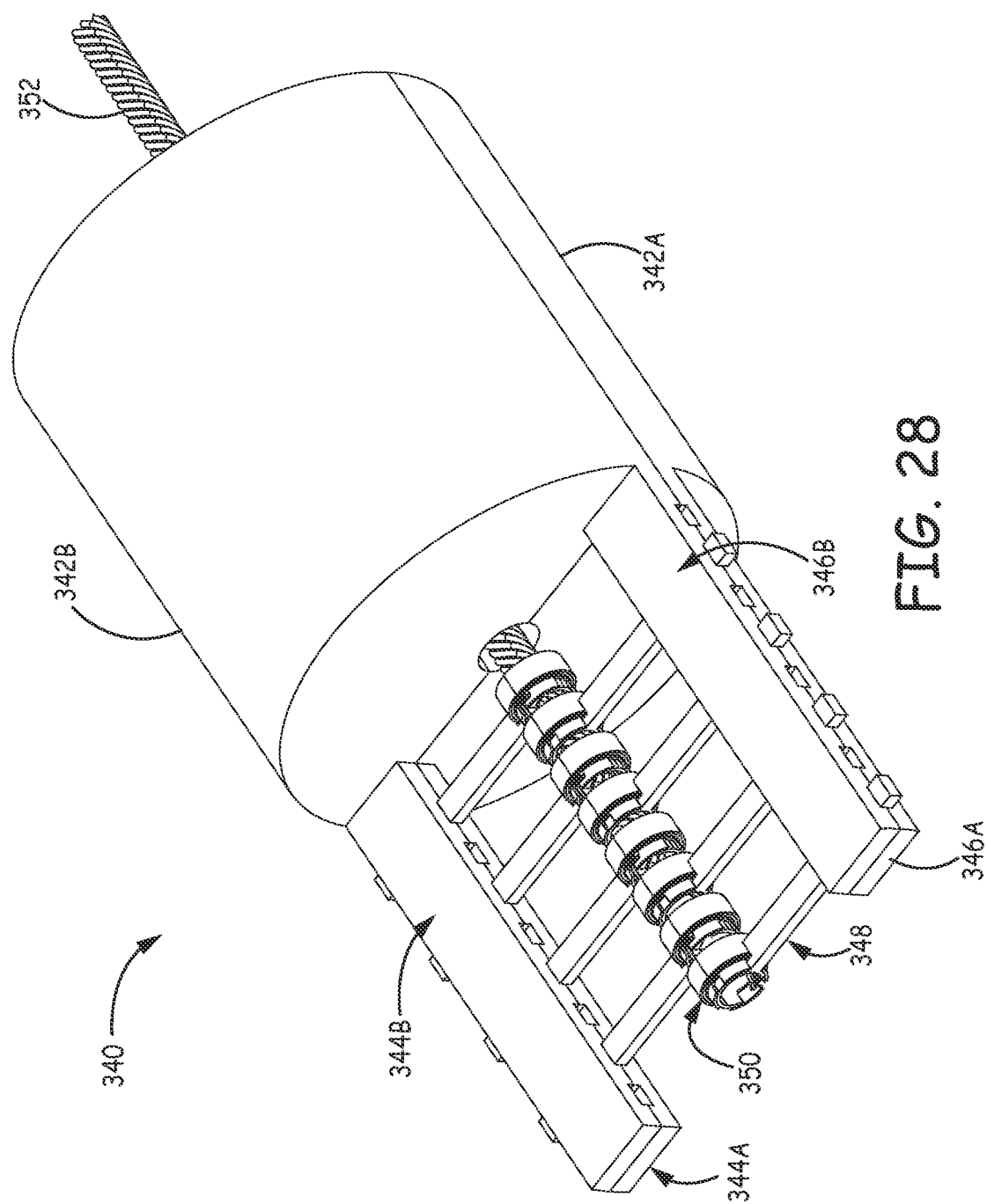

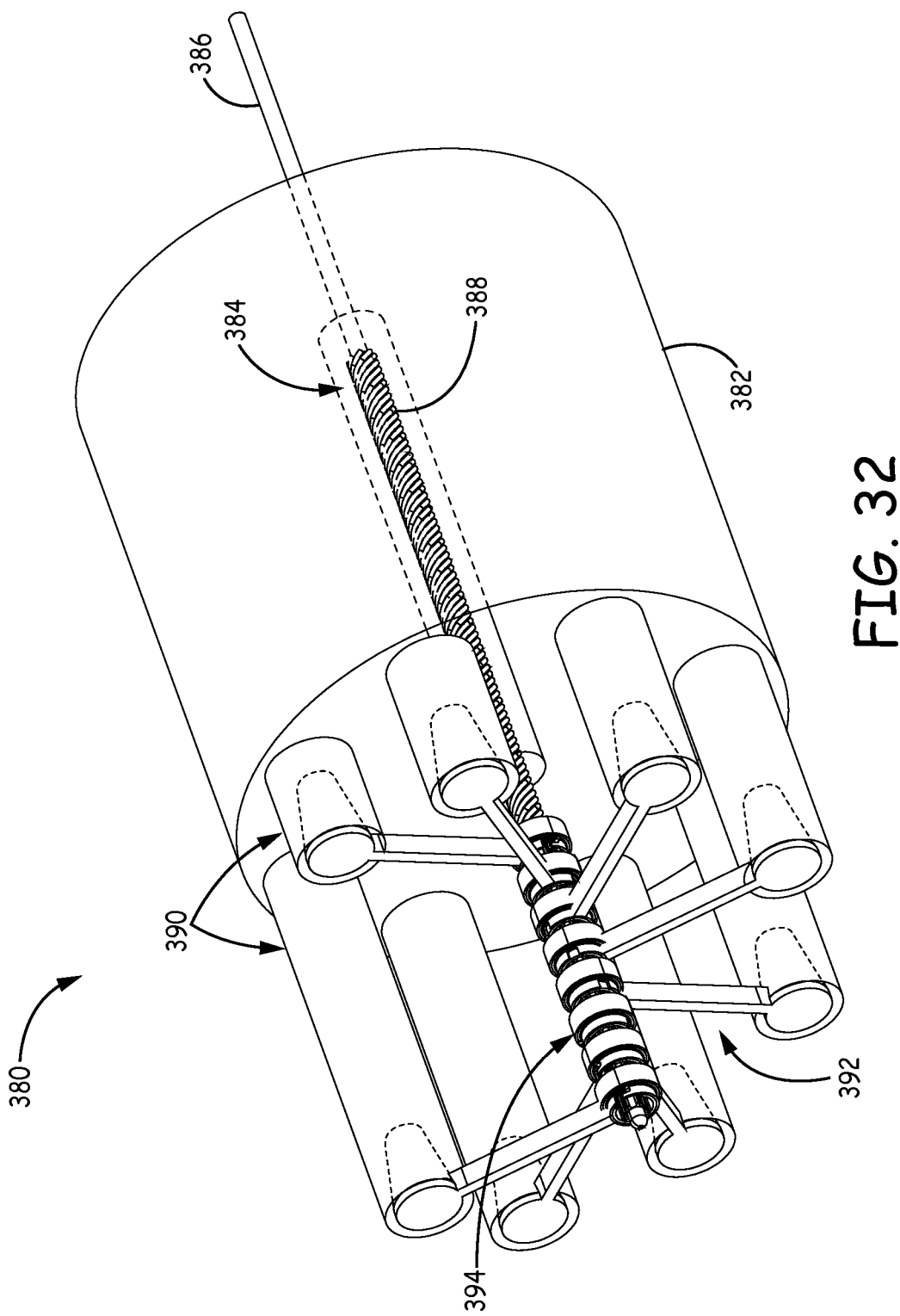

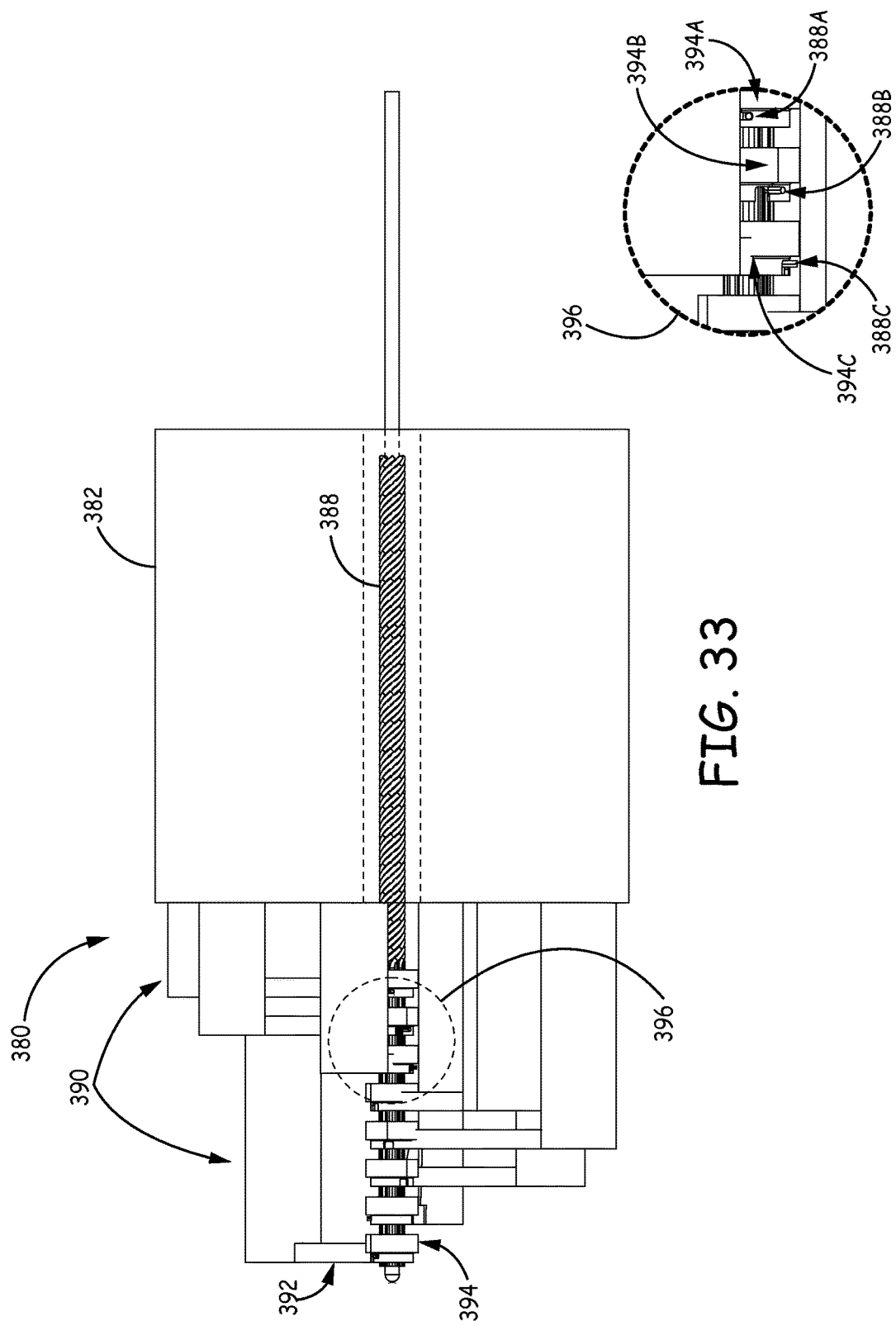

US 10,549,088 B2

STRUCTURES AND TECHNIQUES FOR MEDICAL LEAD FABRICATION

TECHNICAL FIELD

The present disclosure relates to medical devices, more particularly to medical leads configured for delivering electrical signals and/or sensing electrical signals.

BACKGROUND

Implantable electrical stimulators have been proposed for use to treat a variety of symptoms or conditions, such as chronic pain, tremor, Parkinson's disease, epilepsy, urinary or fecal incontinence, sexual dysfunction, obesity, or gastroparesis. An electrical stimulator may be configured to deliver electrical stimulation therapy to a patient via one or more medical leads that include electrodes implanted proximate to a target tissue within the patient, such as a target tissue site proximate the spinal cord, pelvic nerves, peripheral nerves, or within the brain or stomach of a patient. Hence, electrical stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

Electrical stimulation may be delivered via one or more implanted or percutaneous leads, each lead carrying one or more electrodes. The electrodes may take the form of, e.g., ring electrodes, cuff electrodes, paddle electrodes, segmented ring electrodes. Leads may be constructed, for example, by welding each electrode to a conductor (e.g., a wire) disposed within a lead body of the lead. When completed, an electrical signal generated by the electrical stimulator may be transmitted through one or more conductors and respective electrodes of the lead to generate an electrical field within the patient.

SUMMARY

In general, the disclosure is directed to devices, systems, and techniques for fabricating a medical lead, which may include multiple electrodes. In one example, a lead is fabricated using one or more electrode fixtures, which are configured to facilitate alignment of electrodes of the lead to respective conductors of the lead, as well as facilitate alignment between the electrodes. Each electrode fixture may comprise surfaces or structures that aid in the axial alignment between electrodes of the lead and/or the circumferential alignment between multiple electrodes to be disposed around the outer circumference of the lead. In this manner, each electrode fixture may retain one or more electrodes during fabrication of the lead. The electrode fixtures may also be configured such that each conductor may be welded or otherwise coupled to its respective electrode and, in some examples, a lead body can be molded while the electrode fixtures retain respective electrodes.

In one example, the disclosure is directed to a method that includes positioning an electrode fixture at least partially around at least one conductor of a plurality of conductors for a medical lead, wherein the electrode fixture at least partially retains an electrode assembly, and, when the electrode assembly is at least partially retained by the electrode fixture, electrically coupling a portion of the at least one conductor with at least a portion of the electrode assembly at an attachment area defined by the electrode assembly.

In another example, the disclosure is directed to a system that includes an electrode assembly that defines an attachment area configured to be electrically coupled to a conductor of a plurality of conductors for a medical lead and an electrode fixture configured to at least partially retain an electrode assembly, wherein the electrode fixture is further configured to be positioned around at least the conductor of the plurality of conductors, and, when the electrode assembly is at least partially retained by the electrode fixture, the electrode fixture is configured to facilitate access for electrical coupling of a portion of the conductor of the plurality of conductors to the attachment area of the electrode assembly.

In another example, the disclosure is directed to an assembly for fabricating a medical lead, the assembly including an electrode fixture including an electrode capture portion comprising an inner surface that defines a channel, wherein the electrode capture portion is configured to at least partially retain an electrode assembly against the inner surface of the channel, a proximal surface configured to contact a first structure, a distal surface configured to contact a second structure, and a registration structure configured to circumferentially align the electrode fixture to at least one conductor of a medical lead.

In another example, the disclosure is directed to a system that includes means for at least partially retaining an electrode assembly, wherein the means for at least partially retaining the electrode assembly is configured to be positioned at least partially around at least one conductor of a plurality of conductors for a medical lead and means for, when the means for at least partially retaining the electrode assembly at least partially retains the electrode assembly, electrically coupling a portion of the at least one conductor with at least a portion of the electrode assembly at an attachment area defined by the electrode assembly.

BRIEF DESCRIPTION OF DRAWINGS

The details of the present disclosure are set forth in the accompanying drawings and the description below. Other features, objects, and benefits will be apparent from the description and drawings, and from the claims.

FIG. 8 is a conceptual diagram illustrating an example electrode fixture positioned around a lead structure and a plurality of conductors.

FIGS. 25 and 26 are perspective views of an example support structure and electrode fixtures stacked to form the example system of FIG. 23.

FIG. 28 is a perspective view of an example system for fabricating a lead that includes electrode fixtures fitted within respective electrodes and including an arm to align the electrodes about conductors of a lead.

FIG. 32 is a perspective view of an example system for fabricating a lead that includes electrode fixtures fitted to circumferentially aligned posts to align respective electrodes about conductors of a lead.

FIG. 33 is a side view of the example system of FIG. 32.

FIG. 33A is a side view of access areas to electrodes and respective conductors between electrode fixtures of the example system of FIG. 32.

DETAILED DESCRIPTION

Figure 1A:
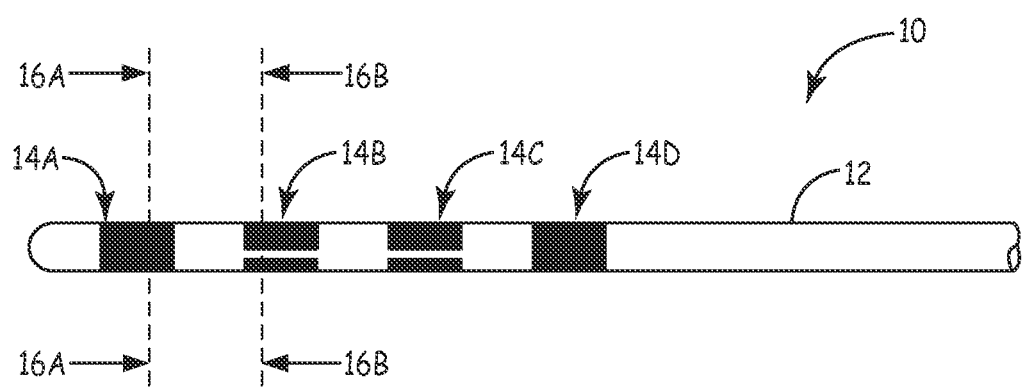
FIG. 1A is a conceptual diagram illustrating an example medical lead with ring electrodes and segmented ring electrodes.

Devices, systems, and techniques for fabricating a medical lead with one or more electrodes are described herein. In some examples of electrical stimulation therapy, a therapy system includes a medical device configured to generate electrical stimulation signals and a medical lead to deliver or transfer the stimulation signals to the patient. The lead may include one or more electrodes (e.g., disposed on a longitudinal surface, distal tip, or both of the lead) configured to deliver the electrical stimulation signals to the patient. The electrical stimulation energy that may emanate from the electrodes may define an electrical field with respect to the electrodes. In some examples, the lead may include an array of electrodes. A subset of the electrodes (referred to herein as an "electrode combination" or an "electrode configuration") may be selected to deliver the electrical stimulation. The array of electrodes may allow the lead to be configured to support hundreds or even thousands of different electrode combinations, e.g., to allow the lead to deliver stimulation therapy to a variety of different tissue regions from a single implant location of the lead in the patient. In this manner, a clinician may customize the electrical stimulation to treat specific symptoms or conditions of the patient.

Precise placement of each of the electrodes in an array of electrodes of a lead may be desired so that the electrical field produced by delivery of stimulation via electrodes of the array of electrodes is more predictable. The "placement" of the electrodes refers to, for example, the orientation and distance between electrodes of the lead, as well as the integrity of the electrical isolation between each of the electrodes. As electrode arrays on a lead become more complex, precise placement of the electrodes may become more difficult during lead fabrication. For example, precision placement of electrodes may be become more difficult to achieve as the size of electrodes decreases, the number of electrodes increases, and the spatial orientation of the electrodes becomes more complex (e.g., the orientation of multiple segmented ring electrodes around the outer circumference of a lead in addition to multiple axial positions on the lead).

Some lead fabrication processes utilize electrode positioning and/or welding by hand. In other words, a fabrication worker may manually assemble the electrodes of a lead. Because this manual process may rely heavily on operator skill and consistency, manual fabrication techniques may result in electrode placement disparities (e.g., axial and/or circumferential position variations) between electrodes of each lead and variations in electrode placement between different leads.

As disclosed herein, various structures and techniques may be utilized to minimize variations in electrode positioning when fabricating a medical lead. Increasing the precision of electrode positioning during fabrication may improve impedance characteristics, increase control over electrode alignment, facilitate lead assembly with higher densities of electrodes, and decrease lead variability (e.g., variability between leads of the same type). Lead assembly may be automated, partially automated, or manual, but the processes and devices described herein may mechanize assembly of the medical lead to provide assembly efficiencies and minimize assembly variation.

For example, an electrode fixture may be used to retain the small parts of an electrode assembly during the fabrication process. An electrode fixture may be used to retain one or more electrodes (collectively an "electrode assembly") to be disposed at a specific axial region of the lead. The electrode fixture may then be used throughout one of more of the alignment, welding, and molding processes that may be involved when fabricating the lead. In some examples, an orientation tool may be used to insert the electrode assembly into the channel of the electrode fixture. If the electrode assembly includes multiple electrodes (e.g., multiple segmented ring electrodes), the electrode assembly may initially be formed or constructed with distal and/or proximal ends contiguous with the multiple electrodes. These distal and/or proximal ends of the electrode assembly may maintain circumferential spacing between the electrodes until the multiple electrodes are secured within an electrode fixture. Once the electrode assembly is secured within the electrode fixture, the proximal and/or distal ends of the electrode assembly may be removed or cut off while the electrode fixture retains the remaining portion of the electrode assembly (e.g., the individual multiple electrodes). In some examples, the electrode fixture may be interchangeably used for electrodes assemblies of one, two, three, four, or more electrodes.

In some examples, the electrode fixture may also be used to position the electrodes around the lead structure and align the electrodes to respective conductors coupled to the lead structure. In addition, in some examples, the electrode fixture may include a registration structure that is used to circumferentially orient (e.g., determine the pitch of the electrodes) the electrode fixture and the electrode assembly to the conductors and to other electrode fixtures. In other words, the registration structures from each electrode fixture may be used to align the electrode assemblies to each other or orient the electrode assemblies relative to each other on the lead structure. In some examples, the electrode fixtures may also stack against each other to axially align the electrode assemblies on the lead structure. In other examples, a spacer may be used between adjacent electrode assemblies to axially align the electrode assemblies.

After each electrode fixture is positioned on the lead structure or after all electrode fixtures have been positioned, a distal end of a conductor may be welded or otherwise coupled to a respective electrode retained within one of the electrode fixtures. This may be repeated for each electrode retained within the electrode fixture. Each electrode structure may be configured such that a welding tool can access each attachment area for each weld while the electrode is retained by the electrode fixture. After the conductors are electrically and mechanically coupled to the respective electrodes, the lead assembly may be molded to include a lead body. After the molding process, each of the electrode fixtures may be removed from the assembled electrodes and lead.

The leads described herein may be used to deliver a variety of electrical stimulation therapies to a patient. In one example, the lead may be used to deliver neuro stimulation therapy to a patient's brain, e.g., DBS. However, the features and techniques described herein are useful in other types of medical device systems, which may include other types of implantable medical leads and implantable medical devices. For example, the fabrication devices and techniques described herein may be used to fabricate cardiac leads for cardiac rhythm management devices (e.g., pacemakers or pacemaker-cardioverter-defibrillators). As other examples, the features and techniques described herein may be used for leads that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient.

In addition, leads described herein may be coupled at their proximal ends to a stimulation therapy controller (e.g., an implantable medical device) located remotely from the electrodes, but other configurations are also possible and contemplated. For example, a lead may be defined, at least in part, by a portion of a housing (e.g., a medical device housing) or a member coupled to a housing of a medical device. In another example, the lead may even include a stimulation generator, e.g., a microstimulator, located proximate to or at the stimulation site. In other examples, a lead may include a member at a stimulation site that is wirelessly coupled to an implanted or external stimulation controller or generator. The processes, devices, and systems described herein for fabricating a medical lead may be used with any medical device that includes electrodes may disposed on a surface of the device.

As described herein, axial, radial, and circumferential directions refer to a cylindrical coordinate system with respect to the lead that is being fabricated. In other words, the axial direction is the longitudinal direction parallel with a center axis defined by the lead. The radial direction is the direction orthogonal to or at a right angle to the center axis. In other words, the radial direction extends directly away from the center axis. The circumferential direction refers to the angular position or direction around the outer surface of the lead. Different circumferential positions with respect to the lead may vary by some angle centered at the center axis.

FIGS. 1A-3C illustrate example leads that may be fabricated in accordance with the processes, devices, and systems described. FIG. 1A is a conceptual diagram illustrating an example medical lead 10 with ring electrodes and segmented ring electrodes. As shown in FIG. 1A, lead 10 may include lead body 12 and electrode levels 14A, 14B, 14C, and 14D (collectively referred to as "electrode levels 14"). The processes, devices, and systems described herein may be used to fabricate a lead such as lead 10. In the example shown in FIG. 1A, electrode levels 14A and 14D each includes a single ring electrode within the respective level. Electrode levels 14B and 14C each includes three segmented ring electrodes at different angular positions (in the case of lead 10 with a circular cross-section, the angular position may be referred to as a circumferential position) around lead 10. Lead 10 having electrode levels 14 may be referred to as a "1-3-3-1" lead because each electrode level comprises one, three, three, and one electrode, respectively.

Lead 10 may also be described as including a complex electrode array geometry. A complex electrode array geometry may be an electrode array that includes at least one level of segmented ring electrodes (e.g., circumferentially positioned electrodes). In another example, a complex electrode array geometry may refer to an electrode array that includes electrodes centered in two, three, or even more planes. A complex electrode geometry may indicate any electrode array in which different electrode combinations may be used to deliver electrical stimulation in multiple directions away from the lead. Thus, the complex electrode array geometry may include multiple levels of segmented ring electrodes, segmented ring electrodes and ring electrodes, or any other combination of electrodes including at least one level of segmented ring electrodes. Segmented ring electrodes may generally be two or more electrodes located at different angular or circumferential positions around the circumference of lead body 12. Segmented ring electrodes or other complex electrode array geometries may be used to produce customizable stimulation fields (e.g., electrical fields that may affect or activate patient tissue) that may be directed to a particular side of lead 10 in order to isolate the stimulation field around the target anatomical region of a brain in DBS, for example.

Electrode levels 14 may be equally spaced along the axial length of lead 10. In other examples, at least two electrode levels of electrode levels 14 may be separated from adjacent electrode levels by different distances. In the example shown in FIG. 1A, the segmented ring electrodes of electrode level 14B are circumferentially aligned with respective electrodes of electrode level 14C. In other examples, segmented ring electrodes of different electrode levels may be positioned at different circumferential positions (e.g., circumferentially staggered electrodes). Lead 10 is shown as including four electrode levels 14. However, in other examples, lead 10 may include a different number of electrode levels, each having one or more electrodes. For example, lead 10 may include one to three electrode levels. In other examples, lead 10 may include five or more electrode levels. Electrode levels 14B and 14C may have two, three, four, or more segmented ring electrodes in some examples.

In some examples, lead body 12 may include a radiopaque stripe (not shown) along the outside of the lead housing. The radiopaque stripe may correspond to a certain circumferential location that allows lead 10 to be imaged when implanted in a patient. Using the images of the patient, the clinician can use the radiopaque stripe as a marker for the orientation of lead 10 within the patient. Determining the orientation of lead 10 may be useful for, e.g., programming electrical stimulation parameters and selecting an electrode configuration that may achieve a stimulation field defined by the clinician. In other examples, a marking mechanism other than a radiopaque stripe may be used to identify the orientation of lead 10. These marking mechanisms may include a non-radiopaque stripe or something similar to a tab, detent, or other structure on the outside of lead body 12. In some examples, the clinician may note the position of markings along a lead wire during implantation to determine and record the orientation of lead 10 relative to patient anatomy within the patient.

Lead 10 may have any suitable configuration. Lead 10 may be substantially cylindrical (e.g., cylindrical or nearly cylindrical) in shape (e.g., may have a circular or nearly circular cross-section when the cross-section is taken in a direction perpendicular to a longitudinal axis of lead 10). In other examples, however, lead 10 may have another suitable shape. For example, lead 10 may define one or more curves, e.g., a shape configured to reach target anatomical regions of the patient. In some examples, lead 10 may be similar to a flat paddle lead or a conformable lead shaped for the patient. Also, in other examples, lead 10 may for constructed of any of a variety of different polygonal cross sections taken transverse to the longitudinal axis of the lead. Although lead 10 may be generally flexible, a lead may include one or more portions that are semi-rigid or rigid to aid in implantation and/or achieve desired orientation of lead 10 within the patient.

Lead body 12 may be formed from an insulative biocompatible material. Example biocompatible materials may includes at least one covers of polyurethane, silicone, and fluoropolymers such as tetrafluroethylene (ETFE), polytetrafluroethylene (PTFE), and/or expanded PTFE (i.e. porous ePTFE, nonporous ePTFE). Lead body 12 may be a molded lead body that at least partially surrounds a lead structure that supports the electrodes and plurality of conductors (e.g., electrically conductive wires) that electrically couple to respective electrodes of lead 10. In some examples, lead body 12 may be injection molded.

Within lead body 12, lead 10 may also include insulated electrical conductors (not shown) each coupled to at least one electrode of electrode levels 14. In some examples, the conductors may be coiled along part or all of the length of lead body 12 (e.g., in a multiconductor coil). In other examples, the conductors may be substantially straight instead of coiled. In either case, the conductors may be straightened or curved at their distal end (e.g., near their respective electrode) to be mechanically coupled to an electrode. In some examples, each of the conductors may be electrically coupled to a single one of the electrodes of electrodes levels 14. In this manner, each of the electrodes may be independently activated. In other examples, a lead including multiple electrodes may include a multiplexer or other switching device such that one conductor may electrically couple to more than one electrode, and the lead may include fewer conductors than electrodes, while allowing each of the electrodes to be independently activated. The switching device may be responsive to commands from an IMD or an external source to selectively couple the electrodes to the conductors for delivery of stimulation or for sensing. In addition, in other examples, at least two of the conductors of lead 10 may be electrically coupled to a single one of the electrodes of electrodes levels 14.

Figure 1B:
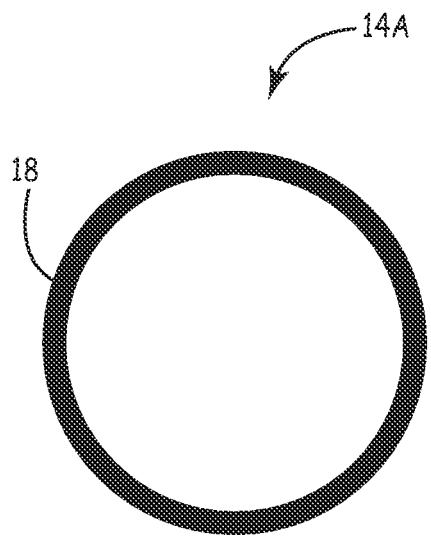
FIGS. 1B and 1C are cross-sections of the lead of FIG. 1A and illustrate cross-sections of an example ring electrode and example segmented ring electrodes, respectively.
Figure 1C:
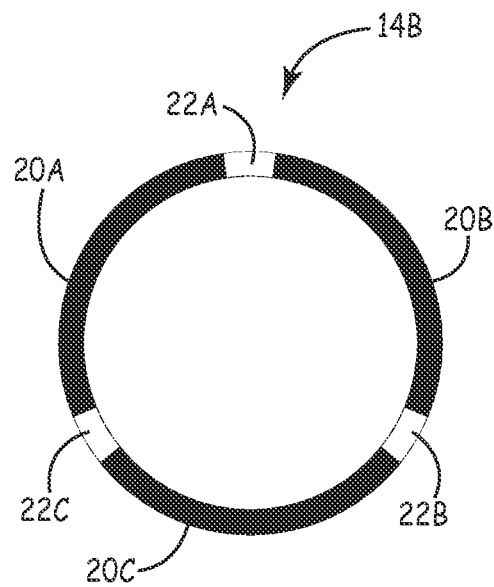

FIG. 1B is a cross-sectional view of lead 10 taken through electrode level 14A in a direction perpendicular to a longitudinal axis of lead 10 along plane 16A-16A in FIG. 1A, and illustrates an example ring electrode 18. FIG. 1C is a cross-sectional view of lead 10 taken through electrode level 14B in a direction perpendicular to a longitudinal axis of lead 10 along plane 16B-16B in FIG. 1A and illustrates example segmented ring electrodes 20A, 20B, and 20C (collectively "electrodes 20"). Electrode levels 14A and 14B may be similar to electrode levels 14D and 14C, respectively.

As shown in FIG. 1B, electrode level 14A includes a single ring electrode 18. Electrode 18 may be a circumferential electrode because electrode 18 encircles the outer entire circumference of lead 10. FIG. 1C shows electrode level 14B, which includes three substantially equally (e.g., equal or nearly equal) sized electrodes 20. Electrode 18 and electrodes 20 may each be referred to as an electrode assembly herein. In some examples, the electrodes of a particular level on the lead may be referred to as an electrode assembly. In other examples, any electrodes of a cross-section of a lead may be referred to as an electrode assembly.

In other words, an electrode assembly may describe one or more electrodes grouped together during the fabrication of a lead and may define one level of electrodes on the lead.

Electrodes 20 are distributed around an outer circumference of lead 10. Electrodes 20 may be independently programmed as anodes and/or cathodes for stimulation. In the example shown in FIG. 1C, each electrode 20A, 20B, and 20C may subtend approximately 110 degrees of the outer circumference of lead 10. Electrodes 20 may be electrically isolated from each other. For example, in the example shown in FIG. 1C, insulation areas 22A, 22B, and 22C (collectively "insulation areas 22") are disposed between adjacent electrodes 20 and are formed from an electrically insulative material. The size of insulation areas 22 may depend on the size of electrodes 20, as insulation areas 22 are positioned between adjacent electrodes 20. In the example shown in FIG. 1C, insulation areas 22 each reside along approximately 10 degrees of the circumference of lead 10. However, insulation areas 22, or non-electrode surface area, may be of any suitable size. For example, the insulation areas 22 may each subtend approximately 1 degree and approximately 50 degrees of the outer circumference of lead 10 in some examples. In other examples, insulation areas 22 may each subtend between approximately 25 degrees and approximately 40 degrees. Larger electrodes, e.g., smaller insulation areas, may allow a greater volume of tissue to be stimulated in some examples.

Electrodes 20 of lead 10 may have substantially equal sizes or may have different sizes. For example, the, electrode size may be varied around the outer circumference of lead 10. In addition, insulation areas may vary in size. Such asymmetrical electrode levels (asymmetrical relative to a longitudinal axis of lead 10) may useful for achieving certain shaped stimulation fields. As shown in FIG. 1C, electrodes 20 are flush or isodiametric with lead body 12. However, electrodes 20, for example, may be raised or depressed with respect to the surface of lead body 12. Each of electrodes 18 and 20 can be made from an electrically conductive, biocompatible material, such as a platinum iridium alloy.

Figure 2A:
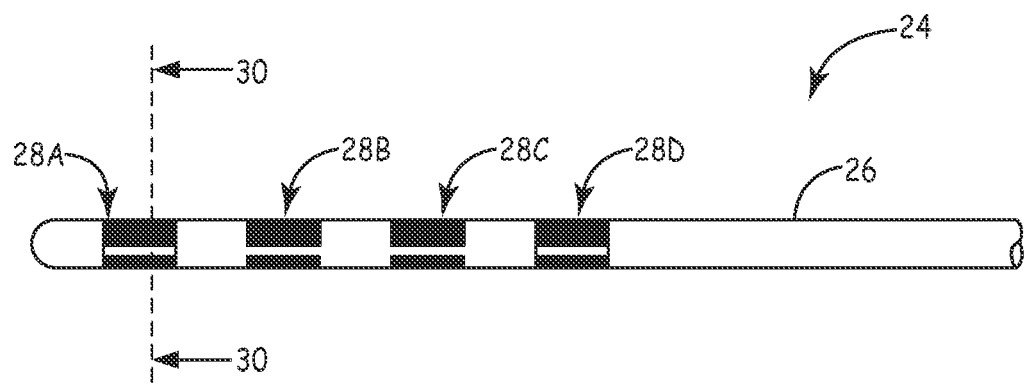
FIG. 2A is a conceptual diagram illustrating an example medical lead with four segmented ring electrodes in each electrode level.

FIG. 2A is a conceptual diagram illustrating another example medical lead 24, which includes four segmented ring electrodes in each electrode level. Lead 24 may be similar to lead 10 of FIG. 1A, but has a different electrode configuration than lead 10. The processes and devices described herein may be used to fabricate a lead such as lead 20 (or lead 10 of FIGS. 1A-1C). As shown in FIG. 2A, lead 24 may include lead body 26 and electrode levels 28A, 28B, 28C, and 28D (collectively "electrode levels 28"). Each of electrode levels 28 may include four segmented ring electrodes at different angular or circumferential positions around lead 10. Lead 10 having electrode levels 14 may be referred to as a "4-4-4-4" lead because each electrode level comprises four electrodes.

Figure 2B:
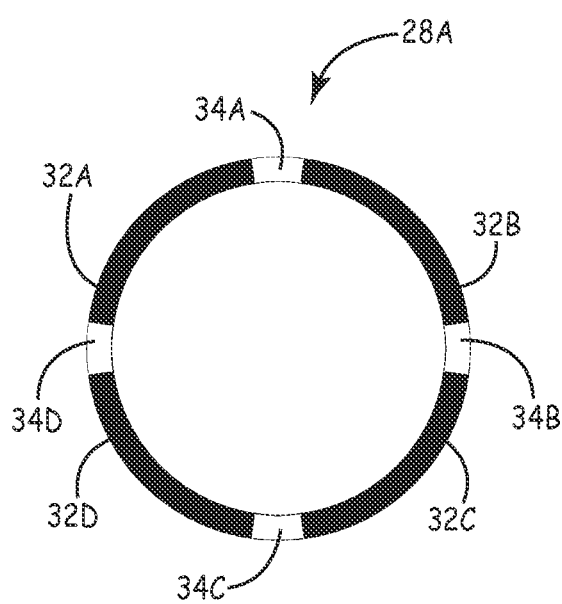
FIG. 2B is a cross-section of the lead of FIG. 2A and illustrates an example set of four segmented ring electrodes.

FIG. 2B is a cross-section of lead 24 taken through electrode level 28A along plane 30-30 in FIG. 2A, and illustrates an example set of four segmented ring electrodes 32A, 32B, 32C, and 32D (collectively "electrodes 32"). In the example shown in FIG. 2B, each electrode of electrodes 32 subtends (e.g., covers or extends over) approximately 80 degrees of the outer circumference of lead 12, and each of the insulation areas 34A, 34B, 34C, and 34D located between adjacent electrodes 32 subtending approximately 10 degrees of the outer circumference of lead 24. In other examples, up to ten or more electrodes may be included within an electrode level. In other examples, at least two adjacent electrode levels of lead 24 may include a different number of electrodes. In addition, the distance between adjacent electrode level or even the axial length (measured in a direction along the longitudinal axis of lead 24) of each electrode level may be varied. Further the above-described sizes of electrodes within an electrode level are merely examples, and other electrode sizes may be used with the fabrication techniques, devices, and systems described herein.

Figure 3A:
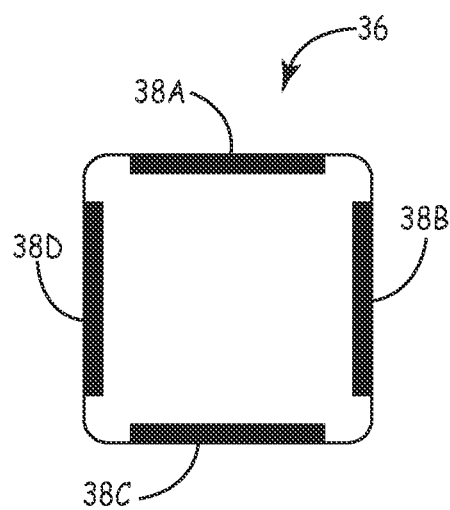
FIGS. 3A, 3B, and 3C are cross-sections of example electrodes disposed on leads of various cross-sectional shapes.
Figure 3B:
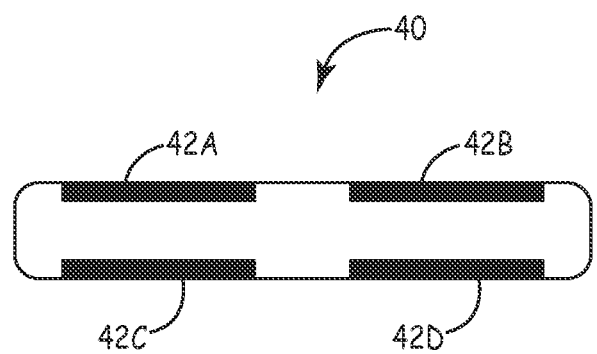
Figure 3C:
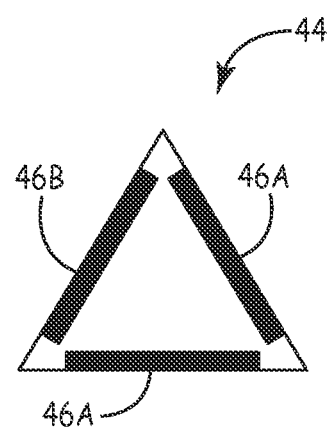

FIGS. 3A, 3B, and 3C are cross-sections of other example electrode arrangements of leads having various cross-sectional shapes. Although the fabrication of leads is primarily described herein with respect to cylindrical leads (e.g., leads 10 or 24), a lead of any cross-sectional shape may be fabricated using the techniques, devices, and systems described herein. For example, square lead 36 may be fabricated to include electrodes 38A, 38B, 38C, and 38D on respective sides of lead 36. In another example, paddle lead 40 may be fabricated to include electrodes 42A and 42B on one side of lead 40 and electrodes 42C and 42D on an opposite side of lead 40. In an another example, triangle lead 44, which includes a triangle shape cross-section, may be fabricated to include electrodes 46A, 46B, and 46C on each side of triangle lead 44.

Only a single electrode level for each of leads 36, 40, and 44 are illustrates for illustration purposes. Each of leads 36, 40, and 44 may include more than one electrode level, where each electrode level may include one or more electrode. In other examples, each side of leads 36, 40, or 44 may not include a separate electrode or a single electrode may cover two or more sides of leads 36, 40, or 44. The leads described herein may be constructed of any suitable cross-sectional shape or combination of any suitable cross-sectional shapes along the length of the lead.

Any lead described herein may be fabricated using an electrode assembly. The electrode assembly may include one or more electrodes and formed and/or constructed such that each electrode is fixed relative to each other electrodes. For example, the electrode assembly may be formed of a single continuous section of material. In another example, the electrode assembly may be constructed by welding, coupling, adhering, or otherwise joining the electrodes together for at least a portion of the electrode level.

This electrode assembly may then be secured or retained within an electrode fixture. The electrode fixture may be a structure that provides a channel sized to accept the electrode assembly. In other words, the electrode fixture may define a channel with a diameter selected to create a friction fit with the outer surface of the electrode assembly. Alternatively, the electrode fixture may include one or more prongs or latches that retain the electrode assembly in an axial and/or circumferential position with respect to the electrode fixture. Once the electrode assembly is retained by the electrode fixture, the electrode fixture may be used through one or more steps of the lead fabrication process to facilitate the precise axial and/or circumferential position of the electrode assembly with respect to the lead, conductors of the lead, and/or other electrode assemblies to the added to the lead. Once the electrodes of the electrode assembly are fixed within the fabricated, or at least partially fabricated, lead, the electrode fixture may be removed from the electrodes and the lead.

Figure 4A:
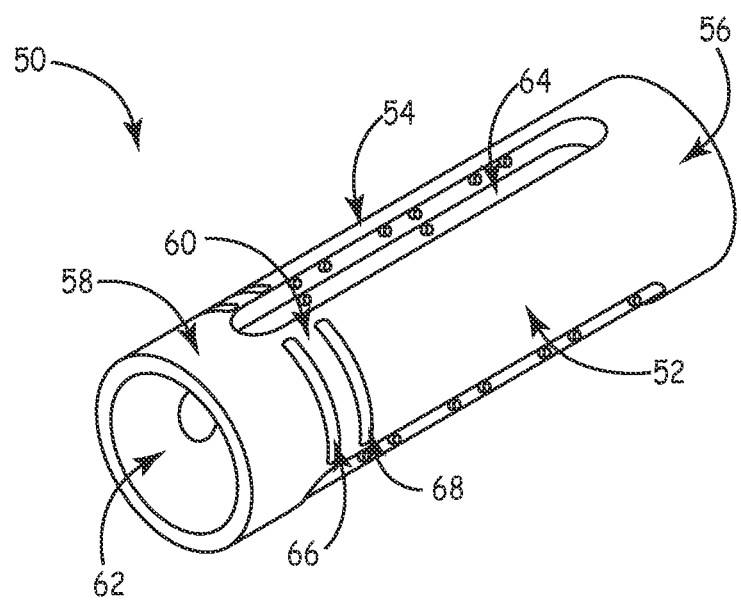
FIG. 4A is a conceptual diagram illustrating an example electrode assembly that includes three segmented ring electrodes.

FIG. 4A is a conceptual perspective view of an example electrode assembly 50 that includes three segmented ring electrodes. Electrode assembly 50 may be used to fabricate an electrode level of a lead, such as electrode level 14B of FIG. 1. In other words, each of electrode levels 14 of FIG. 1, for example, may be fabricated using an electrode assembly such as electrode assembly 50. As shown in FIG. 4A, electrode assembly 50 includes electrode portion 52, electrode portion 54, proximal portion 56, distal portion 58, and weld surface 60. Electrode assembly 50 also defines channel 62, insulation areas 64, cut gap 66, and attachment area 68. Electrode assembly 50 may include two or more electrode portions 52 and 54 (e.g., eventual segmented ring electrodes) disposed circumferentially around electrode assembly 50. A third electrode portion is not shown in the view of FIG. 4A.

Electrode assembly 50 may be constructed such that portions 52 and 54 are in fixed positions relative to each other and remain in this fixed position throughout the fabrication process such that the fixed positions of electrode portions 52 and 54 are translated into the final lead. During the fabrication process, electrode portions 56 and distal portions 58 are configured to be removed from electrode portions 52 and 54 such that electrode portions 52 and 54 are electrically isolated from each other. Including electrode portions 52 and 54 until an electrode fixture (not shown) retains and secures electrode portions 52 and 54 may allow the position of each electrode portion 52 and 54 to be fixed with respect to each other without individually placing electrode portions 52 and 54 within an electrode fixture. Individual electrodes may be difficult to manipulate due to their relatively small size and/or relatively fragile materials. Therefore, electrode assembly 50 may facilitate manipulation of the eventual electrodes during the fabrication process.

Electrode assembly 50 is an uncut electrode assembly. In other words, electrode assembly 50 includes additional electrode material that will not be used as a part of the electrodes disposed on a lead. An uncut electrode assembly may be used to fabricate segmented ring electrodes; the electrode assembly may facilitate handing of the relatively small individual electrode portions 52 and 54. Proximal portion 56 and distal portion 58 may be configured to keep the multiple electrodes disposed together and in a fixed position relative to each other until the electrode assembly 50 is retained within an electrode fixture.

As described herein, proximal portion 56 and distal portion 58 are configured to be removed from the central portion (e.g., electrode portions 52 and 54) of electrode assembly 50. For example, proximal portion 56 and distal portion 58 may be cut or otherwise removed at planes that intersect with the edges of insulation areas 64. Therefore, in examples in which portions 56, 58 are electrically conductive, each of the segmented ring electrodes (52 and 54 are shown in FIG. 4A) may be electrically isolated from each other after proximal portion 56 and distal portion 58 are removed. Until portions 56, 58 are removed from electrode assembly 50, portions 56, 58 may electrically connect electrode portions 52, 54. In the example shown in FIG. 4A, distal portion 58 may be removed at or near cut gap 66. In other examples, electrode assembly 50 may only include proximal portion 56 or distal portion 58 such that only one end of electrode assembly 50 is configured to be removed as part of the lead fabrication process.

Channel 62 may be defined by an inner surface of electrode assembly 50. Channel 62 may be configured to accept a shaft of orientation tool 70 (shown in FIG. 4B) and fit around a lead structure and one or more conductors of the lead. Weld surface 60 may be a notch or other surface to which a distal end of a connector can be electrically and mechanically coupled to electrode portion 52. Each electrode of electrode assembly 50 may include a respective weld surface and attachment area 68. Attachment area 68 may be a slot, opening, hook, flange, extended member, or even just an external surface or edge of an electrode of electrode assembly 50. In some examples, after distal portion 58 is removed from electrode assembly 50, weld surface 60 may be bent, crimped, or otherwise shaped into a surface that at least partially defines attachment area 68. In other examples, weld surface 60 may be provided in an alternative configuration.

Attachment area 68 defines a structure that can be used to mechanically and electrically couple a conductor to the respective electrode portions 52, 54. For example, attachment area 68 may be a slot or other opening into which the distal end of a conductor may be placed prior to mechanically and electrically coupling the conductor to the electrode portion 52.

Electrode assembly 50 is an example electrode assembly for an electrode level with three segmented ring electrodes. In other examples, electrode assembly 50 may be configured to fabricate another electrode level of a lead, such as an electrode level including a single circumferential electrode, in which case assembly 50 would only define one electrode, or an electrode level including two segmented ring electrodes, or four or more segmented ring electrodes, in which case the portions of electrode assembly 50 would be configured to define the plurality of electrodes.

Figure 4B:
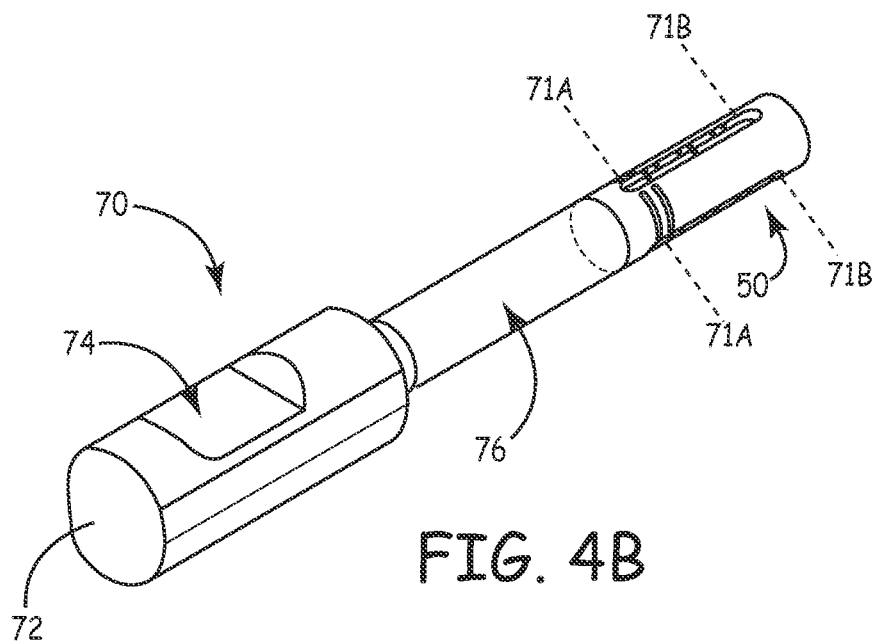
FIG. 4B is a conceptual diagram illustrating an example orientation tool inserted into a channel of the electrode assembly of FIG. 4A.

FIG. 4B is a conceptual perspective view of an example orientation tool 70 inserted into channel 62 of electrode assembly 50. As shown in FIG. 4B, orientation tool 70 includes handle 72, orientation groove 74, and shaft 76. Orientation tool 70 may be constructed of a polymer, metal alloy, composite, or any other material suitable for interfacing with electrode assembly 50. Orientation tool 70 may be used to orient electrode assembly 50 into the respective electrode fixture.

Shaft 76 may be configured to be fixed to electrode assembly 50. In one example, shaft 76 may be inserted into channel 62 of electrode assembly 50. For example, shaft 76 may have a circumference such that shaft 76 forms a friction fit to the inner surface of electrode assembly 50. In some examples, shaft 76 may be slightly tapered from a smaller diameter at the distal end of shaft 76 to a larger diameter near handle 72 to facilitate coupling with electrode assembly 50. In other examples, shaft 76 may be expandable to fill channel 62 and engage with channel 62 (e.g., to fix a relative position between tool 70 and electrode assembly 50) when needed and collapsible when shaft 76 is to be removed from electrode assembly 50. As an example, a button or slider may be actuated to expand at least a portion of shaft 76. Alternatively or additionally, shaft 76 may include an expandable bladder to temporarily couple shaft 76 to electrode assembly 50. In other examples, shaft 76 may be molded or formed directly to electrode assembly 50.

Handle 72 provides a structure by which a user or automated machine (e.g., a computer controlled arm) may grasp and manipulate tool 70. Handle 72 may be attached or formed to shaft 76. Handle 72 may also be configured to insert and align electrode assembly 50 within the channel of the electrode fixture. For example, in the example shown in FIG. 4B, handle 72 defines groove 74, which is configured to facilitate the circumferential and/or axial orientation of electrode assembly 50 to the electrode fixture. As an example, groove 74 may be configured to mate to a structure that also contacts and mates with the electrode fixture. An automated machine or a human hand may use groove 74 to orient shaft 76 to electrode assembly 50 and/or the electrode fixture.

Once electrode assembly 50 is positioned and retained within an electrode fixture, as described below with respect to electrode fixture 80 of FIG. 5A, proximal portion 56 and distal portion 58 may be removed from electrode assembly 50. For example, proximal portion 56 may be removed by creating a cut along the plane identified by 71B in FIG. 4B and distal portion 58 may be removed by creating a cut along the plane identified by 71A in FIG. 4B. These portions may be removed before or after shaft 76 is removed from channel 62 of electrode assembly 50.

Figure 5A:
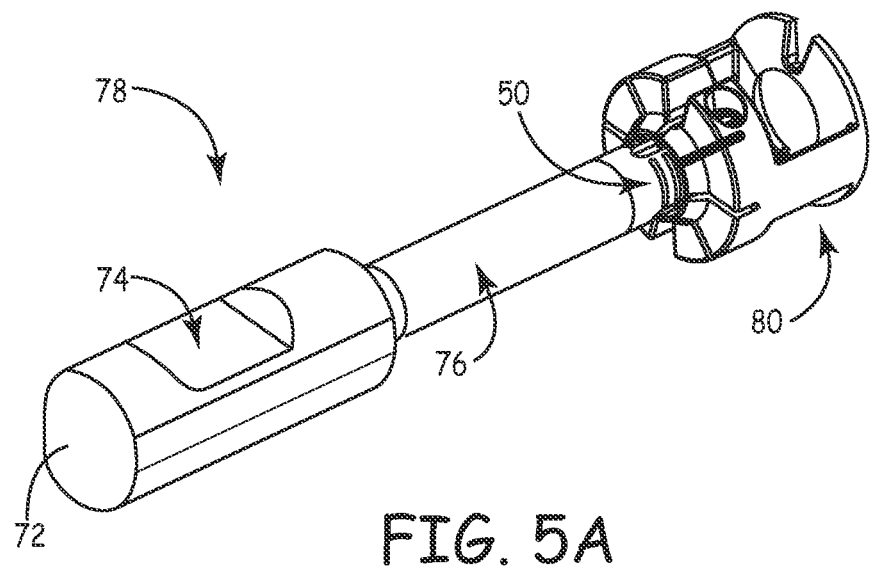
FIG. 5A is a conceptual diagram illustrating the example orientation tool and electrode assembly of FIG. 4B in conjunction with an example electrode fixture.

FIG. 5A is a conceptual perspective view of an example system 78 including an example orientation tool 70 and electrode assembly 50 in conjunction with an example electrode fixture 80. As shown in FIG. 5A, system 78 includes orientation tool 72, electrode assembly 50, and electrode fixture 80. Electrode fixture 80 may be configured to retain electrode assembly 50 through one or more assembly steps for the lead. As shown in FIG. 5A, orientation tool 70 may be used to assembly electrode assembly 50 with electrode fixture 80. In some examples, groove 74 of orientation tool 70 may be configured to register to electrode fixture 80, such that electrode assembly 50 is assembled with fixture 80 in one particular orientation. In other examples, orientation tool 70 may allow a user or a machine to circumferentially and/or axial align electrode assembly 50 within electrode fixture 80 in one more orientations, which may be predefined or selected ad hoc.

Electrode assembly 50 may be retained within electrode fixture 80 by a friction fit or other retaining mechanism. In other words, electrode fixture 80 may retain or secure electrode assembly 50 such that the electrode assembly does not move relative to electrode fixture 80. Electrode fixture 80 may function during the lead fabrication process to generally facilitate the placement of electrode assembly 50, and its associated electrodes, to the lead and other electrodes. For example, electrode fixture 80 may be used to fix the circumferential position of electrodes relative to each other within electrode fixture 80. Electrode fixture 80 may also be used to axially align electrodes from one electrode level to electrodes of another electrode level. Electrode fixture 80 may also be used to circumferentially align electrodes of one electrode level to electrodes of another electrode (e.g., circumferentially align electrode fixtures to each other). In addition, electrode fixture 80 may be used to align the electrodes to respective conductors of the lead for mechanical and electrical coupling of the electrodes to the conductors.

Once electrode assembly 50 is retained within electrode fixture 80, orientation tool 70 and shaft 76 may be removed from electrode assembly 50. As described herein, proximal portion 56 and distal portion 58 of electrode assembly 50 may both be configured to be removed from the central portion of electrode assembly when the central portion (e.g., defined by electrode portions 52, 54) is within electrode fixture 80. A cutting tool or other device may be used to simultaneously or sequentially remove proximal portion 56 and distal portion 58 from the central portion of electrode assembly 50 within electrode fixture 80. Electrode fixture 80 may be configured to expose proximal and distal portions 56, 58 of electrode assembly 50 so that proximal and distal portions 56, 58 may be relatively easily removed from assembly 50. For example, as shown in FIG. 5A, fixture 80 may be configured such that each of proximal portion 56 and distal portion 58 are disposed outside of an electrode caption portion 92 (described with respect to FIG. 5B) of electrode fixture 80 when electrode portions 52, 54 of assembly 50 are captured by electrode portions 52, 54 of electrode fixture 80.

In other examples, orientation tool 70 may not be removed from electrode assembly 50 prior to removing electrode potions 52, 54. Instead, the proximal end of shaft 76 may be removed from the distal end (e.g., the end of shaft 76 within electrode assembly 50) when proximal portion 56 is removed from electrode assembly 50. The distal end of shaft 76 that remains within electrode fixture 80 may then be removed (e.g., slid out, cut away, or drilled out) from the remaining central portion of electrode assembly 50.

Figure 5B:
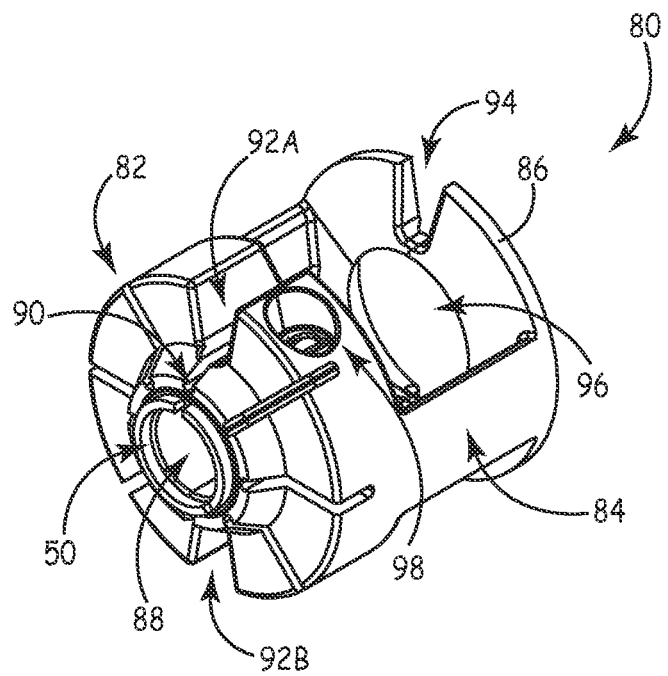
FIG. 5B is a conceptual diagram illustrating the example electrode fixture of FIG. 5A with an electrode assembly residing within a channel of the electrode fixture.

FIG. 5B is a conceptual diagram illustrating example electrode fixture 80 with electrode assembly 50 residing within channel 88 of electrode fixture 80, where proximal and distal portions 56, 58 have been removed from electrode assembly 50. As shown in FIG. 5B, electrode fixture 80 includes electrode capture portion 82, connection member 84, collar 86, and channel 88 defined by an inner surface of electrode capture portion 82. Electrode fixture 80 also defines conductor slot 90, registration structures 92A and 92B, registration structure 94, collar bore 96, and fixture identifier 98.

Electrode capture portion 82 may include an inner surface that defines channel 88. Electrode capture portion 82 may also be configured to retain electrode assembly 50 against the inner surface of channel 88. In this manner, electrode capture portion 82 may be the portion of electrode fixture 80 that contacts and retains electrode assembly 50 throughout the lead fabrication process (e.g., throughout electrical connection of conductors to the electrodes and formation of the lead body). Electrode capture portion 82 may be configured to retain electrodes of assembly 50 in fixed positions relative to each other throughout the lead fabrication process. Electrode capture portion 82 may also include one or more conductor slots 90 on the distal surface of electrode capture portion 82. Conductor slots 90 may be areas configured to accept a distal portion of a conductor when the distal end is curved over an end of electrode assembly 50. In this way, conductor slots 90 may help align conductors with respective electrodes during welding of the conductors to the electrodes of electrode assembly 50.

Collar 86 may be mechanically coupled to electrode capture portion 82 and configured to contact another electrode fixture. In other words, collar 86 may provide a surface with which another electrode fixture contacts to axially align electrode assembly 50 to the other electrode assembly. Collar 86 may be a disk shaped structure or separate structures within a single plane in other examples. In some examples, a surface of collar 86 configured to abut an adjacent electrode fixture is substantially parallel (e.g., parallel or nearly parallel) to a surface of electrode capture portion 82.

Collar 86 may also include registration structure 94 (and a corresponding registration structure not shown in FIG. 5B. Registration structure 92A of electrode capture portion 82 and registration structure 94 of collar 86, for example, may be aligned with registration structures from another adjacent electrode fixture. These registration structures may correspond to a common circumferential position such that aligning registration structures from adjacent electrode fixtures may allow circumferential alignment of electrode fixtures and the respective electrode assemblies retained therein. Collar 86 may also define collar bore 96. Collar bore 96 may be configured to accept a lead structure, one or more conductors, and a protrusion from an electrode fixture in some examples. Channel 88 and collar bore 96 may share a common axis in some examples.

Collar 86 may be coupled to electrode capture portion 82 via one or more connection member 84. Connection member 84 may be disposed between electrode capture portion 82 and collar 84 such that electrode capture portion 82 and collar 84 are disposed at opposing ends of electrode fixture 80. Connection member 84 may generally extend parallel to the axis of channel 88 and collar bore 96. In some examples, connection member 84 may be joined or fixed to electrode capture portion 82 and/or collar 84. In other examples, connection member 84 may be formed of a continuous material with electrode capture portion 82 and collar 86.

In some examples, electrode fixture 80 may include one or more registration structures on a surface of electrode capture portion 82 and collar 86. For example, electrode capture portion 82 may include one or more detents that extend from electrode capture portion 82 and collar 86 may include one or more indents that are formed into collar 86. The detents and indents may be disposed at specific radial and circumferential locations such that adjacent electrode fixtures can circumferentially align, or register, to each other when the one or more indents of one electrode fixture 80 mate with the one or more detents of an adjacent electrode fixture 80. Instead of indents and detents, electrode fixture 80 may include any alignment structures, such as female and male mating structures (e.g., interlocking tabs or other interlocking parts).

In other examples, registration structures 92A, 92B, and 94 may be used to remove electrode fixture 80 from electrode assembly 50. A fixture removal tool or other device may be placed within each registration structure and opposing circumferential forces may be applied to the structures via the removal tool to fracture or crack electrode fixture 80 at at least one location. In other words, a user or machine may separate fixture 80 into multiple pieces to remove electrode fixture 80 from electrode assembly 50 once the fixture is no longer needed (e.g., after the lead body has been molded). In one example, subsequent to molding the lead body around the lead structure and the plurality of conductors, electrode fixture 80 may be fractured in at least one location by applying circumferential forces to electrode fixture 80 in substantially opposing directions. These circumferential forces may be applied to one or more of registration structures 92A, 92B, and 94.

Although electrode fixture 80 is generally cylindrical in shape in the example shown in FIG. 5B, in other examples, electrode fixture 80 may be constructed in any shape to facilitate assembly of a lead. For example, electrode fixture 80 may be have a cross-sectional shape that is generally square, rectangular, triangular, a different polygon shape, or any amorphous shape. In some examples, a non-symmetrical shape may be used to circumferentially align multiple electrode fixtures.

Electrode fixture 80 may be constructed of any appropriate material. For example, electrode fixture 80 may be constructed of a polymer or a composite material. In other examples, electrode fixture 80 may be constructed of one or more metal alloys. In some examples, electrode fixture 80 may be constructed of multiple different materials. Electrode fixture 80 may be constructed as a disposable device or as a reusable device in other examples. In some examples, electrode fixture 80 may be constructed of a high temperature plastic that may be compatible with overmolding such as the injection molding used to create the lead body. As examples, high temperature thermoplastics may be polyetheretherketone (PEEK), phenolics, or polyetherimide. The material or combination of materials selected for electrode fixture 80 may or may not be biocompatible.

Different electrode fixtures 80, 130, 200, 206, 222, and 252 are described herein. Each of these electrode fixtures may differ as the attachment area, registration structure, or alignment processes used. However, each electrode fixture may be configured to retain or secure an electrode assembly for one or more steps of the fabrication process. Various features of the electrode fixtures may be utilized by other electrode fixtures in other examples.

Figure 6A:
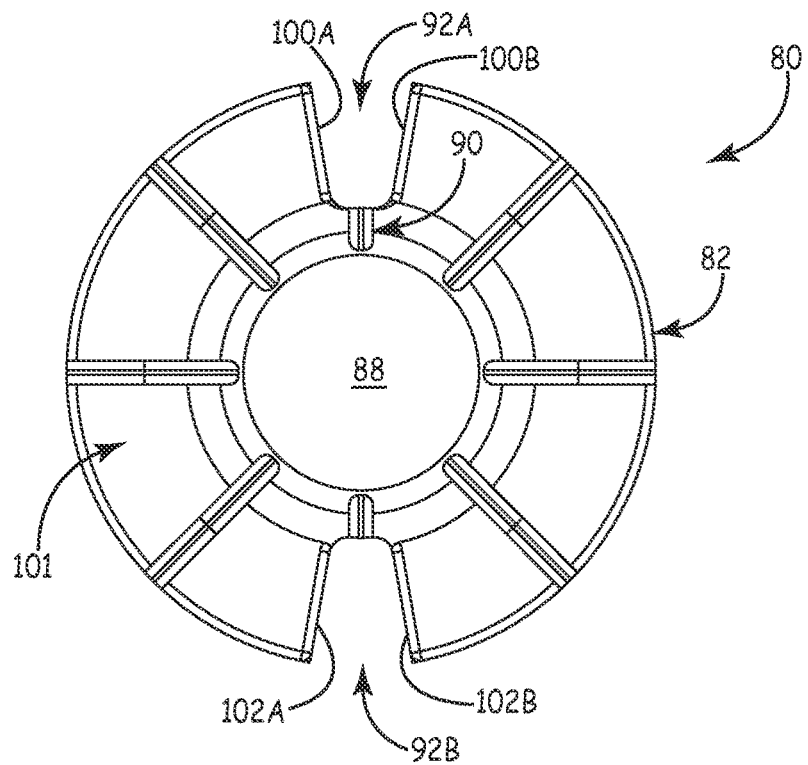
FIGS. 6A and 6B are front and back end views, respectively, of the example electrode fixture of FIG. 5B.
Figure 6B:
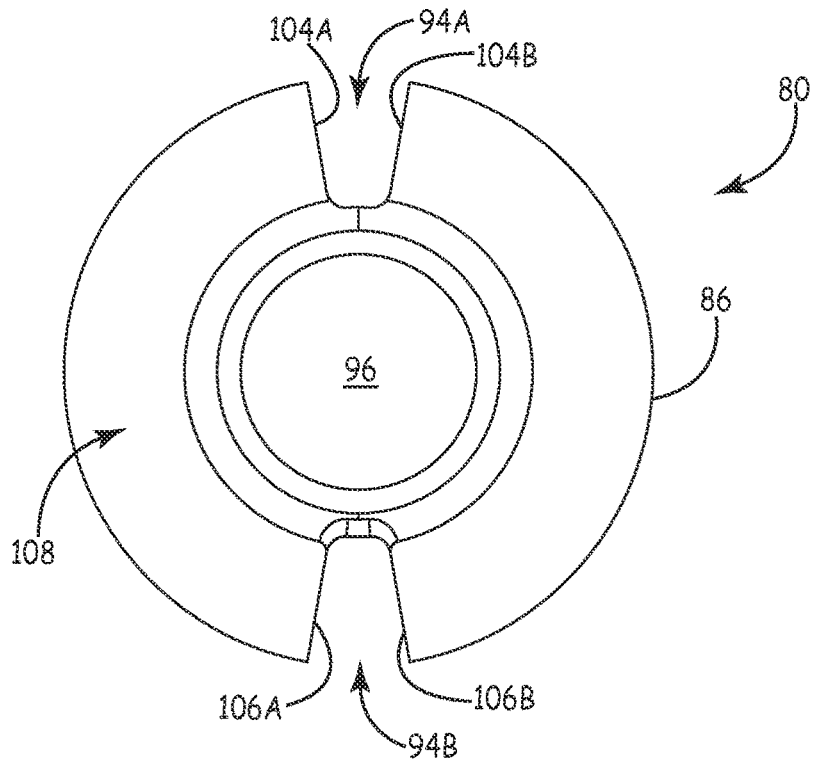

FIGS. 6A and 6B are front and back end views of example electrode fixture 80. As shown in FIG. 6A, front end view of electrode fixture 80 may include distal surface 101. Distal surface 101 may be disposed on an external surface of electrode capture portion 82 and may extend in a direction substantially orthogonal to the center axis of channel 88. Distal surface 101 may be configured to contact another structure, such as another electrode fixture or a spacer between electrode fixture 80 and another electrode fixture.

Conductor slot 90 is one of eight conductor slots locate on electrode capture portion 82. Each conductor slot may be configured to accept a distal end of a conductor for welding the conductor to a portion of the electrode assembly. In other examples, electrode fixture 80 may not include any conductor slots or may include a different number of conductor slots.

In the example shown in FIG. 6A, registration structures 92A and 92B are shown approximately 180 degrees apart from each other. Because each electrode fixture of a plurality of electrode fixtures may include similar registration structures, each registration structure (e.g., registration structures 92A and 92B) may be configured to circumferentially align the fixture to at least one registration structure of another electrode fixture, a lead structure, or at least one conductor coupled to the lead structure. Registration structure 92A may be at least partially defined by generally opposing surfaces 100A and 100B. Similarly, registration structure 92B may be at least partially defined by generally opposing surfaces 102A and 102B. Each of surfaces 100A, 100B, 102A, and 102B may face a circumferential direction and extend in the radial and axial directions. In this manner, registration structures 92A and 92B may be disposed on circumferential surfaces of electrode capture portion 82.

In some examples, an operator (e.g., a human, or an automated or semi-automated device) may line up each of the registration structures 92A, 92B of adjacent electrode fixtures 80 to circumferentially align all of the respective electrode assemblies retained by the electrode fixtures. In other examples, an operator or device may use a straight bar or other device that fits within and registers to each of the registration structures along one side of the plurality of electrode fixtures. This bar may hold each of the electrode fixtures in their respective positions within the lead structure. Registration described herein may refer to a process when two or more surfaces mate to each other such that a desired alignment is achieved.

In some examples, registration structures 92A and/or 92B may serve an additional or alternative function for the fabrication process. Registration structures 92A and 92B may also be removal structures. For example, surface 100A may be a removal surface disposed at a first circumferential location of fixture 80, and surface 100B may be a removal surface disposed at a second circumferential location of fixture 80. Surface 100A may substantially oppose surface 100B. Surfaces 100A and 100B may also be configured to receive substantially opposing circumferential forces that fracture electrode fixture 80 and facilitate removal of electrode fixture 80 from the electrode assembly (e.g., electrode assembly 50). Surfaces 102A and 102B may similarly serve as removal surfaces in some examples.

The circumferential force applied to opposing surfaces 100A and 100B, for example, may be sufficient to fracture or create a crack in the radial direction of electrode capture portion 82, from surfaces 100A, 100B towards the axis of channel 88. Electrode fixture 80 may be formed or created of a material with such a thickness than fracture will not occur during expected use of electrode fixture 80 until the circumferential force is applied. In some examples, the fracture may be created without any structural weakness (e.g., a perforation or score) formed into electrode fixture 80. In other examples, electrode fixture 80 may include a perforation, score, or even a different material radially inward from registration structures 92A and 92B.

In some examples, a fixture removal tool may be used to apply the opposing circumferential forces to surfaces 100A and 100B. The removal tool may be wedge-like shaft, such as a flat-head screwdriver, that is twisted within registration structure 92A to fracture electrode fixture 80. In other examples, the removal tool may include opposing heads attached to respective shafts. When the shafts are squeezed together, the opposing heads may extend away from each other and against respective surfaces 100A and 100B. In this manner, the fixture removal tool may be configured to apply a circumferential force in a first direction to surface 100A and a circumferential force in a second direction to surface 100B until the electrode fixture is fractured for removal from the electrode assembly. The first direction may be substantially opposite of the second direction. Similarly, the fixture removal tool may be applied to surfaces 102A and 102B of registration structure 92B or any other registration structures or removal surfaces described herein.

As shown in FIG. 6B, collar 86 may be disposed on the proximal end of electrode fixture 80. Collar 86 may also include proximal surface 108. Proximal surface 108 may be configured to contact another structure, such as the distal surface 101 of another, adjacent electrode fixture. In this manner, collar 86 may serve to axially align electrode fixture 80 to an adjacent electrode fixture.

Collar 86 also includes registration structures 94A and 94B, which are similar to registration structures 92A and 92B in electrode capture portion 82. Registration structure 94A is at least partially defined by opposing surfaces 104A and 104B. Registration structure 94B is at least partially defined by opposing surfaces 106A and 106B. In this manner, collar 86 may include registration structures 94A and 94B on a circumferential surface of collar 86. Substantially opposing surfaces 104A and 104B, for example, within collar 86 may at least partially define registration structure 94A.

In other examples, electrode fixture 80 may include registration structures in addition to, or instead of, registration structures 92A, 92B, 94A, and 94B. For example, distal surface 101 may include one or more detents or other male registration structure that extends away from surface 101 in the axial direction. Proximal surface 108 may then include one or more indents or other female registration structure that is formed into proximal surface 108. When distal surface 101 of one electrode fixture contacts proximal surface 108 of another electrode fixture, the electrode fixtures may be circumferentially rotated until the male and female registration structures mate with each other. In this manner, the registration structures may be used to ensure that electrode fixtures, and the retained electrode assemblies, are circumferentially aligned with each other when fabricating the lead.

Figure 7A:
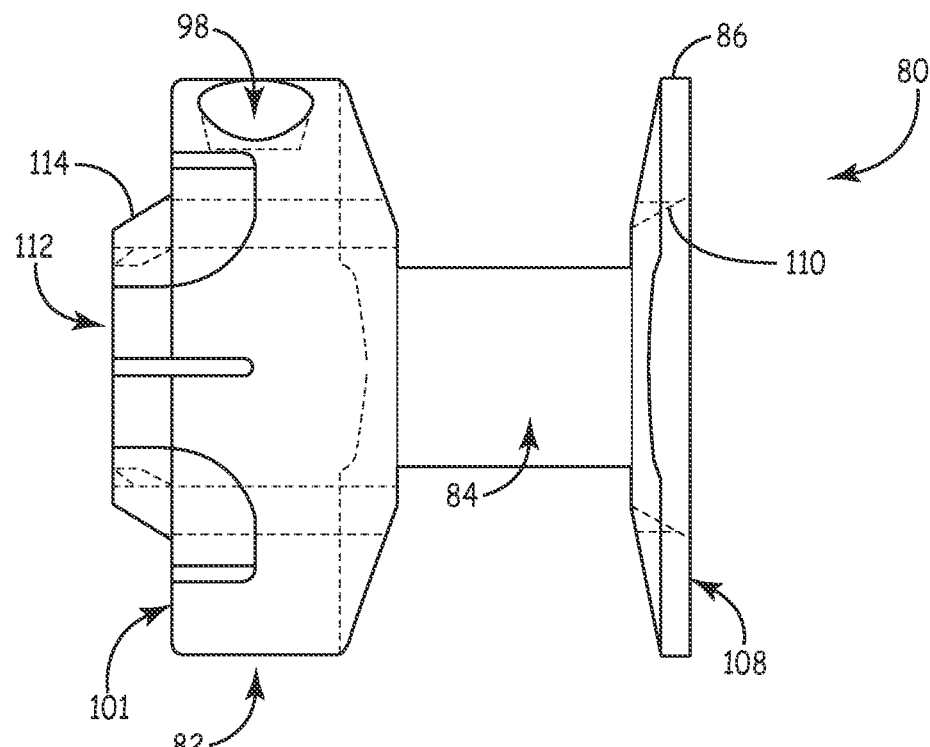
FIGS. 7A and 7B are side views of the example electrode fixture of FIG. 5B.
Figure 7B:
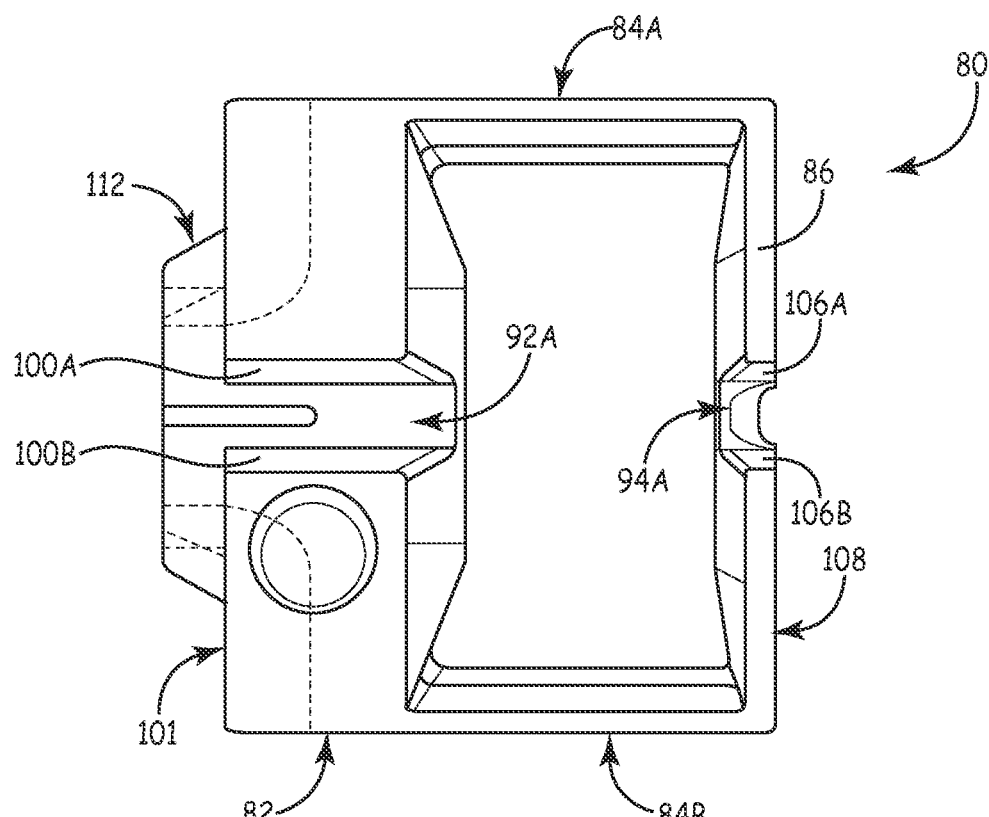

FIGS. 7A and 7B are side views of the example electrode fixture 80. As shown in FIG. 7A, electrode fixture 80 may include electrode capture portion 82, connection member 84, and collar 86. Electrode capture portion 82 may also define identifier 98, distal surface 101, projection 112, and tapered surface 114. Collar 86 may define proximal surface 108 and tapered surface 110.

Projection 112 may be configured to seat or align electrode fixture 80 to an adjacent electrode fixture. For example, tapered surface 114 of projection 112 may mate with tapered surface 110 of collar 86 (of another electrode fixture). When mated, proximal surface 108 of collar 86 may be configured to contact a distal surface (e.g., distal surface 101) of another electrode fixture. In this manner, multiple electrode fixtures may be stackable to each other. In some examples, tapered surfaces 114 and 110 may also define one or more registration structures that may be used circumferentially align two or more electrode fixtures.

Identifier 98 may include a letter, number, barcode, or other marking visible to the human eye or to a device, where the identifier distinguishes electrode fixture 80 from otherwise other electrode fixtures. In this manner, an operator or machine correctly position each electrode fixture in sequence on the lead structure during assembly, such that the lead that is fabricated includes the correct arrangement of electrode levels. Identifier 98 may be located within a depression of electrode capture portion 82, as shown in FIG. 7A, or at any other visible location on electrode fixture 80. In other examples, other types of techniques may be used to distinguish between electrode fixtures. For example, different electrode fixtures may be constructed of different colored materials and the specifications for a lead may indicate the colors of the electrode fixtures that will result in the correct sequence of electrode levels on the lead structure. As another example, each electrode fixture may include registration structures that only mate to one of a plurality of electrode fixtures.

Connection member 84 may connect or join electrode capture portion 82 and collar 86. Connection member 84 may generally extend in an axial direction between electrode capture portion 82 and collar 86. Although connection member 84 is shown as generally rectangular in shape, connection member 84 may be constructed of any cylindrical, curved, or angular shape. As shown in FIG. 7B, the shape of connection member 84 may at least partially determine the location at which access to an electrode of electrode assembly 50 is provide, e.g., during welding a conductor to an electrode when electrode fixture 80 is attached to the lead structure.

FIG. 7B illustrates another view of registration structure 92A of electrode capture portion 80, where structure 92A is at least partially defined by surfaces 100A and 100B. Electrode capture portion 82 also defines projection 112 and distal surface 101. Collar 86 may define proximal surface 108 and registration structure 94A. Surfaces 106A and 106B may at least partially define registration structure 94A. Registration structures 92A and 94A may also align to the same circumferential position to aid in the registration between adjacent electrode fixtures.

Connection member 84 includes connection members 84A and 84B, which are disposed between electrode capture portion 82 and collar 86 such that electrode capture portion 82 and collar 86 are disposed at opposing ends of electrode fixture 80. Although two connection members 84A and 84B are provided as an example, only one connection member or more than two connection members may be used to connect electrode capture portion 82 and collar 86. Connection members 84A and 84B may be sized and spaced circumferentially relative to the outer surface of electrode capture portion 82 to facilitate welding or coupling of conductors to respective electrodes between collar 86 and electrode capture portion 82. In some examples, connection members 84A and 84B may be formed with electrode capture portion 82 and collar 86. In other examples, connection members 84A and 84B may be joined or otherwise affixed to one or both of electrode capture portion 82 and collar 86.

Electrode fixture 80 may be constructed of any dimensions required to fabricate a lead with desired sizes of electrodes, diameters of the lead, cross-sectional shapes, or any other design choices. In one example, the outer diameter of electrode fixture 80 may be between approximately 1.0 millimeters (mm) and 10.0 mm. In another example, the outer diameter of electrode fixture 80 may be between approximately 2.0 mm and 5.0 mm. In a specific example, the outer diameter of electrode fixture 80 may be approximately 3.2 mm. The axial length of electrode fixture 80 may generally be between approximately 1.0 millimeters (mm) and 10.0 mm. In another example, the axial length of electrode fixture 80 may be between approximately 2.0 mm and 5.0 mm. In a specific example, the axial length of electrode fixture 80 may be approximately 3.2 mm. The largest width (e.g., the width furthest from the center axis of fixture 80) of registration structures 92A, 92B, and 94 may be generally between approximately 0.1 mm and 5.0 mm. In another example, the largest width of registration structures 92A, 92B, and 94 may be between approximately 0.3 mm and 0.8 mm.

FIG. 8 is a conceptual diagram illustrating a perspective view of an example system 120, which includes electrode fixture 130A positioned around lead structure 124 and a plurality of conductors 122, as well as electrode assembly 150 retained by electrode fixture 130A. Lead structure 124 and conductors 122, together, may be referred to as a coiled wire assembly. Lead structure 124 may be a spline or other structure that positions the distal ends of conductors 122 at specific circumferential locations to facilitate coupling of the conductors 122 to electrodes retained by electrode fixture 130A. In the example shown in FIG. 8, electrode fixture 130A may be the first electrode fixture to be added to lead structure 124 during the fabrication process. Electrode fixture 130A may retain electrode assembly 150. Electrode assembly 150 may be similar to electrode assembly 50 described herein, and electrode fixture 130A may be similar to electrode fixture 80. In some examples, features described with respect to electrode assembly 50 and electrode fixture 80 may be used to describe electrode assembly 150 and electrode fixture 130A, respectively.

The process for fabricating or assembling a lead may include positioning electrode fixture 130A around lead structure 124, e.g., such that lead structure 124 is received in a bore of electrode fixture 130A, and at least one conductor of the plurality of conductors 122 coupled to lead structure 124. Electrode fixture 130A may retain electrode assembly 150 at least partially within a channel of electrode fixture 130A, such that as electrode fixture 130A is positioned relative to lead structure 124, the electrodes of electrode assembly 150 are also positioned relative to lead structure 124. Electrode fixture 130A may be moved in the direction of arrow 126 to the appropriate axial position along lead structure 124. The target axial position of electrode fixture 130A may be fixed based on where conductor 128 can contact electrode assembly 150. Although the exact axial and/or circumferential position of electrode assembly 150 to conductor 128 and lead structure 124 may not be crucial during the fabrication process, the first electrode fixture 130A may be approximately positioned over lead structure 124 and conductor 128. Subsequent electrode fixtures may provide precise circumferential and/or axial alignment between each electrode. In other examples, lead structure 124 and/or conductors 122 may be coupled to an alignment block (e.g., a support structure) (not shown) that fixes the axial and/or circumferential position for electrode fixture 130A when the electrode fixture contacts the alignment block. The alignment block may thus be positioned proximal to all of electrode fixtures 130 of system 132 shown in FIG. 9.

As indicated above, distal ends of conductors 122 may be in a fixed position relative to lead structure 124. In some examples, electrode fixture 130A and electrode assembly 150 may be circumferentially oriented generally such that the distal end of a particular conductor 128 is adjacent to electrode assembly 150. In some examples, the first electrode assembly 5 may not need to be precisely positioned. Instead, it may be more important to precisely align subsequent electrode fixtures. In other examples, electrode fixture 130A may be aligned to a separate structure for registration to lead structure 124.

Figure 12A:
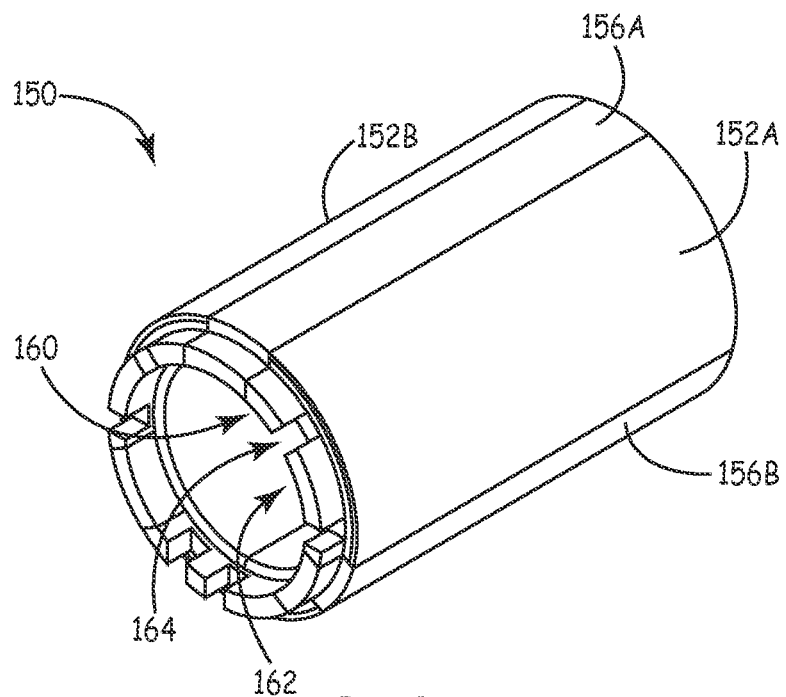
FIGS. 12A and 12B are perspective views of example electrode assemblies with different attachment areas for welding conductors to respective electrodes of the electrode assemblies.

The distal end of conductor 128 (one of the plurality of conductors 122) may be placed into or against an attachment area (e.g., attachment area 164 of electrode assembly 150 shown in FIG. 12A) defined by electrode assembly 150.

The attachment area may be specific to an individual electrode of electrode assembly 150. The distal end of conductor 128 can be mechanically and electrically coupled with at least a portion of electrode assembly 150 at the attachment area while electrode assembly 150 remains at least partially resides within the channel of electrode fixture 130A (e.g., a channel similar to channel 96 of electrode fixture 80). The coupling of conductor 128 to an electrode of electrode assembly 150 may be performed by any suitable technique, such as, but not limited to, one or more of edge welding, surface welding, ultrasonic welding, applying a conductive adhesive, or otherwise creating a mechanical and electrical coupling between conductor 128 and the electrode.

Figure 9:
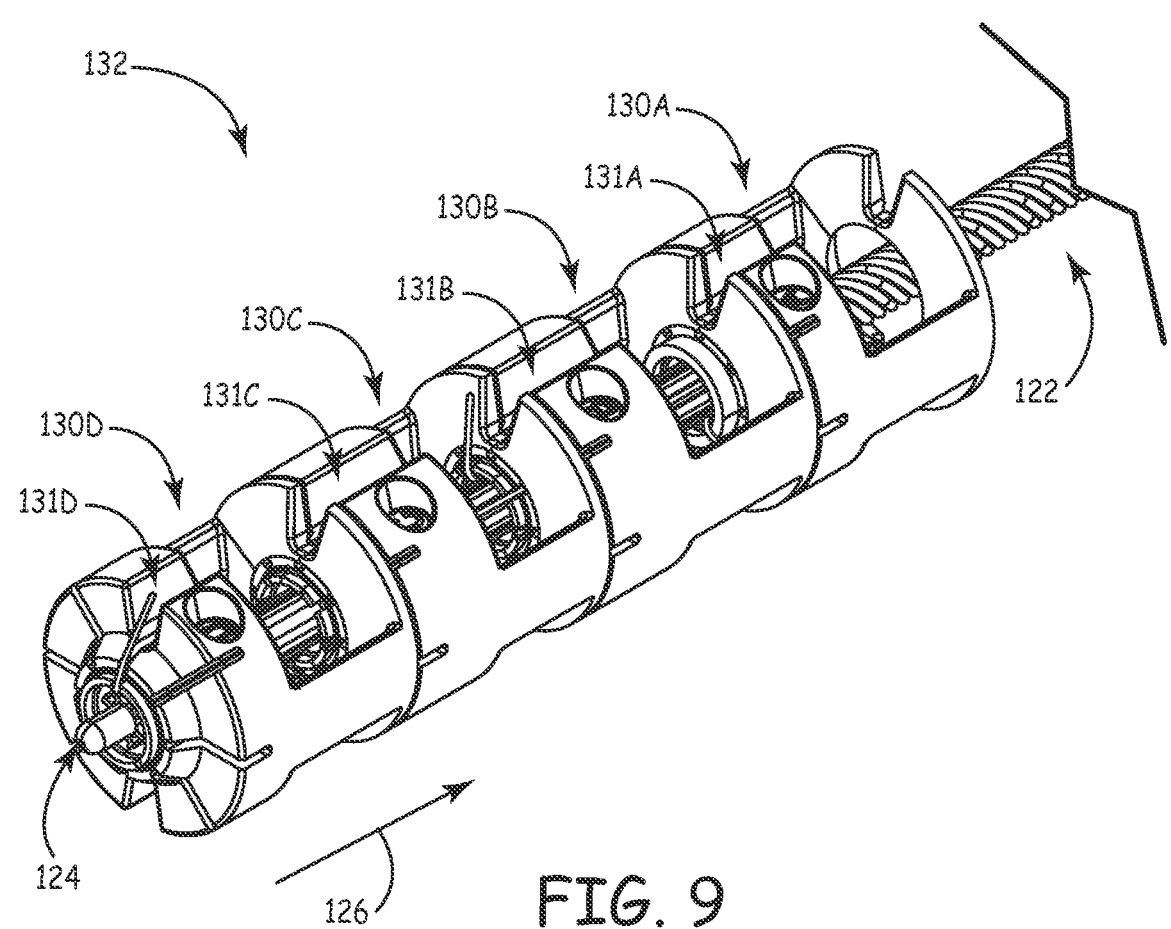
FIG. 9 is a conceptual diagram illustrating an example system that includes multiple example electrode fixtures stacked around the lead structure and the plurality of conductors of FIG. 8.

FIG. 9 is a conceptual diagram illustrating an example system 132 that includes multiple example electrode fixtures 130A, 130B, 130C, and 130D (collectively "electrode fixtures 130") stacked around lead structure 124 and the plurality of conductors 122. As shown in FIG. 9, electrode fixtures 130B, 130C, and 130D have been positioned onto lead structure 124 with electrode fixture 130A of FIG. 8. Each of electrode fixtures 130 may be similar and configured to retain a respective electrode assembly (e.g., electrode assembly 50). In addition, each of electrode fixtures 130 may be positioned around lead structure 124 in the direction of arrow 126.

Each of electrode fixtures 130 may include respective registration structures 131A, 131B, 131C, and 131D (collectively "registration structures 131"). Each of registration structures 131 may be configured to circumferentially align the respective electrode fixture 130 with an adjacent electrode fixture. For example, in the example shown in FIG. 9, adjacent electrode fixtures 130 may be aligned with each other by align the surfaces of adjacent registration structures 131, such that a channel extending between the electrode fixtures 130 is formed. In other words, registration structures 131 may be configured to ensure that each of the electrode assemblies retained by the respective electrode fixtures 130 may be circumferentially aligned to each other. Each of registration structures 131 may refer to the pair of registration structures (e.g., registration structures 92A and 94A) located in the electrode capture portion and the collar of each electrode fixture 130.

In addition, in some examples, distal and proximal surfaces of adjacent, or stacked, electrode fixtures 130 may be configured to contact and register the electrode assemblies to each other. Because each of the electrode fixtures 130 has a fixed structure, stacking the electrode fixtures 130 with each other, e.g., as shown in FIG. 9, sets (e.g., fixes) the spacing between the electrode assemblies retained by adjacent electrode structures. The registration between the distal and proximal surfaces, and the alignment of registration structures 131, may help ensure that the electrode fixtures 130 are positioned along lead structure 124 such that the axial distance between a first electrode assembly and a second electrode assembly is known, and so that the a circumferential position between the first electrode assembly and the second electrode assembly is known. In this way, the registration markers may help the lead assembler (whether human or automated or semi-automated device) place electrodes of the resulting lead at the intended positions (e.g., as indicated by the lead specifications).

In some examples, the conductors for each electrode assembly may be coupled (e.g., welded) to the respective electrodes prior to positioning the next electrode fixture on lead structure 124. For example, conductor 128 may be welded to electrode assembly 150 prior to positioning electrode fixture 130B in contact with electrode fixture 130A, and so forth.

In other examples, two or more of electrode fixtures 130 may be positioned prior to coupling each conductor to the portion of its respective electrode assembly. In this manner, each of electrode fixtures 130 may be quickly positioned and registered to each other. Then, the welding or coupling of conductors to portions of the electrode assemblies can occur in rapid succession. This approach may reduce fabrication and assembly time by grouping particular tasks in the assembly process. In addition, the openings within each electrode fixture between the electrode capture portion and the collar may facilitate welding after registration of each electrode fixture 130 is complete.

The axial alignment between adjacent electrode assemblies from registration of adjacent electrode fixtures 130 may produce axial separation between electrode levels. Generally, electrodes of adjacent electrode fixtures may be separate by an axial distance between approximately 0.1 mm and 10.0 mm. In another example, electrodes of adjacent levels may be separated by an axial distance between approximately 0.5 mm and 2.0 mm.

Figure 10:
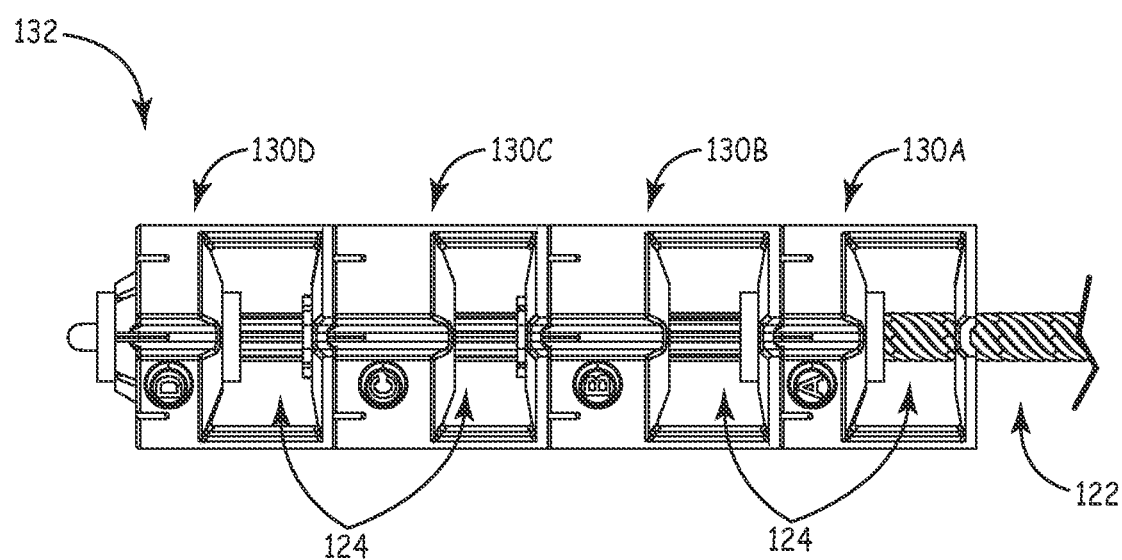
FIG. 10 is a side view of the example system of FIG. 9.

FIG. 10 is a side view of example system 132. As shown in FIG. 10, electrode fixtures 130 are circumferentially and axially aligned with each other on lead structure 124. In addition, each of electrode fixtures 130 includes an opening 124, which provides access to an underlying conductor 122. Openings 124 may be sufficiently large to allow welding to be performed between conductors 122 and respective electrodes held by electrode fixtures 130 while electrode fixtures 130 are positioned on lead structure 124.

Figure 11A:
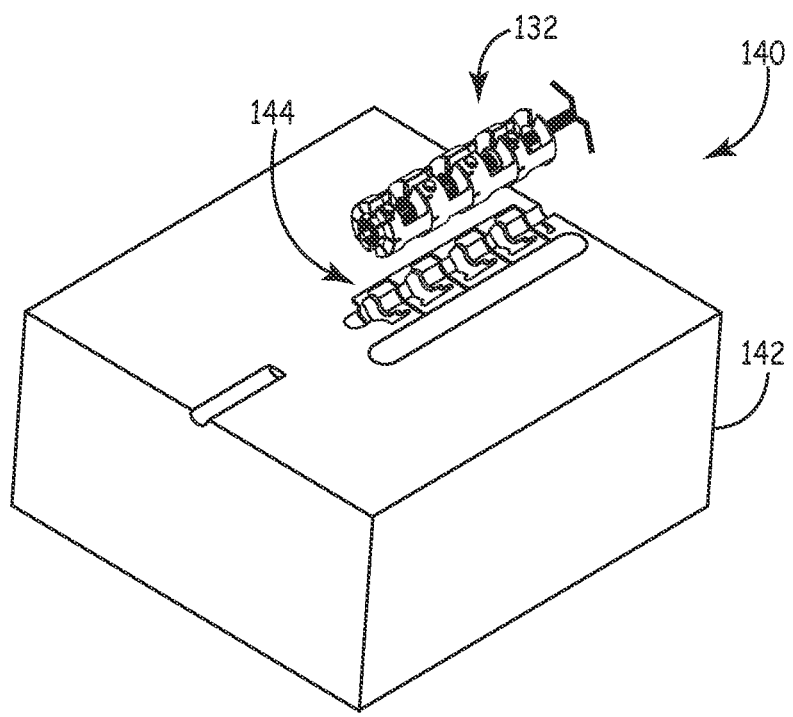
FIGS. 11A and 11B are perspective views of the system of FIG. 9 in conjunction with a mold form for molding the lead body.
Figure 11B:
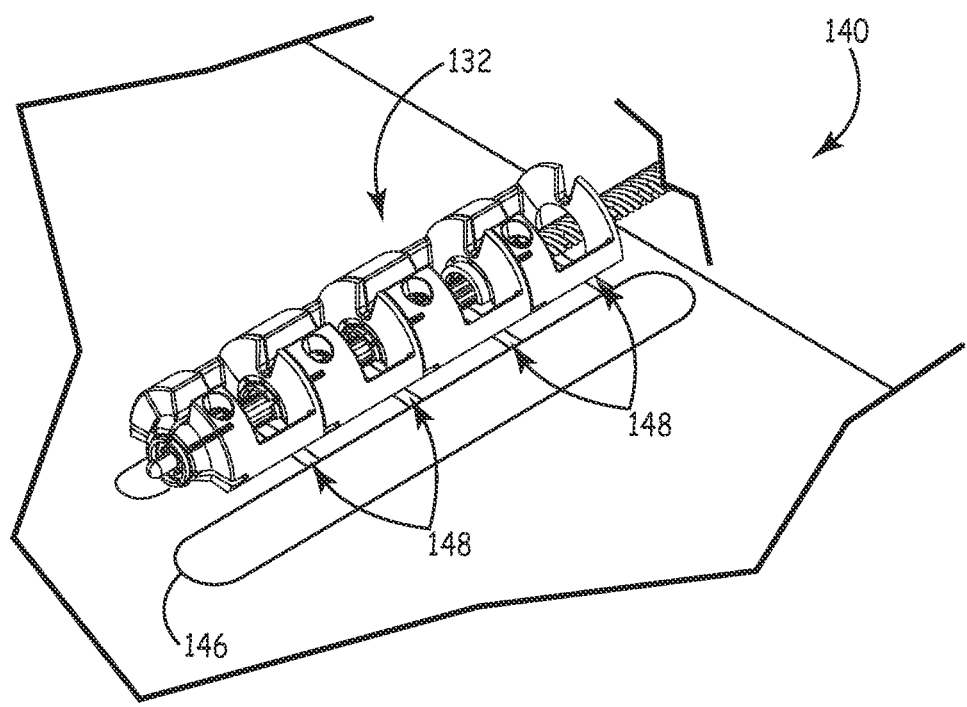

FIGS. 11A and 11B are perspective views of molding system 140 that includes system 132 in conjunction with mold form 142 for molding the lead body. System 132 with electrode fixtures 130 still positioned around the electrode assemblies, lead structure 124, and conductors 122. As shown in FIG. 11A, mold form 142 may be configured to stabilize the lead assembly (e.g., the portion of system 132 that includes lead structure 124, conductors 122, and electrodes of one or more electrode assemblies 50) prior to removing electrode fixtures 130. Mold 144 may define one or more mold cavities 144 that are each configured to receive a respective system 132. For example, as shown in FIG. 11A, mold cavities 144 may be formed to accept electrode fixtures 130, lead structure 124, and any other element of system 132. Another mold form 142 may be provided to completely surround system 132. In other words, two mold forms may encase system 132 prior to molding a lead body around the lead assembly of system 132.

As shown in FIG. 11B, system 132 is placed within mold cavity 144 of mold form 142. A polymer or other injection moldable material may be provided to (e.g., injected or otherwise introduced into) cavity 146. The material may flow through channels 148 and around lead structure 124, conductors 122, and electrode assemblies. In some examples, mold cavities 144 are formed such that the injected material does not encase any portion of electrode fixtures 130 to the lead body. The result of the injection molding process may be a lead body formed around the lead structure 124 and the plurality of conductors 122. In other examples, a lead body may be formed without injection molding (e.g., by applying individual lead body portions to the lead structure or dipping the lead into a moldable material).

After the injection mold process is complete, the finished lead may be removed from mold form 142. Subsequently, each of the electrode fixtures may be fractured or otherwise removed from the lead. In some examples, one or more of the electrode fixtures may be removed after the welding process has completed and prior to performing the molding process.

Figure 12B:
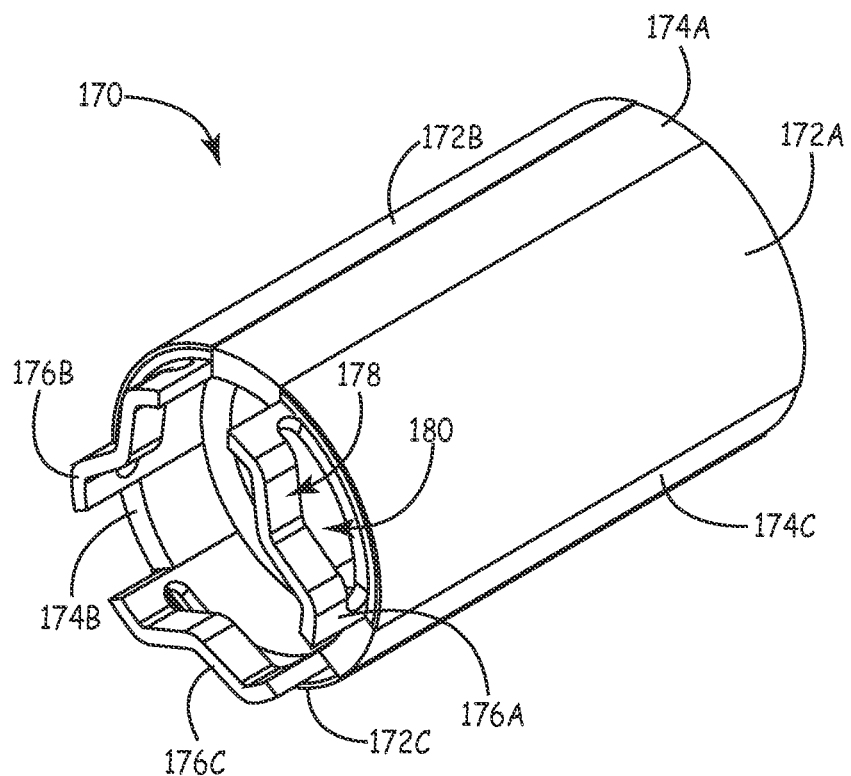

FIGS. 12A and 12B are perspective views of example electrode assemblies 150 and 170 with different attachment areas for welding conductors to respective electrodes of the electrode assemblies. Electrode assemblies 150 and 170 may be similar to electrode assembly 50 described herein. However, electrode assemblies 150 and 170 may have already been cut to remove the distal and proximal portion of the electrode assembly.

As shown in FIG. 12A, electrode assembly 150 may include three segmented ring electrodes 152A and 152B (the third electrode is not shown) and insulation areas 156A, 156B. Insulation areas 156A and 156B each electrically separate or insulate the segmented ring electrodes from each other. In addition, each of the electrodes may define an attachment area for coupling a distal end of a conductor to the respective electrode.

For example, electrode 152A includes weld portion 160 and weld portion 162. Weld portions 160 and 162 may be axial protrusions at the edge of electrode 152A. Weld portions 160 and 162 may also define attachment area 164. The distal end of a conductor may be inserted into attachment area 164 and held in place relative to electrode 152A by attachment area 164. While the distal end of the conductor is received by attachment area 164, the distal end of the conductor may be welded to opposing edges of weld portions 160 and 162. In other words, the conductor may be placed between weld portions 160 and 162 such that the weld may be formed to mechanically and electrically couple weld portions 160 and 162 to the conductor. This type of weld may be referred to as an edge weld. Any portion of the conductor disposed past the attachment area, defined by weld portions 160, 162 in FIG. 12A, may then be removed. This type of welding may be completed to couple a conductor to each of electrodes 152.

In other examples, the attachment area of electrode 152A or other electrodes may not be defined by specific structures, members, flanges, or other structure that extends from the electrode. Instead, the attachment area may be an edge of the electrode or any other interior or exterior surface of the electrode to which a portion of a conductor can be mechanically and electrically coupled to a portion of the electrode. In this manner, a conductor may be welded to any spot of the electrode that may support a weld or other method of coupling.

As shown in FIG. 12B, electrode assembly 170 may include three segmented ring electrodes 172A, 172B, and 172C. Insulation areas 174A, 174B, and 174C each electrically separate or insulate the segmented ring electrodes from each other. In addition, each of the electrodes 172A, 172B, and 172C may define an attachment area for coupling a distal end of a conductor to the respective electrode.

For example, electrode 172A may include weld tab 176A. Weld tab 176A may be a portion of electrode 172 that has been formed into a shape that facilitates coupling of the weld tab 176A to a conductor. In the example of FIG. 12B, weld tab 176A has been formed into notch 178 configured to cradle a conductor. Weld tab 176A may also define attachment area 180 (e.g., a slot that accepts the conductor). During a welding process, a conductor may extend axially outward from under electrode 172A and rest in notch 178. When in notch 178, the conductor may be positioned for welding or another technique for electrically and mechanically coupling the conductor to weld tab 176A. Each of electrodes 172B and 172C may also include similar respective weld portions 176B and 176C. Any portion of the conductor disposed past attachment area 180 may then be removed. This type of welding may be completed to couple a conductor to each of electrodes 172.

In some examples, weld tab 176A may be open on one end (e.g., weld tab 176A may be connected to electrode 172A by only one member instead of the two shown in FIG. 12B) to allow the conductor to be circumferentially curved onto notch 178. For example, the distal end of a conductor may extend out from within electrode assembly 170 and be curved or bent into the slot of attachment area 180. In other examples, weld tab 176 may be formed into an "L" shape hook that extends radially inward to cradle the conductor. Electrode assembly 170 may define a longitudinal center axis such that weld tab 176 is formed radially inward towards the center axis. Weld tabs 176A, 176B, 176C having an opening on one side may also allow for the conductors to be coiled toward the attachment area instead of being straightened prior to reaching the attachment area of the respective electrode.

Figure 13:
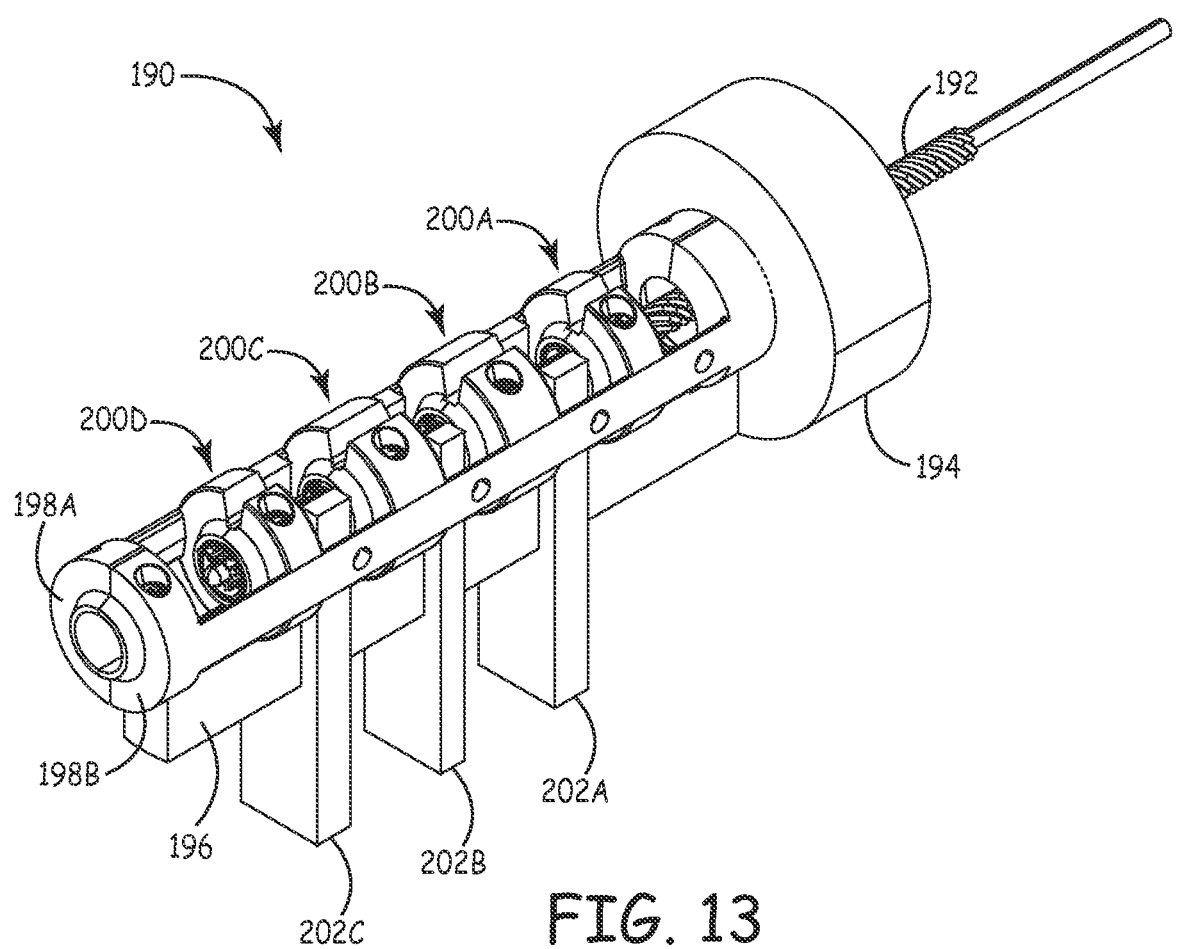
FIG. 13 is a perspective view of an example system for fabricating a lead that includes electrode fixtures and spacers to axially align each of the electrode fixtures.

FIG. 13 is a perspective view of an example system 190 for fabricating a lead that includes electrode fixtures 200 and spacers 202 configured to axially align each of electrode fixtures 200. System 190 may include lead holder 194, conductors 192, registering bar 196, stabilizing bars 198A and 198B, spacers 202, and electrode fixtures 200. As shown in FIG. 13, system 190 may include electrode fixtures 200A, 200B, 200C, and 200D (collectively "electrode fixtures 200"). Each of electrode fixtures 200 may be similar to electrode fixture 80 described herein. However, in some examples, electrode fixtures 200 may not include a collar or connection member. Instead, system 190 may utilize one of spacers 202A, 202B, and 202C (collectively "spacers 202") between adjacent electrode fixtures 200 to axially align electrode fixtures 200 to each other.

In the example shown in FIG. 13, electrode fixtures 200 are positioned around a lead structure, e.g., as shown in FIGS. 8-10 with respect to electrode fixtures 130. Registration bar 198 may be configured to aid with circumferential alignment between each of the electrode fixtures 200, such that the electrodes retained by the fixtures are in the appropriate circumferential positions for the lead being fabricated.

Prior to being engaged with registration bar 196, electrode fixtures 200 may be configured to rotate around the lead structure, such that the circumferential orientation of each of the electrode fixtures 200 relative to the lead structure may be changed, as needed. Each of electrode fixtures 200 may include a registration structure (e.g., similar to registration structure 92B shown in FIG. 6A) that is configured to mate and register with a surface of registering bar 196. Registration bar 196 may extend in the axial directional along the entire portion of the lead structure that will include electrodes. This registration with registration bar 196 may fix a circumferential position between the electrode assemblies of the respective electrode fixtures 200. In this manner, an operator may register the registration structure of each electrode fixture 200 to registration bar 196 in order to fix the circumferential position of the electrodes of electrode structures 200.

When spacers 202 are positioned between adjacent electrode fixtures 200, spacers 202 help to axially align the adjacent electrode fixtures 200 along the length of the lead structure (not visible) that includes conductors 192. For example, a distal surface of electrode fixture 200A may be registered to a first surface of spacer 202A. In addition, a proximal surface of electrode fixture 200B may be registered to a second surface of spacer 202B. Registration of surfaces may involve contact between an electrode fixture 200 and a spacer 202. The first and second surfaces may be substantially opposite of each other. Each electrode fixture 200A and 200B may contact opposing sides of space 202A. This mating of surfaces may be used to fix an axial distance between the electrode assemblies of electrode fixtures 200A and 200B. This process may be similarly completed to fix the axial distance or alignment between each of electrode fixtures 200 using respective spacers 202. In this way, spacers 202 may be configured to help axially align each of the electrode fixtures 200, such that the electrodes retained by the fixtures are in the appropriate axial positions (to define the different electrode levels) for the lead being fabricated.

Stabilizing bars 198A and 198B may contact the circumferential surfaces of electrode fixtures 200 to retain their circumferential and axial alignment to each other. In some examples, stabilizing bars 198A and 198B may be used to retain all electrode fixtures and/or spacers 202 until the lead body is injection molded. Stabilizing bars 198A and 198B may be added to electrode fixtures 200 after each of electrode fixtures 200 are positioned with respect to registration bar 196 and spacers 202.

In other examples, electrode fixtures 200 may circumferentially register directly to spacers 202 instead of or in addition to using registration bar 196 to provide the circumferential registration between electrode fixtures 200. For example, electrode fixtures 200 may include a distal surface configured to register against a first surface of an adjacent spacer 200 and/or a proximal surface configured to register against a second surface of an adjacent spacer 200. Once each of electrode fixtures 200 are positioned in contact with one or more adjacent spacers 202, the registration with the respective spacers 202 may fix an axial distance between respective electrode assemblies of electrode fixtures 200 and a circumferential position between the electrode assemblies of electrode fixtures 200.

Figure 14:
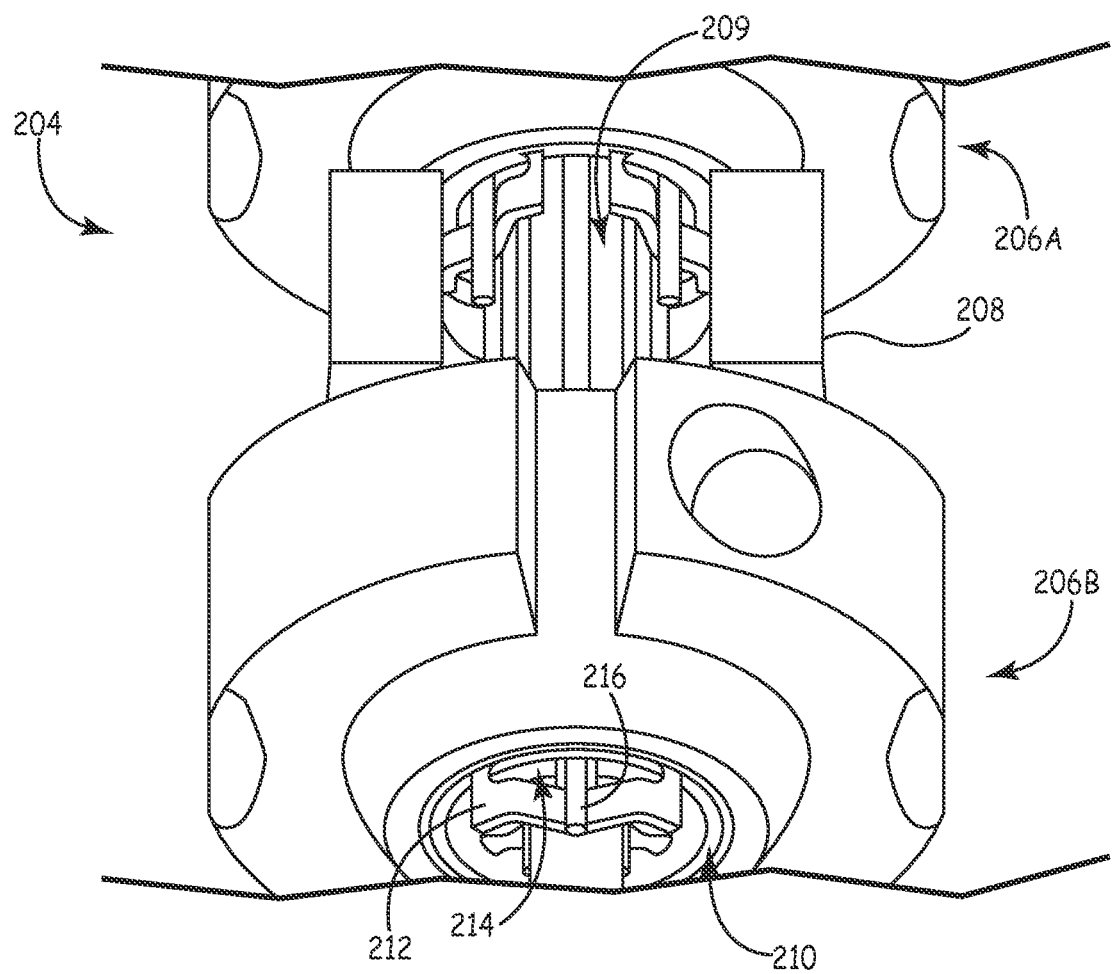
FIG. 14 is a top view of a distal end of a conductor in conjunction with an attachment area for welding the conductor to the electrode of the electrode assembly.

FIG. 14 is a top view of a distal end of conductor 216 in conjunction with attachment area 214 for welding conductor 216 to weld tab 212 of electrode assembly 210. System 204 may include the welding technique described with respect to electrode assembly 170 of FIG. 12B. System 204 may be similar to system 190 of FIG. 13. However, the welding process described with respect to system 204 may be used with any other electrode fixtures described herein, such as electrode fixtures 80 or 130. In the example shown in FIG. 14, electrode fixture 206A and electrode fixture 206B are separated by spacer 208, which fixes the axial positioning between adjacent electrode fixtures 206A, 206B.

When electrode fixture 206B was positioned on lead structure 209, the distal end of conductor 216 was positioned or placed within attachment area 216. Conductor 216 may rest on the notch of weld tab 212 (e.g., notch 178 of weld tab 176A in FIG. 12B). In this position, conductor 216 may be welded to weld tab 212. Because weld tab 212 may be formed to provide a notch below the surface of electrode assembly 210, conductor 216 may be completely covered with the lead body after injection molding (or other lead body formation technique) is complete. This type of weld may be a different type of weld than that the edge weld described with respect to FIGS. 8 and 9.

Figure 15:
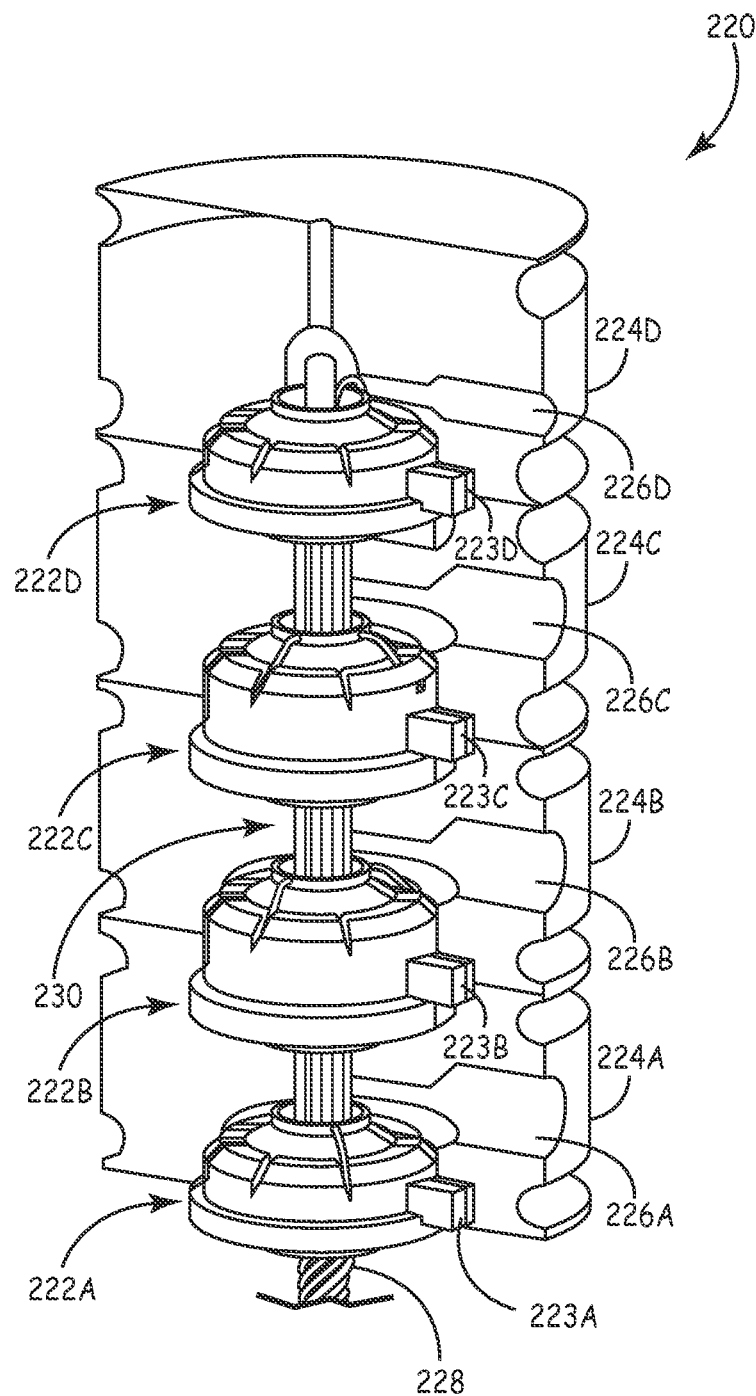
FIGS. 15 and 16 are partial perspective and cross-sectional views, respectively, of an example system for fabricating a lead that includes electrode fixtures and spacer housings for aligning the electrode fixtures and molding the lead body.
Figure 16:
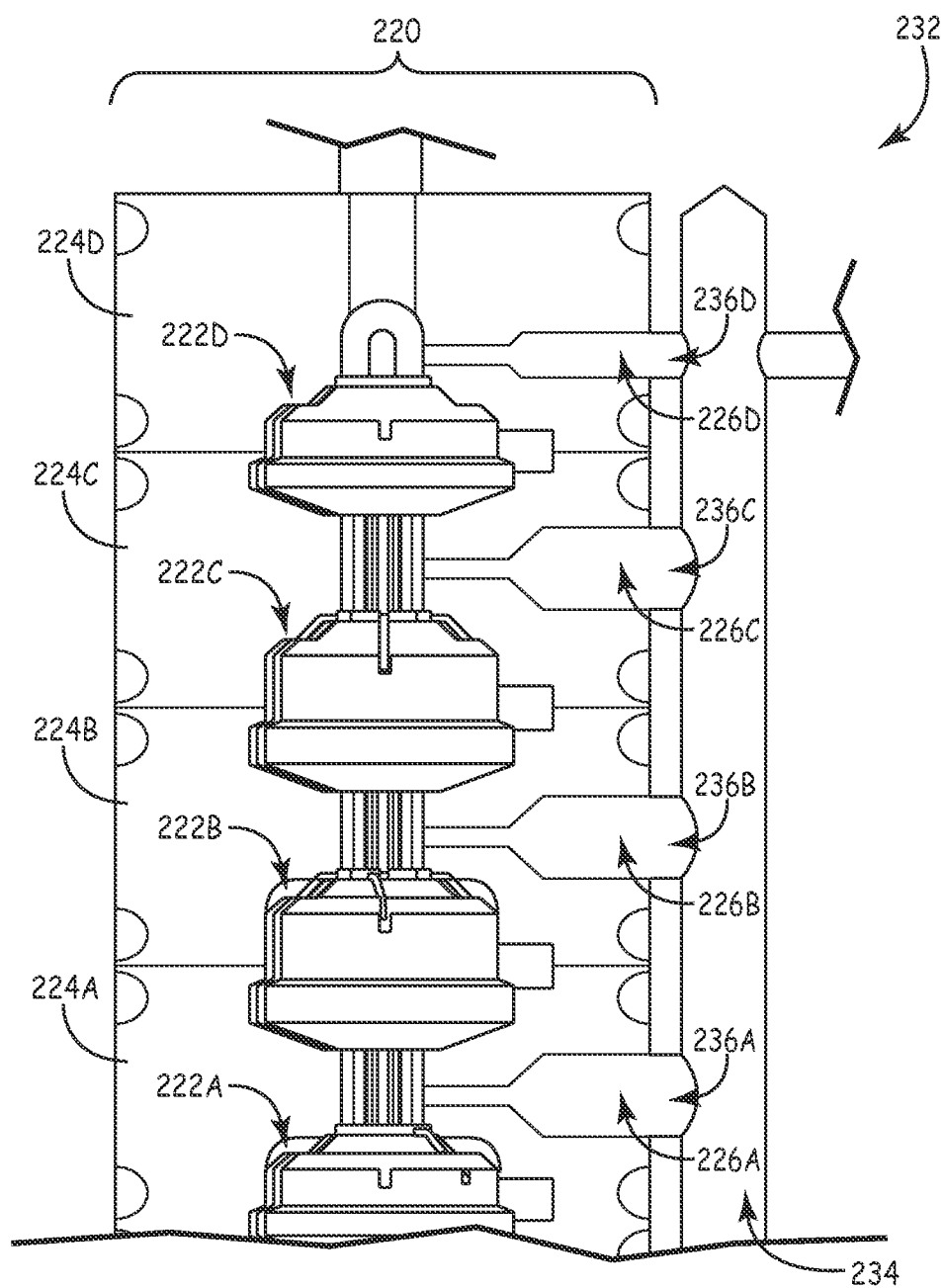

FIGS. 15 and 16 are partial perspective and cross-sectional views of example lead fabrication system 220 for fabricating a lead that includes electrode fixtures 222 and spacer housings 224. Spacer housings 224 may align electrode fixtures 222 and provide cavities for molding the lead body. Lead fabrication system 220 may be similar to system 190 of FIG. 13. However, each of spacer housings 224A, 224B, 224C, and 224D (collectively "spacer housings 224") may be configured to circumferentially and/or axially align electrode fixtures 222A, 222B, 222C, and 222D (collectively "electrode fixtures 222"). Each of electrode fixtures 222 may be configured to retrain an electrode assembly.

As shown in FIG. 15, each of electrode fixtures 222 may partially mate to two of spacer housings 224. For example, electrode fixture 222D mates with adjacent spacers 224C and 224D. Spacer 224C may thus axially align electrode fixture 222D to electrode fixture 222C. In addition, each of electrode fixtures 222 may include a respective registration structure 223A, 223B, 223C, and 223D (collectively "registration structures 223"). Each registration structure 223 may be configured to register to a slot within one or more spacer housings 224. When a registration structure 223 of an electrode fixture 222 is mated with a slot of an adjacent spacer housing 224, the electrode fixture 222 may be fixed in a particular circumferential position relative to the spacer housing 224 and, in some examples, the lead structure. In this way, registration structures 223 may be used to circumferentially align or register electrode fixtures 222 to each other.

Only a cross-section of spacer housings 224 is shown in FIG. 15. Each spacer housing 224 may be a generally cylindrical structure in some examples, although other configurations of housings are contemplated. Electrode fixtures 222 and spacer housings 224 may be sequentially stacked along the longitudinal axis of and around the lead structure (not shown) and conductors 228. Not only may spacer housings 224 provide and fix an axial alignment between electrode fixtures 222 and, therefore, between the respective electrode assemblies retained by electrode fixtures 222, but spacer housings 224 may also be configured to direct the flow of molding material (e.g., injection molding material) to form the lead body while electrode fixtures 222 are retaining the electrode assemblies. For example, as shown in FIG. 15, each of spacer housings 224 may include respective mold channels 226A, 226B, 226C, and 226D.

As shown in FIG. 16, molding system 232 includes lead fabrication system 220. Injection channel 234 may be in fluid communication with openings 236A, 236B, 236C, and 236D. Injection channel 234 may be defined by tubing, a rigid structure, or injection molding block that mates to spacer housings 224. Openings 236A, 236B, 236C, and 236D may be defined by the interface between spacer housings 224, tubing, or any other structure that allows for a polymer or other substance to flow from injection channel 234 to spacer housings 224. Each of openings 236A, 236B, 236C, and 236D may be in fluid communication with respective mold channels 226A, 226B, 226C, and 226D of spacer housings 224. In this manner, injection mold material (e.g., a polymer) may flow from injection channel 234 and into each respective mold channels 226A, 226B, 226C, and 226D to form portions of a lead body within spacer housings 224. Spacer housings 224 and electrode fixtures 222 may then be removed from the completed lead.

Figure 17:
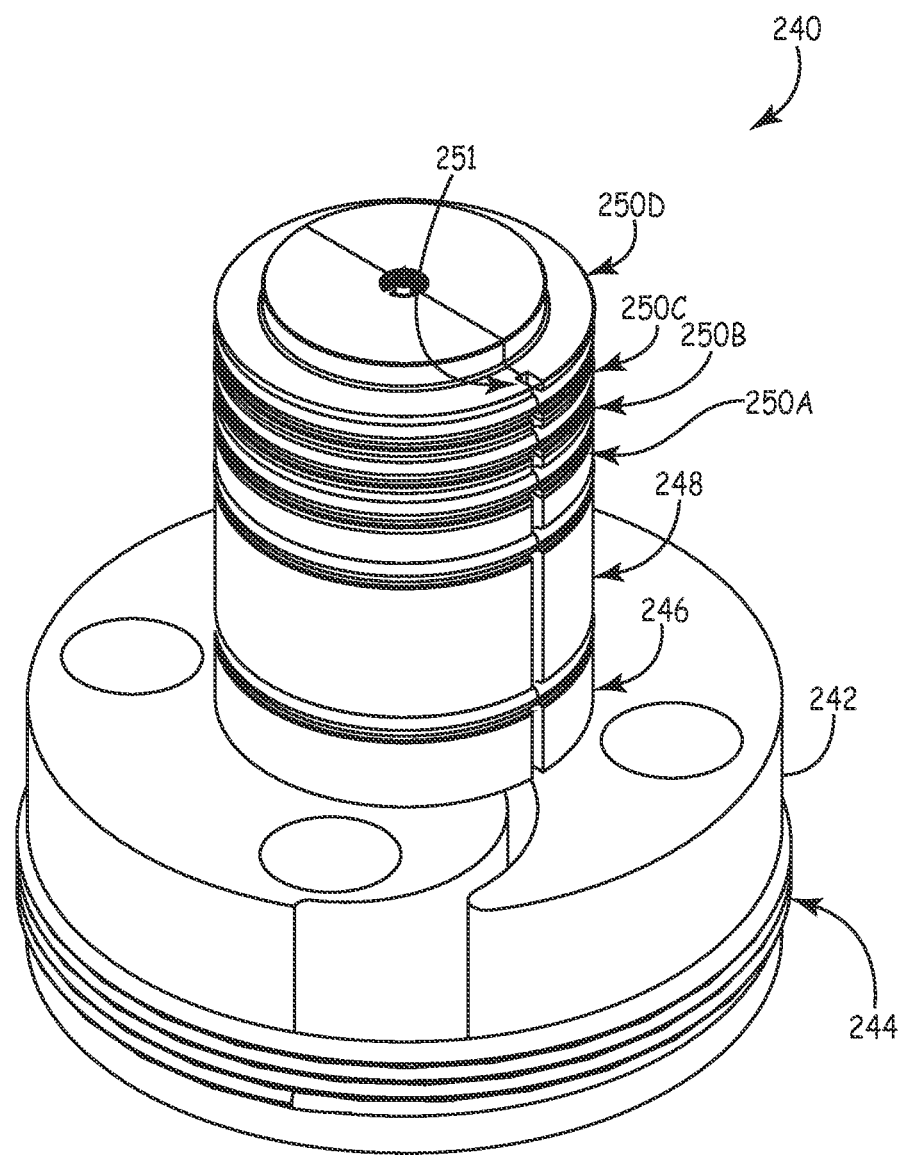
FIG. 17 is a perspective view of an example system for fabricating a lead with a plurality of stacked electrode fixtures.
Figure 18:
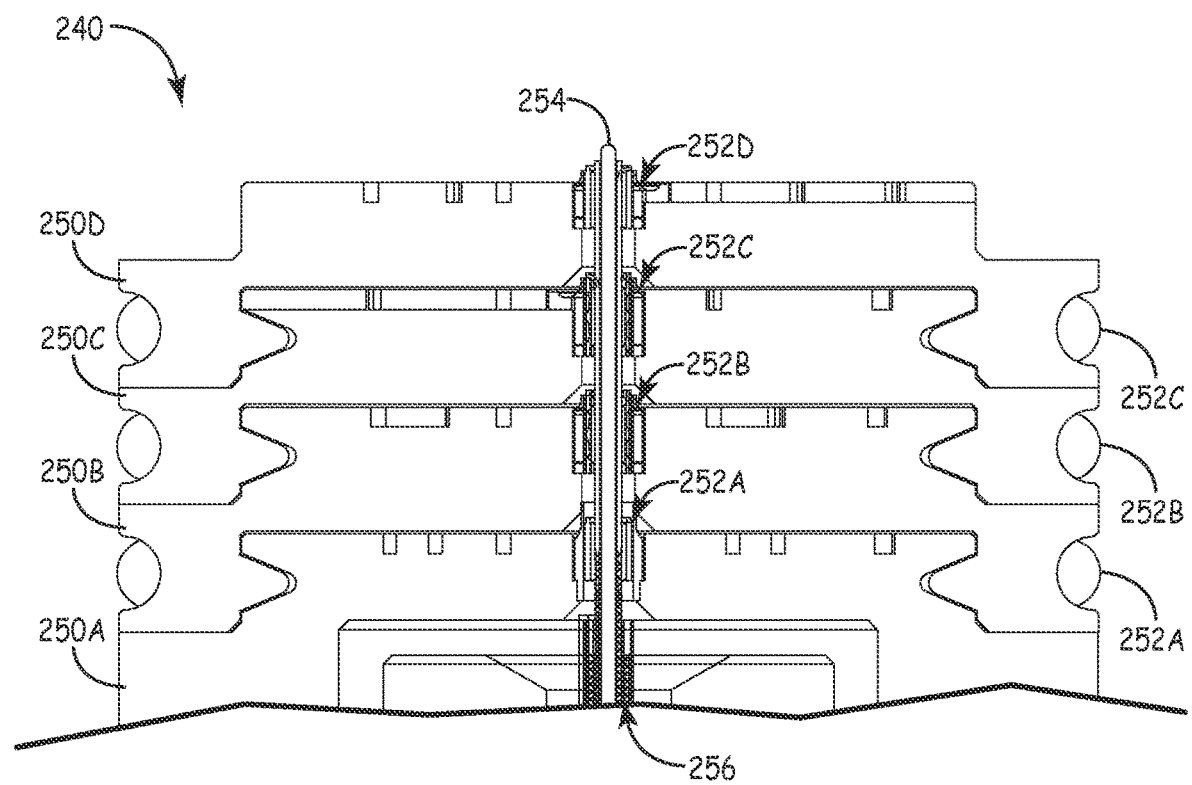
FIG. 18 is a cross-sectional view of the example system of FIG. 17.

Although FIGS. 15 and 16 illustrate one example of spacer housings that may facilitate both axial and/or circumferential alignment of electrode fixtures and injection molding of the lead body, other structures may be used for similar lead fabrication. For example, FIG. 17 is a perspective view of example system 240 for fabricating a lead with a plurality of stacking spacers 250. System 240 may include electrode fixtures, electrode assemblies, and any other lead components within stacking spacers 250. FIG. 18 illustrates an example cross-section of a portion of system 240. As shown in FIG. 17, fabrication base 242 may include a circumferential groove to retain proximal portion of lead 244 wrapped around fabrication base 242. The wrapped portion of lead 244 may include coiled conductors and/or a lead structure that supports the conductors. In other examples, the wrapped portion of lead 244 may already include an injection molded lead body. However, the portion of lead 244 that includes the electrodes within spacers 250 may not have the lead body formed yet. System 240 may also include proximal spacers 246 and 248 that provide axial alignment for spacers 250A, 250B, 250C, and 250D (collectively "spacers 250").

Spacers 250 may axially align electrode fixtures that each retain respective electrode assemblies and function to channel injection mold material to the lead structure to form the lead body. Spacers 250 may thus contact each other for provide axial alignment for the electrode fixtures. In addition, spacers 250 each define slot 251 to circumferentially align each of the electrode fixtures and their retained electrode assemblies.

FIG. 18 is a cross-sectional view of example system 240. As shown in FIG. 18, each of spacers 250 includes a distal surface and a proximal surface for contacting adjacent spacers. Spacers 250 may each also include o-ring 252A, 252B, or 252C (collectively "o-rings 252"). O-rings 252 may seal spacers 250 within a cylinder when injection molding the lead body.

Spacers 250 are positioned around lead structure 254 and conductors 256. In addition, each of spacers 250 are configured to contact and align one of electrode fixtures 252A, 252B, 252C, and 252D. Each of electrode fixtures 252 may be configured to fit within a channel defined by a respective spacer 250. Each of electrode fixtures 252 may also include a registration structure to circumferentially align the electrode fixture 252 within the respective spacer 250. Spacers 250 may generally be shaped as disks, but other shapes are also contemplated.

Figure 19:
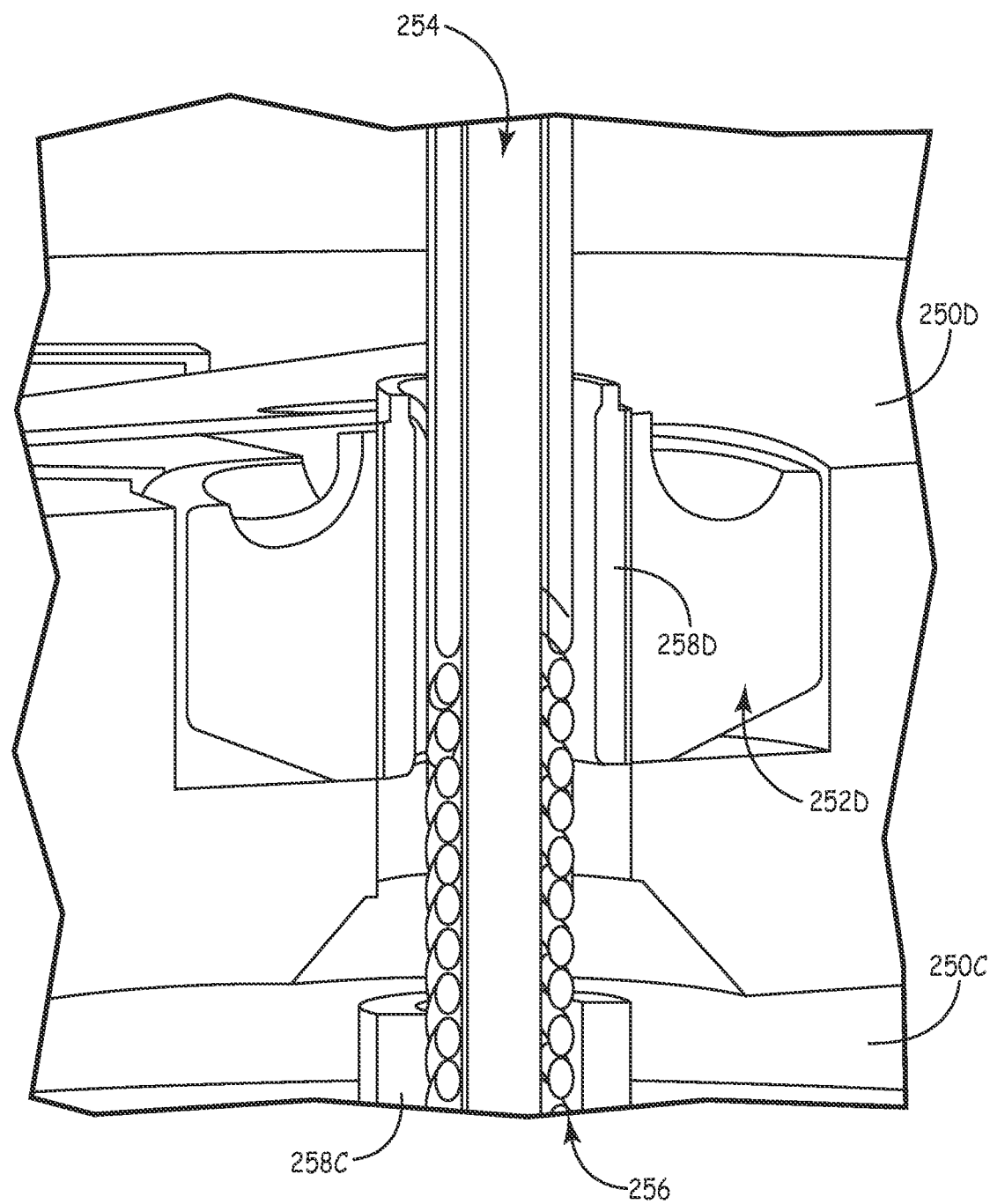
FIG. 19 is a cross-sectional view of an example electrode fixture of the example system of FIG. 17.

FIG. 19 is a cross-sectional view of example electrode fixture 250D of example system 240. As shown in FIG. 19, spacer 250D is positioned around lead structure 254, conductors 256, and electrode fixture 252D. Electrode fixture 252D may also retain electrode assembly 258B. Electrode fixture 252D may contact spacer 250D such that electrode fixture 252D is fixed in a known axially and circumferentially position within spacer 250D. Spacer 250D may also fix the axial distance between electrode fixtures 252D and 252C and electrode assemblies 258D and 258C. In other examples, spacer 250D and electrode fixture 252D may be a single structure to reduce the number of parts needed in system 240.

Figure 20:
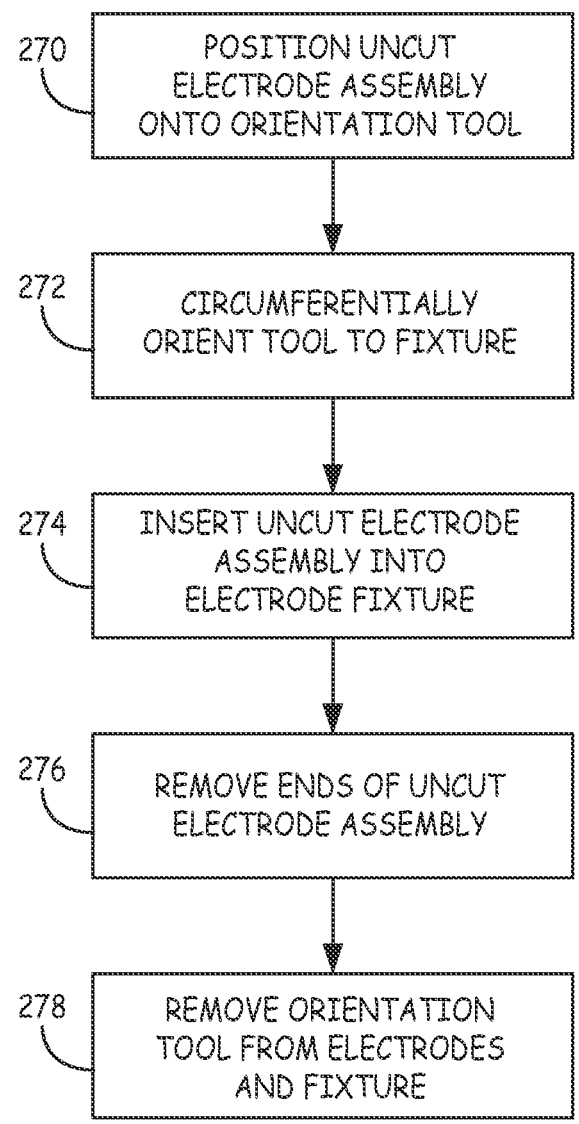
FIG. 20 is a flow diagram of an example process for retaining an electrode assembly within an electrode fixture.

FIG. 20 is a flow diagram of an example process for retaining an electrode assembly within an electrode fixture. Although the process of FIG. 20 will be described with respect to electrode assembly 50, orientation tool 70, and electrode fixture 80, any of the electrode assemblies (e.g., electrode assemblies 150, 170, 308, 350, and 394) and electrode fixtures (e.g., electrode fixtures 80, 200, 206, 222, 250, 306, 348, and 392) described herein may be used in other examples.

As shown in FIG. 20, the fabrication process for a lead with multiple electrodes (e.g., segmented ring electrodes) may begin with an uncut electrode assembly 50. As described herein, the uncut electrode assembly 50 may include electrode portions 52 and 54 that will eventually be cut into individual electrodes and proximal and distal portions 56 and 58. Generally, electrode assembly 50 may only include electrodes at a single axial position (e.g., a single electrode level). However, in other examples, an electrode assembly may include two electrode levels or electrodes at different axial positions and, possibly, at the same circumferential position. An operator (e.g., a human or an automated or semi-automated machine) may position uncut electrode assembly 50 onto shaft 76 of orientation tool 70 (270). In some examples, groove 74 of orientation tool 70 may be used to circumferentially orient shaft 76 to electrode assembly 50. Next, the operator may circumferentially orient orientation tool 70 to electrode fixture 80 (272). The operator may align groove 74 or another registration mark of orientation tool 70 to electrode fixture 80 (272). The operator may then insert uncut electrode assembly 50 into channel 88 of electrode fixture 80 (274). Electrode assembly 50 may be mated to an inner surface of electrode fixture 80 by a friction fit or other coupling technique.

Once electrode assembly 50 is retained within electrode fixture 80, the operator may remove the ends of electrode assembly 50, e.g., proximal portion 56 and distal portion 58, from the remaining electrodes (276). Removal of proximal portion 56 and distal portion 58 from the central portion of electrode assembly 50 may require cutting the metal of electrode assembly 50. A laser cutter or other precision cutting tool may be used to perform this step. The operator may then remove shaft 76 of orientation tool 70 from electrode assembly 50 within electrode fixture 80.

The process of FIG. 20 may be performed for each electrode assembly (e.g., electrode level) to be included in the final lead. In some examples, electrode assembly 50 may not need to have distal and/or proximal portions removed after inserting into electrode fixture 80. For example, a single circumferential electrode or segmented ring electrodes with additional bracing may not require the extra material to be removed during the fabrication process described herein.

Figure 21:
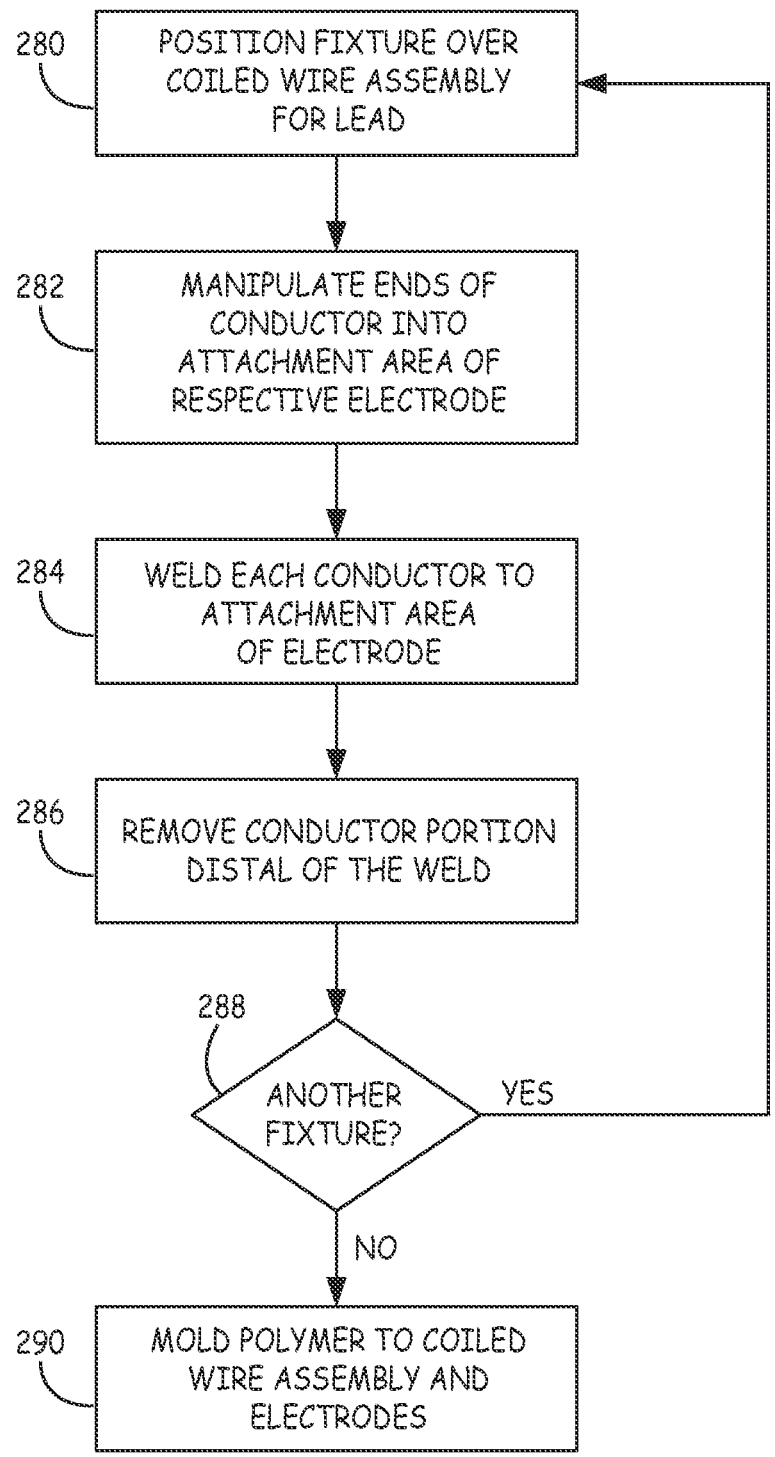
FIG. 21 is a flow diagram of an example process for coupling electrodes to respective conductors and molding the lead body.

FIG. 21 is a flow diagram of an example process for coupling electrodes to respective conductors and molding the lead body. Although the process of FIG. 21 will be described with respect to electrode assembly 150 and electrode fixtures 130 (FIGS. 8-10), any of the electrode assemblies (e.g., electrode assemblies 150, 170, 308, 350, and 394) and electrode fixtures (e.g., electrode fixtures 80, 200, 206, 222, 250, 306, 348, and 392) described herein with respective systems 132, 190, 232, 240, 300, 340, and 380 may be used in other examples. For example, spacers may be used to axially align electrode fixtures instead of the electrode fixtures directly contacting each other. The process of FIG. 21 may be an extension of the process of FIG. 20 and may, e.g., be performed after the process of FIG. 20 is complete.

An operator may begin by positioning electrode fixture 130A over the coiled wire assembly (e.g., lead structure 124 and conductors 122) for the lead (280). Positioning electrode fixtures 130 may include circumferentially aligning a registration structure to other electrode fixtures 130. The operator may then manipulate or place the distal end of one or more conductors into an attachment area of the respective electrode of electrode assembly 150 (282). Once the conductors are positioned in the respective attachment areas, the operator may weld each conductor to the attachment area of the respective electrode (284). Each attachment area may be defined by a portion of an electrode of electrode assembly 150 (e.g., weld portion 160 or weld tab 176A). The operator may then remove any conductor portion that remains distal of the weld (286).

If there are additional electrode fixtures 130 to be added to the lead ("YES" branch of block 288), the operator may then position and register a subsequent electrode fixture 130 directly in contact with the previous electrode fixture (280). If all electrode fixtures have been added to the lead ("NO" branch of block 288), the operator may mold a lead body material (e.g., a polymer) to the coiled wire assembly and the welded electrodes (290).

In other examples, the process of FIG. 21 may require that all electrode fixtures are positioned and registered prior to welding any conductors to respective electrodes. In alternative examples in which spacers are used to axially align each electrode fixture, the operator may place a spacer between each consecutive electrode fixture on the lead structure. In some examples, electrode fixtures 130 may be removed from the lead assembly prior to molding the lead body.

Figure 22:
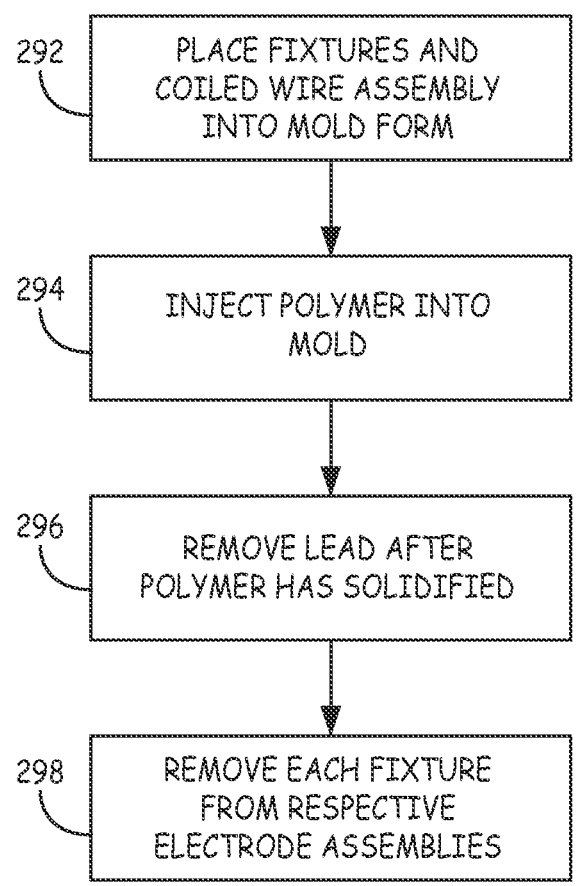
FIG. 22 is a flow diagram of an example process for molding the lead body prior to removing the electrode fixtures from each electrode assembly.

FIG. 22 is a flow diagram of an example process for molding the lead body prior to removing electrode fixtures 130 from each electrode assembly. Although the process of FIG. 22 will be described with respect to electrode assembly 150 and electrode fixtures 130 of system 132, any of the electrode assemblies (e.g., electrode assemblies 150, 170, 308, 350, and 394) and electrode fixtures (e.g., electrode fixtures 80, 200, 206, 222, 250, 306, 348, and 392) described herein with respective systems 132, 190, 232, 240, 300, 340, and 380 may be used in other examples. The process of FIG. 22 may be an extension of the process described in block 290 of FIG. 21.

As shown in FIG. 22, the operator may place electrode fixtures 130 and the coiled wire assembly (e.g., system 132) into mold form 142 (292). The operator may then begin to introduce (e.g., via injection) the polymer, or material, into mold form 142 (294). The injected material may surround any exposed portions of conductors 122, welds, and lead structures. Mold form 142 may be configured and the injected material may be directed so as not to cover any external portions of electrodes. Once the polymer has solidified or cured, the operator may remove system 132 and the attached polymer lead body from mold form 142 (296).

The operator may then remove each electrode fixture 130 from the respective electrode assemblies of the lead (298). As described herein, each of the electrode fixtures 130 may include opposing circumferential removal surfaces to which opposing circumferential forces can be applied. These opposing forces may cause the electrode fixture to fracture, break, snap, or otherwise disengage from the lead. These removal forces may be applied to multiple circumferential and/or axial locations on the electrode fixtures (e.g., electrode capture portion 82 and/or collar 86). In some examples, the removal surfaces may also be the surfaces that define a registration structure (e.g., registration structures 92A, 92B, 94A, and 94B).

Figure 23:
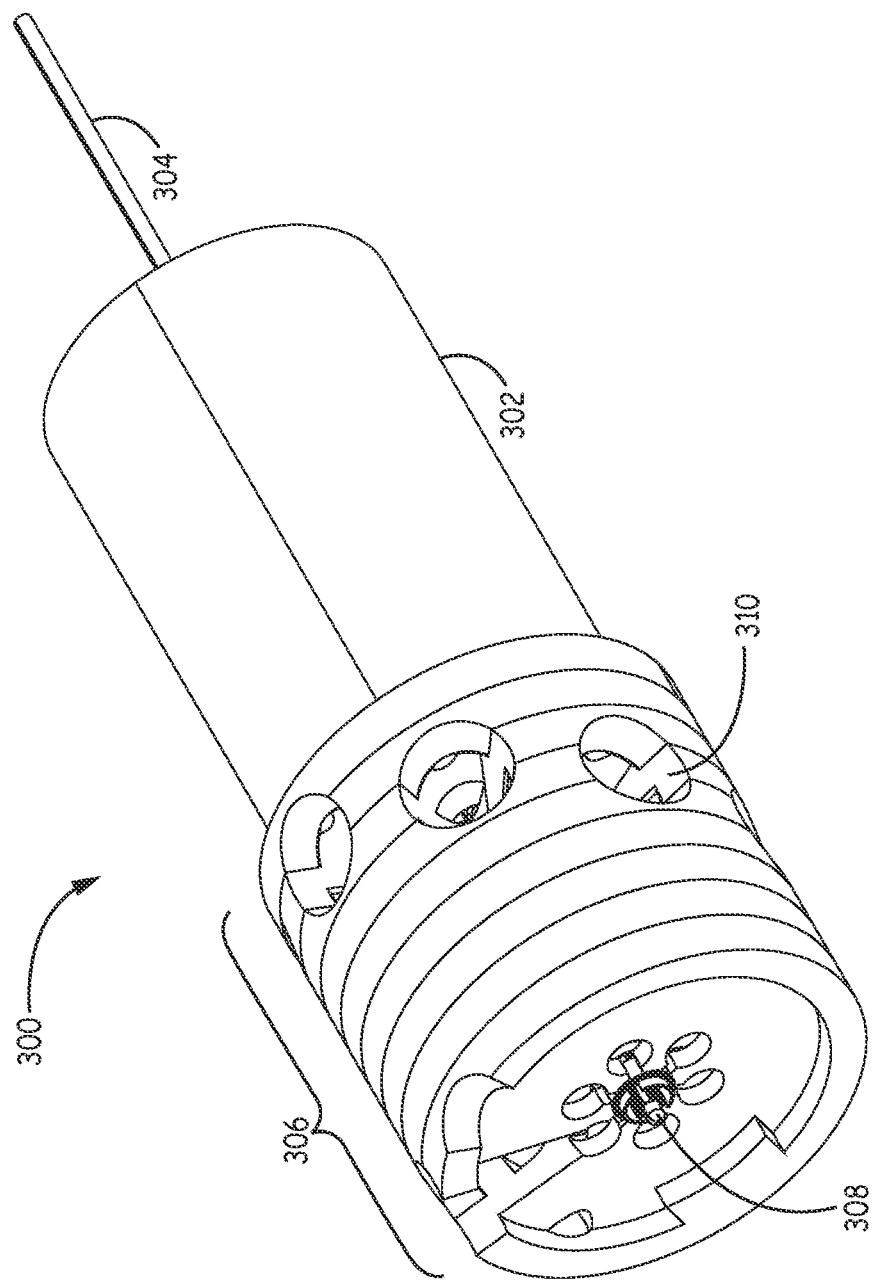
FIG. 23 is a perspective view of an example system for fabricating a lead that includes electrode fixtures configured as stackable disks to axially and rotationally align electrodes about conductors of a lead.

FIGS. 23 through 27B illustrate an example system 300 and its components configured to facilitate construction of a medical lead including a plurality of electrodes. FIG. 23 is a perspective view of an example system 300 for fabricating a lead that includes electrode fixtures configured as stackable disks to axially and rotationally align electrodes about conductors of a lead. System 300 may be functionally similar to system 132 of FIGS. 9 and 10, such that system 300 comprises a plurality of electrode fixtures 306 configured to be stacked together to axially and circumferentially align the electrode assemblies retained by the respective electrode fixtures 306.

As shown in FIG. 23, system 300 includes support structure 302, lead body 304, eight electrode fixtures 306, and lead structure 308. Lead body 304 may surround a plurality of conductors (not shown in FIG. 23) to be electrically coupled to respective electrode assemblies within electrode fixtures 306. Support structure 302 may be constructed as a cylinder having a distal plate configured to mate with the proximal one of electrode fixtures 306. Each of electrode fixtures 306 may be configured to retain a respective electrode assembly (not shown in FIG. 23), such as electrode assemblies 150 or 170 of FIGS. 12A and 12B, or any other electrodes or electrode assemblies described herein. Each of electrode fixtures 306 may be configured to mate to adjacent electrode fixtures within a predetermined axial and circumferential position.

Lead structure 308 may be configured to retain at least a portion of each of the plurality of conductors of the medical lead to be formed. Each of electrode fixtures 306 may be fitted with an electrode assembly and sequentially positioned around the lead structure 308 and at least one of the plurality of conductors. In this manner, the plurality of conductors may reside generally near a longitudinal center axis of electrode fixtures 306 and support structure 302 that corresponds to lead body 304.

When each of electrode fixtures 306 is positioned around the conductors and in contact with adjacent one or more electrode fixtures, each of electrode fixtures 306 are circumferentially aligned to each other. This circumferential alignment also circumferentially aligns the electrode assemblies retained within the respective electrode fixture 306 to at least one conductor. Lead structure 308 may be provided within electrode fixtures 306 to hold or maintain the position of the plurality of conductors, but lead structure 308 may not be required in other examples.

In addition, access ports 310 are formed through a subset of electrode fixtures 306 to facilitate physical access from outside of electrode fixtures 306 to an interior perimeter within the electrode fixtures. Each of access ports 310 may be configured to provide access to a welding mechanism or energy source that electrically couples a conductor to a portion of the electrode assembly retained within electrode fixtures 306. In the example of FIG. 23, three adjacent electrode fixtures 306 define respective cut-out portions that, when circumferentially aligned, form one of access ports 310. The middle of the three adjacent electrode fixtures 306 may define the largest cut-out portion that extends through the entire radial section of the electrode fixture, while the two adjacent electrode fixtures may define respective cut-out portions that only extend partially through the radius of the respective electrode fixture. Although access ports 310 are illustrated as a cone-shaped port, other access ports 310 may be defined as cylinders, rectangles, pyramids, or any other shapes that facilitate access to the electrode assemblies.

In other examples, as few as two or even one electrode fixture may define a single access port 310. In some examples, four or more electrode fixtures 306 may combine to define a single access port 310. In addition, other examples of system 300 may include electrode fixtures that combine to form single access ports configured to provide access to two or more electrode-conductor connections.

Although system 300 may include eight electrode fixtures 306, other systems may include fewer or greater electrode fixtures to facilitate the construction of medical leads with fewer or greater electrode assemblies. Each of electrode fixtures 306 may be fitted with a respective electrode assembly using any technique described herein, such as the techniques described with respect to FIGS. 4A, 4B, 5A, 5B, and FIG. 20.

Electrode assemblies may be electrically coupled to the respective conductors before the next, more distal, electrode fixture and electrode assembly is added to support structure 302. In other examples, the electrode assemblies may be electrically coupled to the respective conductors only once all electrode fixtures 306 are in place in system 300. In any example, electrode fixtures 306 may be removed from the electrode assemblies by fracturing the electrode fixtures along a preformed perforation or radial channel, cutting each electrode fixture off, or otherwise removing the electrode fixtures (e.g., according to the examples of FIG. 22).

Figure 24:
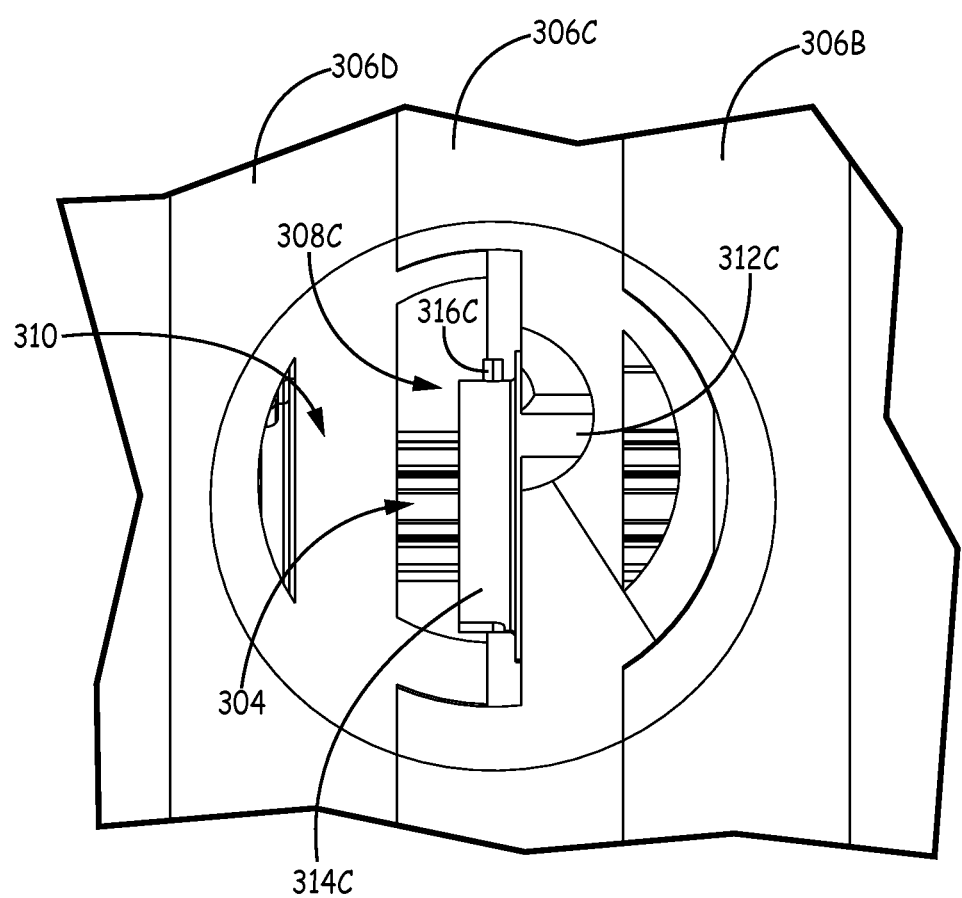
FIG. 24 is a plan view of an access port formed by a plurality of electrode fixtures of the system of FIG. 23.

FIG. 24 is a plan view of access port 310 formed by a plurality of electrode fixtures 306 of system 300 illustrated in FIG. 23. As shown in FIG. 24, electrode fixtures 306B, 306C, and 306D form access port 310 with cut-away portions from each of the respective electrode fixtures. Electrode fixtures 306B and 306D each define a respective cut-away portion forming edges of access port 310 through an outer portion of the respective electrode fixture. Electrode fixture 306C defines a cut-away portion forming a middle portion of access port 310 that extends through the entire radial section of electrode fixture 306C, from the radially external surface through the radially internal surface.

Access port 310 facilitates access through electrode fixtures 306 such that conductor 316C can be electrically coupled (e.g., welded, soldered, or otherwise attached) to electrode assembly 308C. Access port 310 may facilitate access to electrode assembly 308C at a substantially orthogonal (e.g., orthogonal or nearly orthogonal) angle with respect to lead structure 304. Electrode fixture 306C defines an inner channel within which electrode assembly 308C is fitted to electrode fixture 306C. Electrode fixture 306C may be configured to contact electrode 312C such that attachment area 314C of electrode assembly 308C is accessible through access port 310. Conductor 316C may be one of a plurality of conductors of the medical lead being constructed. Conductor 316C may be held at least partially in place by lead structure 304 also positioned within electrode fixtures 306. Conductor 316C may be positioned at or near attachment area 314C.

Electrode fixtures 306 may be configured such that, when each electrode fixture 306 is registered to each other, the cut-away portions of adjacent electrode fixtures 306B, 306C, and 306D define access port 310 to expose attachment area 314C of electrode assembly 314C and respective conductor 316C. Through access port 310, a laser welding beam, soldering mechanism, or any other means for electrically coupling conductor 316C to attachment area 314C.

Access port 310 may provide access to a single conductor and electrode, such as conductor 316C and electrode assembly 308 retained by electrode fixture 306C. In other examples, access port 310 may be defined by two or more electrode fixtures 306 and provide access to an electrode assembly retained by an electrode fixture that does not define a portion of the access port. In other words, the access port 310 may be defined at a non-orthogonal angle to the longitudinal central axis of electrode fixtures 306. In some examples, access port 310 may be defined from two electrode fixtures 306 or four or more electrode fixtures. In other examples, a single electrode fixture may define an access port that facilitates access to the electrode assembly retained by the single electrode fixture or an electrode assembly retained by an adjacent electrode fixture.

FIGS. 25 and 26 are perspective views of an example support structure 302 and electrode fixtures 306 stacked together to form the example system of FIG. 23. As shown in FIG. 25, support structure 302 may be used to support conductors 316, lead structure 318, and the electrode fixtures configured to align the respective electrode assemblies to the respective conductors 316. Each of the plurality of conductors 316 may be mated to a portion of lead structure 318 such that each of conductors 316 is formed to a respective circumferential position. The distal end of each of conductors 316 may be bent away from lead structure 318, as shown in the example of FIG. 25, to facilitate coupling with the respective electrode assembly.

Support structure 302 may be constructed as a cylinder defining a channel through which conductors 316 may be placed. Support structure 302 may also include base plate 322 that is configured to mate with a proximal surface of the first electrode fixture to be stacked onto support structure 302. Base plate 322 may also define registration structure 320, where registration structure 320 is configured to mate with a registration slot defined by a proximal surface of the first electrode fixture. Registration, or mating, between registration structure 320 and the registration slot defined by the first electrode fixture may function to circumferentially align the electrode fixture (and the electrode assembly retained by the electrode fixture) to support structure 302 and conductors 316. In other examples, one or more pairs of registration structures and slots, detents and indents, or any other features between base plate 322 and the mating electrode fixture may be used to circumferentially align the electrode fixture to support structure 302.

As shown in FIG. 26, two electrode fixtures 306A and 306B have been stacked together and aligned with support structure 302 of FIG. 25. Each of electrode fixtures 306A, 306B, and additional electrode fixtures 306 may be moved towards base plate 322 of support structure 302 in the direction of arrow 324. Each of electrode fixtures 306 may retain an electrode assembly, such as electrode assembly 308B retained within an interior surface of electrode fixture 306B. As each of electrode fixtures 306 are subsequently mated to the previously stacked electrode fixture, the newly added electrode fixture is circumferentially registered to the previously added electrode fixture. In this manner, electrodes fixtures 306 are circumferentially and axially registered and aligned to each other via features of fixtures 306. For example, electrode fixture 306B is circumferentially aligned to electrode fixture 306A. In other words, the registration between electrode fixtures 306A and 306B may fix an axial distance and a circumferential position between electrode fixtures 306A and 306B.

Figure 27A:
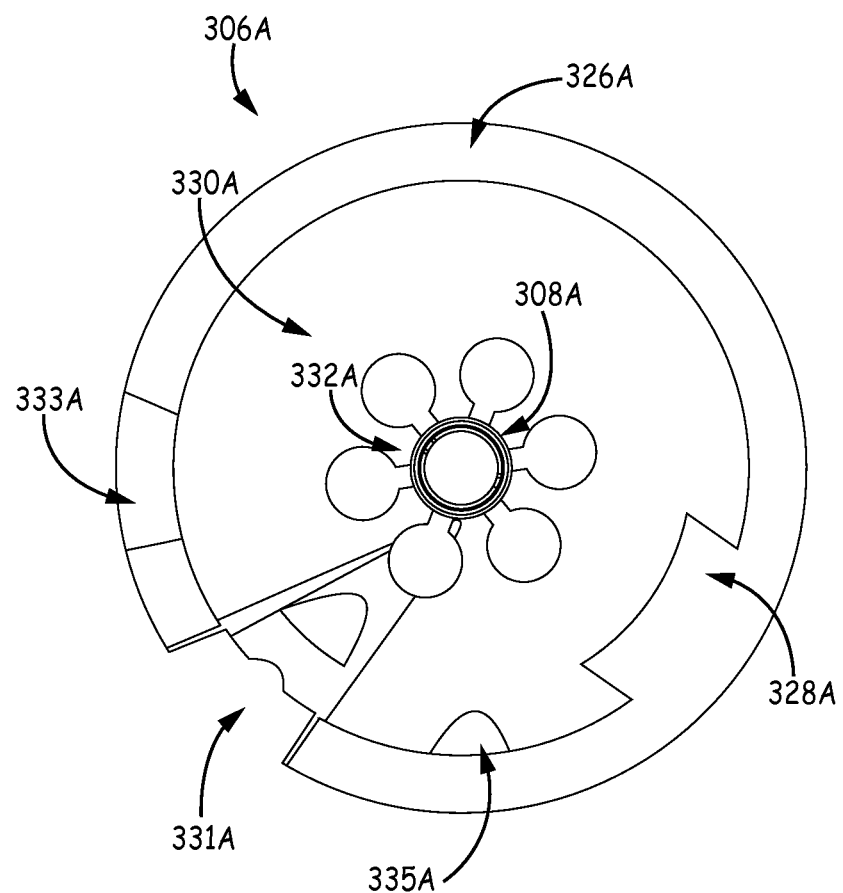
FIGS. 27A and 27B are front and back views of an example electrode fixture of the system of FIG. 23.
Figure 27B:
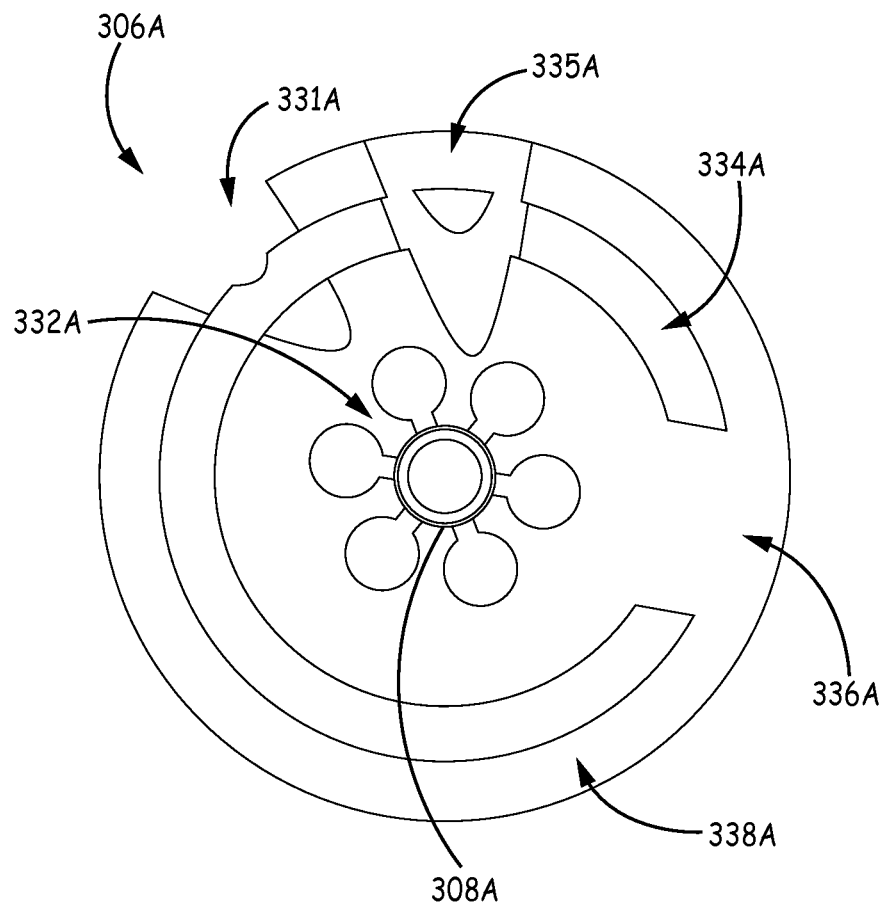

Each of electrode fixtures 306 may be identical in structure and dimensions. In other words, each of electrode fixtures 306 may be constructed to be interchangeable. As shown in FIGS. 27A and 27B, the registration structure of the distal surface may be offset with the registration slot of the proximal surface such that stacking of identical electrode fixtures 306 may cause a predetermined circumferential position shift that aligns two or more cut-out portions that each form at least a portion of a respective access port. Each electrode fixture may have a circumferential shift that matches the shift of each successively distal conductor such that the electrode assembly retained by each electrode fixture is oriented to the respective conductor. In other examples, each of electrode fixtures 306 may be constructed with different dimensions or defined structures such that each electrode fixture is constructed to fit in a specific position along the plurality of conductors and within system 300.

The method of constructing system 300, and the medical lead may include steps similar to the method of FIG. 21. For example, conductors 316 and lead structure 318 may be positioned within the channel defined by support structure 302. Electrode fixture 306A, with an electrode assembly retained within a channel defined by electrode fixture 306A, is positioned at least partially around the respective conductor and the other plurality of conductors of the lead. The proximal surface of electrode fixture 306A is then mated and registered to the distal surface of base plate 322. This process may be repeated for each of the electrode fixtures 306 to be added to system 300, where each subsequent electrode fixture 306 is mated and registered to another electrode fixture 306. When the electrode fixtures 306 are all in place with respect to the respective conductors and the electrode assemblies are retained by the respective electrode fixture, each conductor may be electrically coupled (e.g., welded or soldered) to a portion of the respective electrode assembly (e.g., the attachment area).

After the conductors are coupled to the respective electrode assemblies, support structure 302 and the electrode fixtures may be removed from the lead. Support structure 302 may be removed from the proximal portion of the lead in the direction of arrow 324 of FIG. 26, and electrode fixtures 306 may be removed from each respective electrode assembly. Electrode fixtures 306 may be fractured and broken along a perforated plane, in some examples. For example, a removal tool may be placed within each of access ports 310, and jaws of the removal tool may open within the access port such that the electrode fixture fractures or an inner radius of the electrode fixture expands and separates from the respective electrode assembly.

In some examples, the lead body may be molded around the electrode assemblies and conductors after electrode fixtures 306 have been removed. In other examples, the lead body may be molded around the electrode assemblies and conductors while electrode fixtures 306 may still retain the respective electrode assemblies (e.g., as described with respect to FIG. 22).

FIGS. 27A and 27B are distal and proximal views, respectively, of an example electrode fixture 306A of system 300 of FIG. 23. Electrode fixture 306A and electrode assembly 308A may be substantially similar (e.g., similar or nearly similar) to other electrode fixtures 306 and electrode assemblies 308 of system 300. However, in other examples, at least two or even all of the electrode fixtures 306 may be configured differently to achieve circumferential alignment of electrode assemblies 308 within system 300.

As shown in FIG. 27A, electrode fixture 306A defines a distal surface 330A. Distal surface 330A also defines rim 326A which is raised from the radially inward portion of distal surface 330A, as illustrated in FIGS. 23 and 26. Rim 326A may also define registration structure 328A that is configured to mate, or register, with a registration slot defined by the proximal surface of another electrode fixture. Registration structure 328A may circumferentially orient or align electrode fixture 306A to another electrode fixture.

Electrode fixture 306A may also define an inner channel within which electrode assembly 308A is fitted. Retaining members 332A may be provided at six different locations around the center of electrode fixture 306A, and electrode assembly 308A may contact the inner surface of each of retaining members 332A such that electrode fixture 306A at least partially retains electrode assembly 308A. In some examples, retaining members 332A may be referred to as an electrode capture portion of electrode fixture 306A. In some examples, fewer or greater than six retaining members 332A may be defined by electrode fixture 306A. In other examples, electrode fixture 306A may merely define an inner circular channel with a continuous cylindrical surface.

Electrode fixture 306A may further define one or more cut-out portions configured to at least partially define respective access ports, such as access port 310 of FIGS. 23 and 24. For example, electrode fixture 306A may define cut-out portions 331A, 333A, and 335A. Cut-out portion 331A may provide access to a portion of electrode assembly 308A for electrically coupling a portion of electrode assembly 308A to a respective conductor.

As shown in FIG. 27B, electrode fixture 306A also defines a proximal surface 338A opposite distal surface 330A. Proximal surface 338A defines collar 334A which is raised from the radially inward and radially outward portions of proximal surface 338A. Collar 334A defines registration slot 336A as a gap within collar 334A. Registration slot 336A may accept a registration structure (such as registration structure 328A of FIG. 26A) from a different electrode fixture or base plate 322 to circumferentially align the two electrode fixtures. FIG. 27B also illustrates the proximal surfaces of retaining members 332A and electrode 308A commonly illustrated in FIG. 27A. Proximal surface 338A is configured to mate with base plate 322 of support structure 320 of FIGS. 23, 25, and 26 or the distal surface of another electrode fixture 306. FIG. 27B also illustrates that electrode fixture 308A defines cut-out portions 331A and 335A to at least partially form respective access ports to at least electrode 308A.

FIG. 28 is a perspective view of an example system 340 for fabricating a lead that includes electrode fixtures 348 fitted within respective electrode assemblies 350 and including an arm to align the respective electrode assemblies about conductors 352 of a medical lead. System 340 may different from systems 132, 190, 232, 240, and 300 described herein in that system 340 comprises electrode fixtures 348 at least partially within respective electrode assemblies 350 whereas electrode fixtures of systems 132, 190, 232, 240, and 300 include electrode assemblies retained at least partially within respective electrode fixtures.

As shown in FIG. 28, system 340 includes conductors 352 of a to-be-constructed medical lead, support structure portion 342A, support structure portion 342B, electrode fixtures 348, and electrode assemblies 350. Support structure portion 342A includes registration arms 344A and 346A, and support structure portion 342B includes registration arms 344B and 346B. Registration arms 344A and 344B and registration arms 346A and 346B are configured to accept respective electrode fixtures 348 to axially and circumferentially align the respective electrode fixtures 348 and the respective electrode assemblies 350 retained thereon. Electrode assemblies 350 may be similar to electrode assemblies described herein, such as electrode assemblies 150, 170, or 308.

Each of support structure portions 342A and 342B may define a partial cylinder, such that a complete cylinder may be formed when support structure portions 342A and 342B are mated to each other as shown in FIG. 28. Each of registration arms 344A, 344B, 346A, and 346B extend in a distal direction from the respective support structure portions 342A and 342B. Although support portions 342A and 342B combine to form a cylinder, any other shapes such as cubes, rectangles, or any other shape may be used. The distal direction may be opposite of an end of the medical lead configured to attach to an IMD.

Figure 31A:
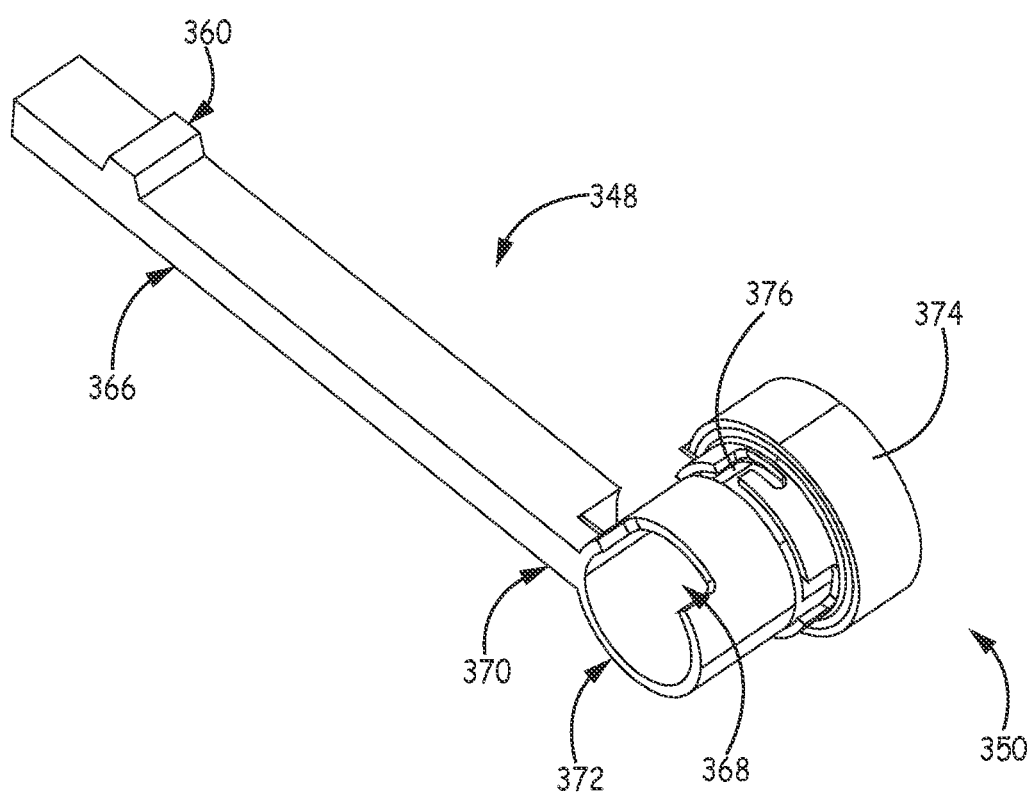
FIGS. 31A and 31B are perspective views of an example electrode and a respective electrode fixture of the system of FIG. 28.
Figure 31B:
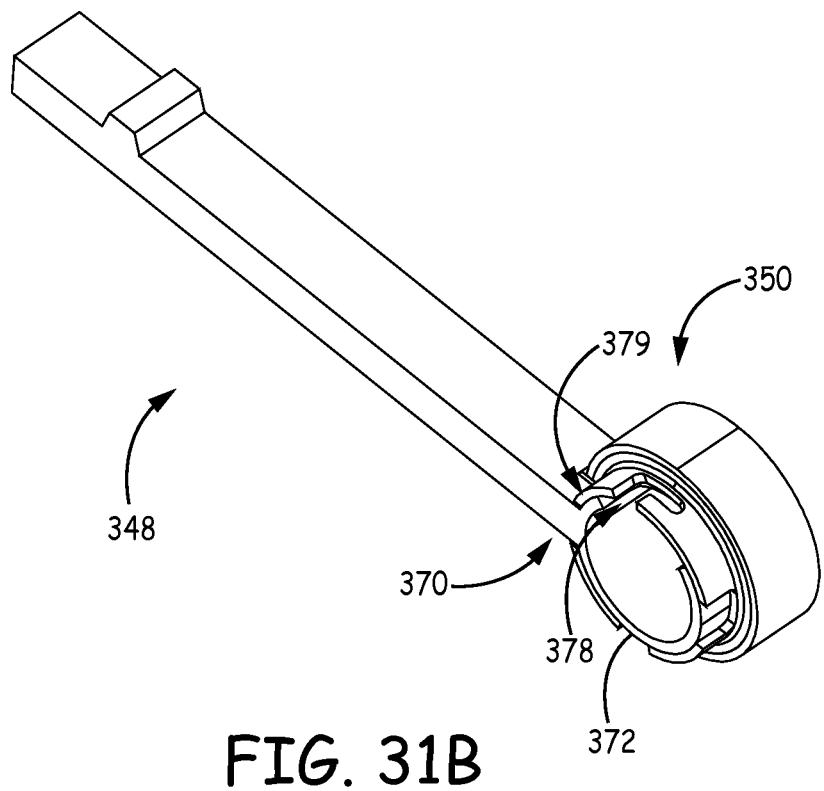

Each of electrode fixtures 348 defines a collar portion connected to an elongated member (e.g., an arm), both of which are illustrated in FIGS. 31A and 31B. At least a portion of the collar portion of each electrode fixture 348 is configured to be fitted within a channel defined by a respective electrode assembly 350. In this manner, the collar portion of each of electrode fixtures 348 may retain a respective electrode assembly 350. Once electrode fixtures 348 are retained within the respective registration arms 344A and 344B and registration arms 346A and 346B, electrode assemblies 350 may be axially and circumferentially aligned to respective conductors 352 such that each electrode assembly can be electrically coupled to the respective conductor.

A lead body may be molded around conductors 352 and electrode assemblies 350 to form a medical lead. Subsequent to molding the lead body around the plurality of conductors 352, the elongated member may be removed from the collar such that the collar portion of each electrode fixture 348 remains at least partially fitted within a channel defined by the respective electrode assembly 350. In this manner, the collar portion of electrode fixtures 348 may remain within a completed medical lead. In some examples, one or both of support structure portions 342A and 342B may be removed from electrode fixtures 348 prior to removing the elongated members from the respective collars of each electrode fixture.

Figure 29:
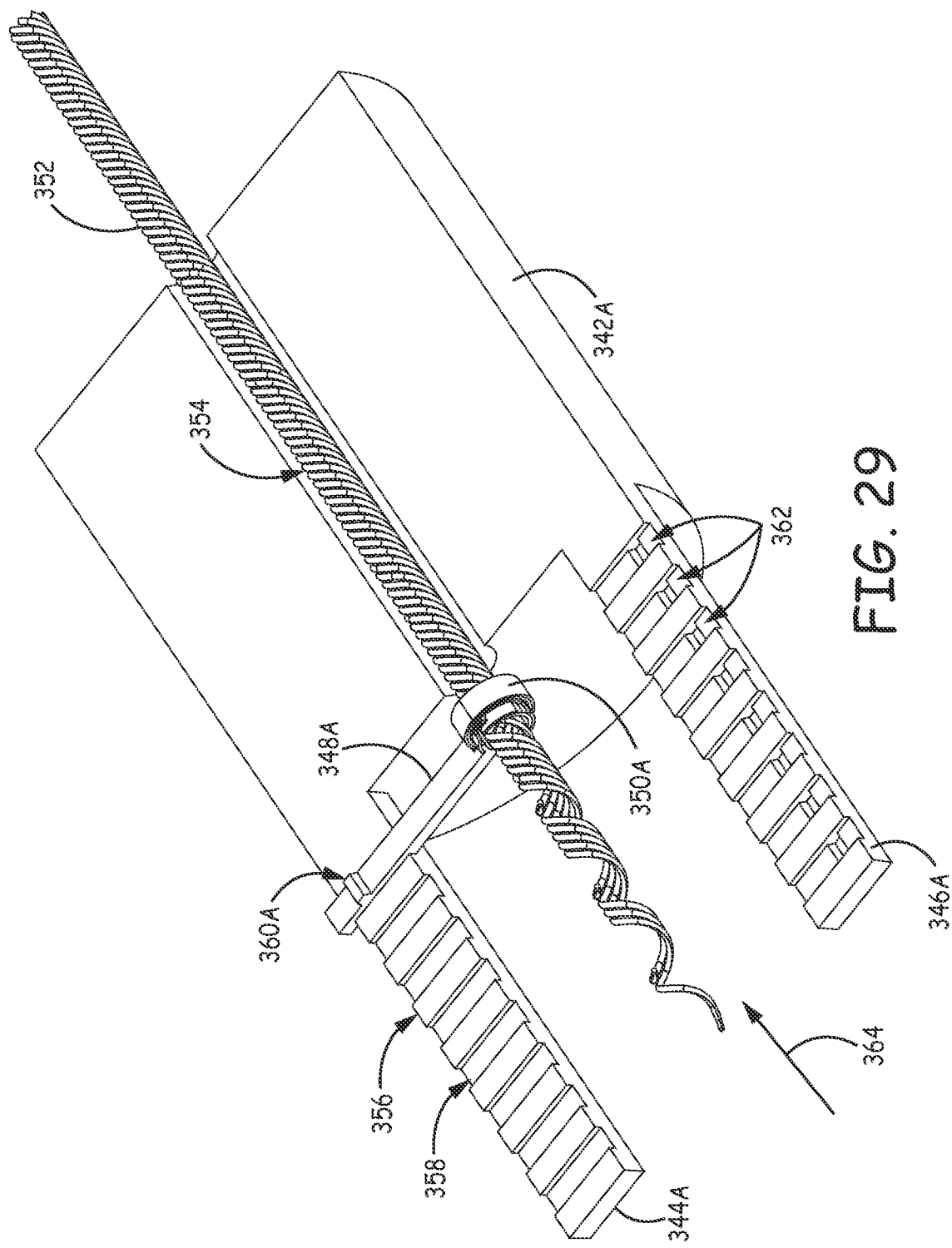
FIGS. 29 and 30 are perspective views of an example support structure and added electrode fixtures to form the example system of FIG. 28.
Figure 30:
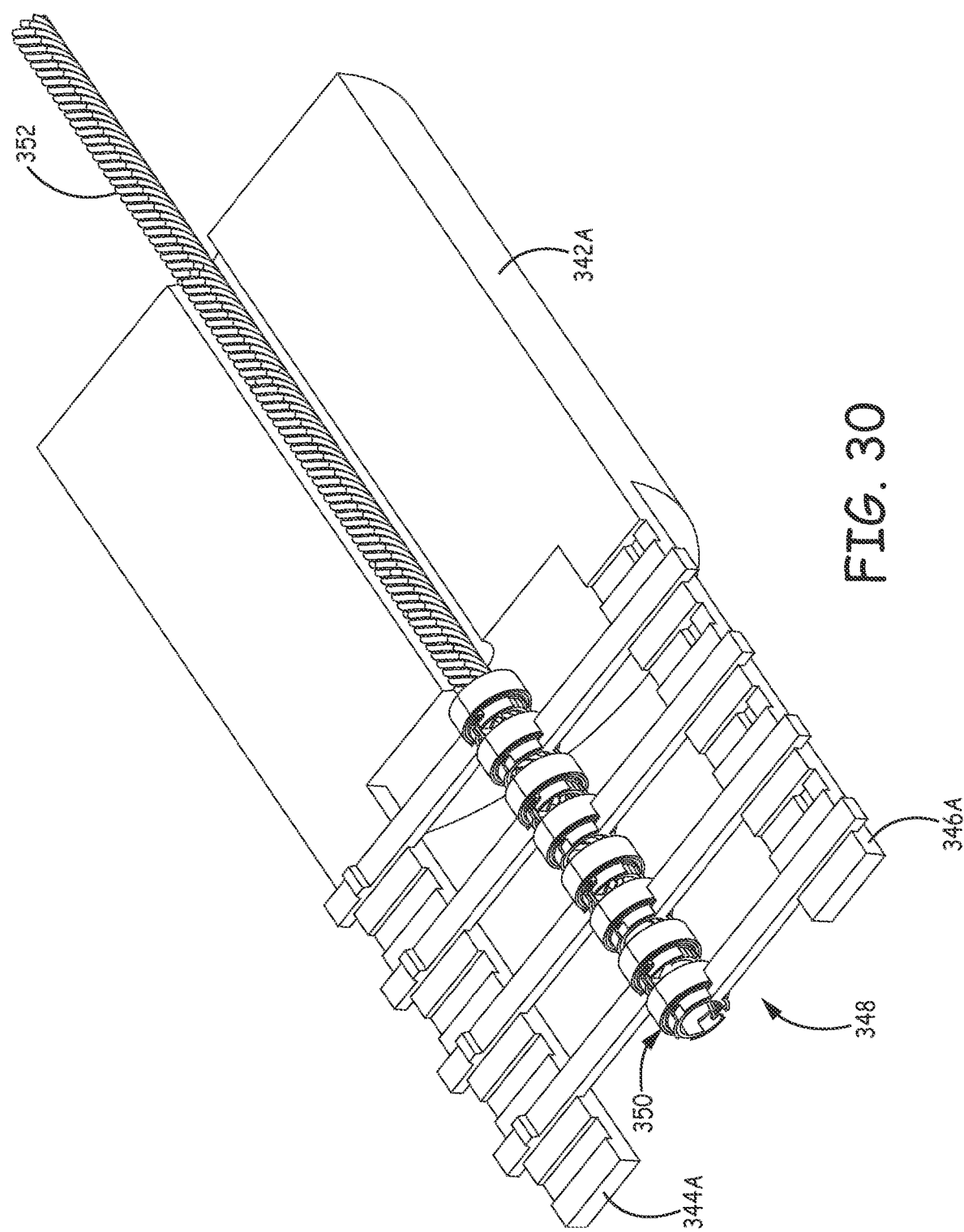

FIGS. 29 and 30 are perspective views of example support structure 342A and added electrode fixtures 348 to form the example system 340 of FIG. 28. As shown in FIG. 29, the interior surfaces of support structure 342A may be exposed when support structure 342A is not mated with support structure 342B. Support structure 342A defines channel 354 that is configured to accept conductors 352. Conductors 352 may be coiled in some examples and uncoiled (e.g., straight) in other examples. Electrode fixtures 348, each fitted within a channel defined by a respective electrode assembly 350, may then be positioned around one or more of conductors 352.

The first electrode fixture to be positioned with respect to support structure 342A is shown as electrode fixture 348A and may be moved over conductors 352 in the direction of arrow 364. Registration arms 344A and 346A each comprise a plurality of channels 358 defined by adjacent raised structures 356. The elongated member of electrode fixture 348A is positioned within one of channels 358. The elongated member may also define a registration structure 360A configured to mate with a slot 362 defined by the respective registration arm (e.g., registration arm 344B of support structure 342B). In other examples, registration structures such as registration structure 360A may be formed on opposing sides of the elongated member of electrode fixture 348A such that the registration structures are configured to mate, or register, with respective slots formed by each of registration arms 344A and 344B (not shown in FIG. 29. In this manner, channels 358 may define the axial alignment of electrode fixtures 348 to conductors 352 and registration structures 360A may define the radial alignment of electrodes 350 with respect to conductors 352.

As shown in FIG. 30, the remaining electrode fixtures 348 have been positioned within respect to registration arms 344A and 346B of support structure 342A. In this manner, electrodes 350 are axially and circumferentially aligned to the respective conductors 352. Subsequent to each of electrode fixtures 348 being placed to registration arms 344A and 346A, support structure 342B of FIG. 28 may be mated to support structure 342A to fix electrode fixtures 348 in place with respect to conductors 352.

As described herein, support structures 342A, 342B, and electrode fixtures 348 may be constructed of various materials such as polymers, composites, and/or metals or metal alloys. The materials may be selected to facilitate molding of the lead body around conductors 352 and electrode assemblies 350.

FIGS. 31A and 31B are perspective views of an example electrode assembly 350 and a respective electrode fixture 348 of the system 340 of FIG. 28. As shown in FIG. 31A, electrode assembly 350 has not been fitted to electrode fixture 348. Electrode fixture 348 includes collar 372 attached to elongated member 366. Elongated member 366 may be attached to collar 372 via neck portion 370, and elongated member 366 may extend away from collar 372. Elongated member 366 may define registration structure 360 configured to radially position electrode fixture 348 with respect to a registration arm of support structure 342A or 342B. In addition, collar 372 defines conductor slot 368 which is configured to accept a distal end of a conductor for coupling to electrode assembly 350.

Electrode assembly 350 includes electrode attachment area 376 and electrode 374. Attachment area 376 is in electrical communication with electrode 374. Electrode assembly 350 also defines a channel within which collar 372 may contact electrode assembly 350 and retain electrode assembly to electrode fixture 348.

FIG. 31B illustrates collar 372 fitted within the channel of electrode assembly 350. Electrode assembly 350 defines a slot 379 within which neck 370 is positioned. In this manner, the mating of neck 370 within slot 379 may orient electrode assembly 350 circumferentially with respect to collar 372. In addition, attachment area 376 may define conductor slot 378. Conductor slot 378 may be configured to accept a conductor for electrically coupling to electrode assembly 350.

Subsequent to electrical coupling of a conductor with electrode fixture 350 and the molding of a lead body, elongated member 366 may be removed from collar 372. A force may be applied to elongated member 366 such that the elongated member fractures at neck 370. Collar 372 may thus remain within electrode assembly 350 and the formed medical lead. In some examples, collar 372 may be configured to provide electrical insulation between electrode assembly 350 and one or more conductors and/or provide structural support for the electrode assembly of the medical lead.

In alternative examples, collar 372 may be removed from electrode assembly 350 after electrical coupling of a conductor to the electrode assembly. Collar 372 may be formed in a semi-circular shape such that the collar may be removed from under the electrode assembly. The open area of the semi-circular shape of the collar may be allowed to pass by the conductors within the collar such that the entire electrode fixture may be removed from the electrode assembly and medical lead.

FIG. 32 is a perspective view of an example system 380 for fabricating a lead that includes electrode fixtures 392 fitted to circumferentially aligned posts 390 to align respective electrode assemblies 394 about conductors 388 of a lead. System 380 may be similar to system 340 of FIG. 28. For example, electrode fixtures 392 may be substantially similar to electrode fixtures 348 of FIGS. 28-31B and electrode assemblies 394 may be similar to electrode assemblies 350 of FIGS. 28-31B. However, support structure 382 differs from support structures 342A and 342B of FIG. 28.

As shown in FIG. 32, system 380 includes conductors 388 coiled around a lead shaft 386, support structure portion 382, electrode fixtures 392, and electrode assemblies 394. Support structure 382 defines an inner channel 384 configured to accept conductors 388. Support structure 382 also includes a plurality of posts 390 configured to mate with a respective electrode fixture 392. Each of posts 390 are distributed at different circumferential positions around an outer perimeter of a distal surface of support structure 382. Each of posts 390 also extend distally from the distal surface of support structure 382. However, the height (e.g., the distance from the distal surface of support structure 382 to a distal surface of the respective post) of each of posts 390 is different to define the various axial positions of each of electrode fixtures 392 and the respective electrode assembly 394. In this manner, the circumferential position of each of posts 390 defines the circumferential alignment of the respective electrodes 394 to conductors 388 and the height of each of posts 390 defines the axial alignment of the respective electrodes 394.

Figure 35A:
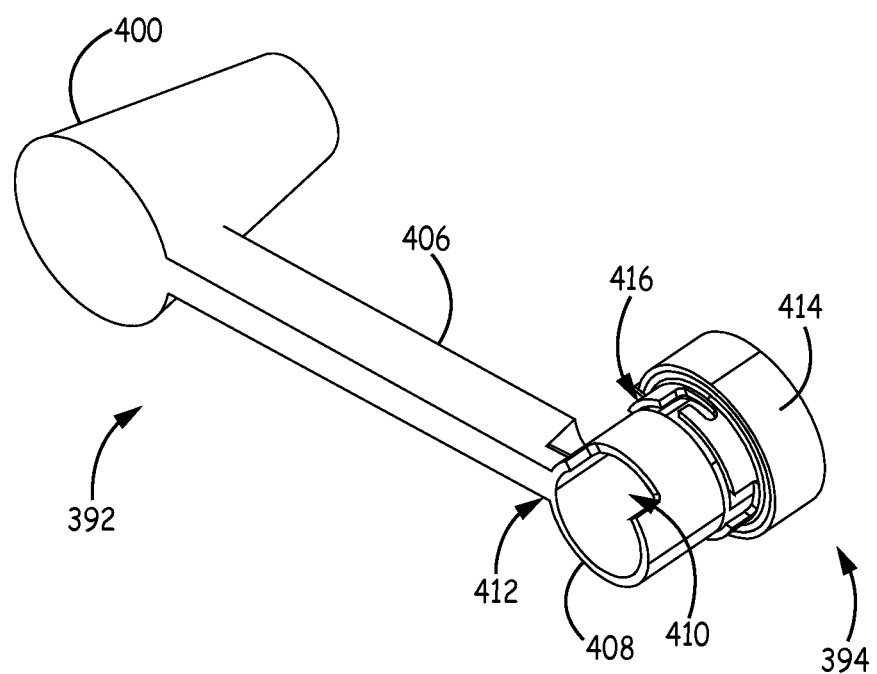
FIGS. 35A and 35B are perspective views of an example electrode and a respective electrode fixture of the system of FIG. 32.
Figure 35B:
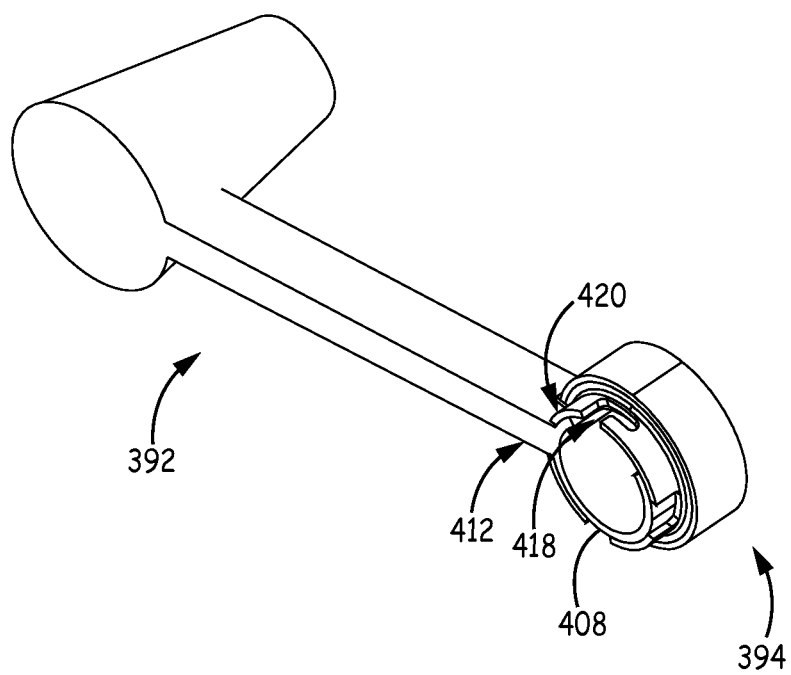

Each of electrode fixtures 392 defines a collar portion connected to an elongated member (e.g., an arm), both of which are illustrated in FIGS. 35A and 35B. At least a portion of the collar portion of each electrode fixture 392 is configured to be fitted within a channel defined by a respective electrode assembly 394. In this manner, the collar portion of each of electrode fixtures 392 may retain a respective electrode assembly 394. Once electrode fixtures 392 are retained within the respective posts 390, electrode assemblies 394 may be axially and circumferentially aligned to respective conductors 388 such that each electrode assembly can be electrically coupled to the respective conductor.

A lead body may be molded around conductors 388 and electrode assemblies 394 to form a medical lead. Subsequent to molding the lead body around the plurality of conductors 388, the elongated member may be removed from the collar such that the collar portion of each electrode fixture 392 remains at least partially fitted within a channel defined by the respective electrode assembly 394. In this manner, the collar portion of electrode fixtures 392 may remain within a completed medical lead.

FIG. 33 is a side view of the example system 380 of FIG. 32. FIG. 33A provides an alternative view 396 of several conductors positioned with respect to electrode assemblies retained by respective electrode fixtures 394. As shown in FIG. 33, posts 390 are constructed with varying heights, or lengths, in the distal direction from the portion of support structure 382 to which each of posts 390 are connected. Each of the posts 390 may thus determine an axial position of a respective electrode fixture 392 and the corresponding electrode fixture 394 with respect to conductors 388. Electrode fixtures 392 may be placed into their respective post 390 in order of increasing distance from support structure 382, e.g., towards the distal end of conductors 388.

The distribution of each of posts 390 around the circumference of support structure 382 may also facilitate access to the distal ends of conductors 388. In other words, a machine or device for electrically coupling conductors 388 to respective electrode assemblies 394 may access the conductor/electrode interface area between adjacent posts 390. As shown in alternative view 396, conductor 388A is shown proximal to respective electrode 394A, conductor 388B is shown proximal to respective electrode 394B, and conductor 388C is shown proximal to respective electrode 394C. In this manner, one or more conductor 388 may be electrically coupled to the respective electrode assembly 394 through a gap formed between adjacent posts 390 of support structure 382. System 380 and/or the electrically coupling mechanism may be rotated to access each of the conductors 388 and the respective electrode assembly 394 for coupling.

Figure 34:
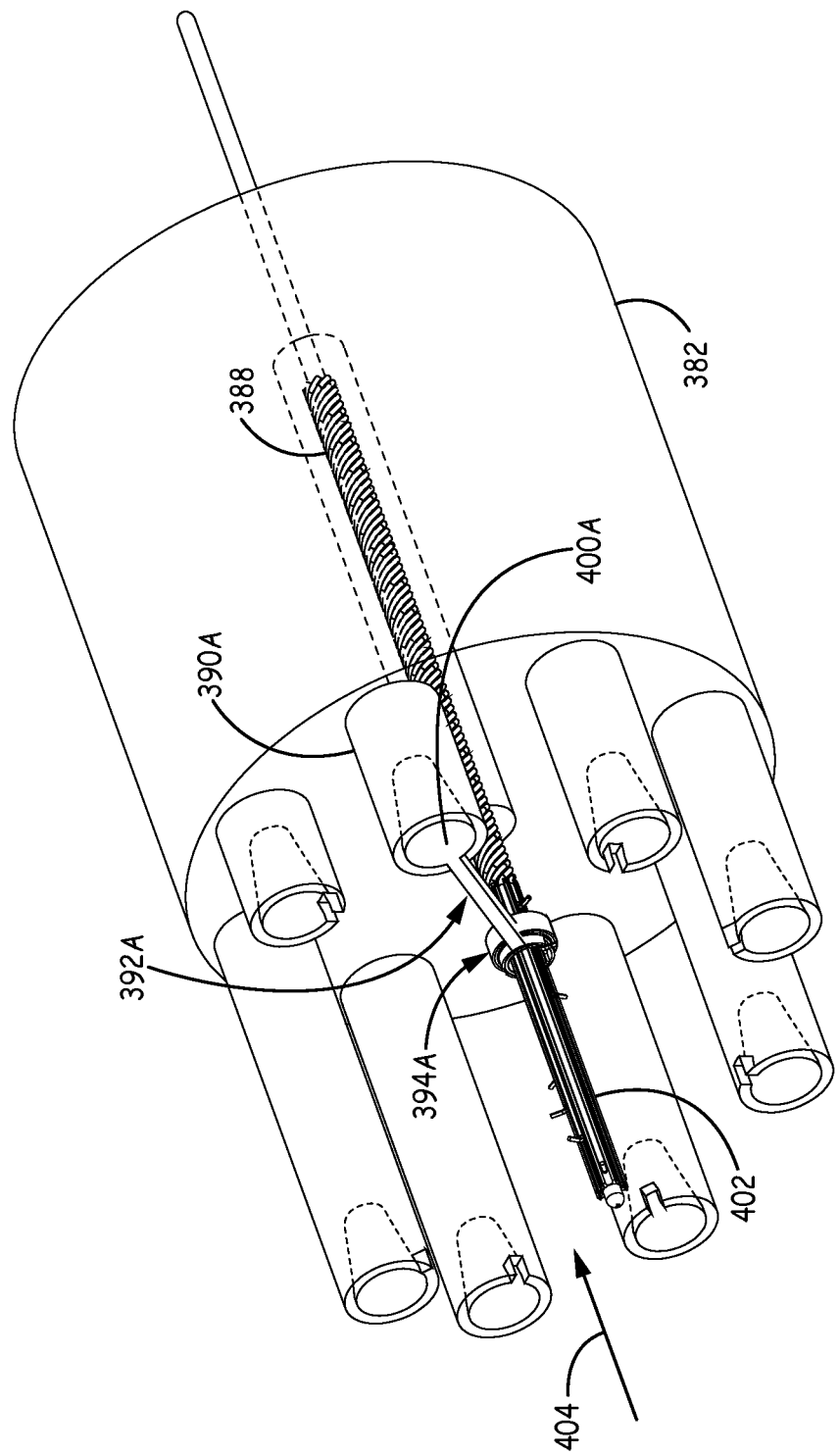
FIG. 34 is a perspective view of an example support structure and an electrode fixture that partially form the example system of FIG. 32.

FIG. 34 is a perspective view of an example support structure 382 and an electrode fixture 392A that partially forms the example system of FIG. 32. As shown in FIG. 34, support structure 382 includes posts 390, such as post 390A, configured to accept respective electrode fixtures 392. For example, post 390A is configured to accept electrode fixture 392A, which includes a collar configured to be fitted within and retain electrode assembly 394A. As the first electrode fixture to be added to system 380, electrode fixture 392A and may be moved over conductors 388 and, in some examples lead structure 402, in the direction of arrow 404.

Electrode fixture 392A may be set to the axial position with respect to conductors 388 via post 390A. Post 390A defines a receptacle 398A configured to accept registration structure 400A of electrode fixture 392A. When registration structure 400A mates within receptacle 398A, electrode fixture 392A may axially and circumferentially align electrode assembly 394A to the respective conductor 388. Additional electrode fixtures 392 and respective electrode assemblies 394 may subsequently to added to the respective posts 390 to form system 380 shown in FIG. 32. Subsequent to one, or all, of electrode fixtures 392 being mated to the respective posts 390 of support structure 382, the distal ends of conductors 388 may be electrically coupled to the respective electrode assemblies 394.

Although receptacle 398A and registration structure 400A may be configured in a cone shape for mating purposes, any other shapes may be employed in other examples. For example, receptacle 398A and registration structure 400A may be formed in the shapes of cubes, rectangular prisms, cylinders, pyramids, or any other regular or irregular shape. Although the registration structure of each of electrode fixtures 392 may be identical, the registration structure of different electrode fixtures 392 may be altered in one or more of size or shape to specify a particular axial position of the respective electrode assembly with respect to conductors 388 and the lead. For example, the receptacle of each post 390 may define a unique shape that corresponds to a unique registration structure of only one of the electrode fixtures 392. In this manner, registration structures and corresponding receptacles may be configured to facilitate a specific arrangement of electrode assemblies within system 380 and the medical lead to be constructed. In other examples, electrode fixtures 392 and posts 390 may include a corresponding pair of unique colors, graphics, or any other visual indications that facilitate appropriate positioning of electrode fixtures 392 and electrodes 394 within system 380.

As described herein, support structure 382 and electrode fixtures 392 may be constructed of various materials such as polymers, composites, and/or metals or metal alloys. The materials may be selected to facilitate molding of the lead body around conductors 388 and electrode assemblies 394.

FIGS. 35A and 35B are perspective views of an example electrode assembly 394 and a respective electrode fixture 392 of system 380 of FIG. 32. As shown in FIG. 35A, electrode assembly 394 has not been fitted to electrode fixture 392. Electrode fixture 392 includes collar 408 attached to elongated member 406. Elongated member 406 may be attached to collar 408 via neck portion 412, and elongated member 406 may extend away from collar 408. Elongated member 406 may define registration structure 400 configured to radially position electrode fixture 392 with respect to a receptacle of a respective post 390 of support structure 382. In addition, collar 408 defines conductor slot 410 which is configured to accept a distal end of a conductor for coupling to electrode assembly 394. Although registration structure 400 is shown as a cone shape, registration structure 400 may be defined as any other shape (e.g., a cylinder, cube, or pyramid) configured to mate with a respective receptacle defined by a post.

Electrode assembly 394 includes electrode attachment area 416 and electrode 414. Attachment area 416 is in electrical communication with electrode 414. Electrode assembly 394 also defines a channel within which collar 408 may contact electrode assembly 394 and retain electrode assembly 394 to electrode fixture 392.

FIG. 35B illustrates collar 408 fitted within the channel of electrode assembly 394. Electrode assembly 394 defines a slot 402 within which neck 412 is positioned. In this manner, the mating of neck 412 within slot 420 may orient electrode assembly 394 circumferentially with respect to collar 408. In addition, attachment area 416 may define conductor slot 418. Conductor slot 418 may be configured to accept a conductor for electrically coupling to electrode assembly 394.

Subsequent to electrical coupling of a conductor with electrode fixture 394 and the molding of a lead body, elongated member 406 may be removed from collar 408. A force may be applied to elongated member 406 such that the elongated member fractures at neck 412. Collar 408 may thus remain within electrode assembly 394 and the formed medical lead. In some examples, collar 408 may be configured to provide electrical insulation between electrode assembly 394 and one or more conductors and/or provide structural support for the electrode assembly of the medical lead.

In alternative examples, collar 408 may be removed from electrode assembly 394 after electrical coupling of a conductor to the electrode assembly. Collar 408 may be formed in a semi-circular shape such that the collar may be removed from under the electrode assembly. The open area of the semi-circular shape of the collar may be allowed to pass by the conductors within the collar such that the entire electrode fixture may be removed from the electrode assembly and medical lead.

As described herein, any of the electrode assemblies may comprise a single electrode or multiple electrodes around the circumference of the electrode assembly. For example, electrode assemblies 150 and 170 are shown having three electrodes each, but electrode assemblies may instead be configured to include one, two, or more than three electrodes. As another example, electrode assemblies 308, 350, and 394 are shown as having a single electrode. However, electrode assemblies 308, 350, and 394 may be configured to include two or more electrodes disposed around the circumference of the electrode assembly. Each of the example systems 132, 190, 232, 240, 300, 340, and 380 may be configured to axially and/or circumferentially align electrode assemblies with respect to other electrode assemblies of the respective system and/or to the location of respective conductors to which the electrode assemblies will be electrically coupled. Systems 132, 190, 232, 240, 300, 340, and 380 are provides as just some examples of such configurations.

The relative terms proximal and distal are used throughout this disclosure to describe the relationship between various structures. Proximal is generally used to describe a direction towards an end of the lead configured to couple to an IMD. In contrast, distal is general used to describe a direction towards an end of the lead that terminates within tissue of the patient and may include one or more electrodes. These relative terms may also be applied to structures used to fabricate the lead, and the relative terms apply as the structures would be disposed when fabricating the lead.

In one example, a method may include positioning an electrode fixture at least partially around at least one conductor of a plurality of conductors for a medical lead, wherein the electrode fixture at least partially retains an electrode assembly, and when the electrode assembly is at least partially retained by the electrode fixture, electrically coupling a portion of the at least one conductor with at least a portion of the electrode assembly at an attachment area defined by the electrode assembly. The portion of the at least one conductor may include a distal end of the at least one conductor, and the method may include placing the distal end of the at least one conductor into the attachment area defined by the electrode assembly.

The electrode assembly may be a first electrode assembly, the electrode fixture may be a first electrode fixture, the at least one conductor of the plurality of conductors may be a first conductor, and the attachment area may be a first attachment area, such that the method may further include positioning a second electrode fixture at least partially around a second conductor of the plurality of conductors such that the second electrode fixture is circumferentially aligned with the first electrode fixture. The second electrode fixture may at least partially retain a second electrode assembly. The second electrode assembly may be at least partially retained by the second electrode fixture, electrically coupling a portion of the second conductor with at least a portion of the second electrode assembly at a second attachment area defined by the second electrode assembly.

A method may also include positioning both the first electrode fixture and the second electrode fixture around the respective conductors prior to coupling the portion of the first conductor with the portion of the first electrode assembly and coupling the portion of the second conductor with the portion of the second electrode assembly. A method may include registering a distal surface of the first electrode fixture to a proximal surface of the second electrode to fix an axial distance between the first electrode assembly and the second electrode assembly and a circumferential position between the first electrode assembly and the second electrode assembly, wherein the distal surface contacts the proximal surface. The method may also include contacting a distal surface of the first electrode fixture to a first surface of a spacer, wherein the distal surface contacts the first surface, contacting a proximal surface of the second electrode fixture to a second surface of the spacer to fix an axial distance between the first electrode assembly and the second electrode assembly, wherein the proximal surface contacts the second surface, registering a first registration structure of the first electrode fixture to a registration bar to fix a circumferential position between the first electrode assembly and the second electrode assembly, and registering a second registration structure of the second electrode fixture to the registration bar.

An electrode fixture may include a collar at least partially fitted within a channel defined by the electrode assembly, wherein the electrode fixture comprises an elongated member extending radially outward from a portion of the collar and beyond the electrode assembly. The electrode fixture may retain the electrode assembly at least partially within a channel defined by the electrode fixture. A method may also include fixing a shaft of an orientation tool to the electrode assembly, and inserting the electrode assembly in the channel of the electrode fixture, wherein the electrode fixture is configured to retain the electrode assembly. The method may also include removing the shaft of the orientation tool from the electrode assembly, removing a distal portion of the electrode assembly from a central portion of the electrode assembly positioned within the electrode fixture, and removing a proximal portion of the electrode assembly from the central portion of the electrode assembly positioned within the electrode fixture. Positioning the electrode fixture around the at least one conductor may further include circumferentially orienting the electrode fixture and the electrode assembly to the at least one connector. The electrode assembly may include two or more electrodes disposed circumferentially around the electrode assembly.

A method may include molding a lead body around a plurality of conductors to form at least a portion of a medical lead. The method may also include, subsequent to molding the lead body around the plurality of conductors, removing the electrode fixture from the electrode assembly and the lead body. Removing the electrode fixture from the electrode assembly may include fracturing the electrode fixture in at least one location by applying circumferential forces to the electrode fixture in substantially opposing directions. In some examples, the electrode fixture may include a collar at least partially fitted within a channel defined by the electrode assembly and an elongated member extending radially outward from a portion of the collar, wherein a method includes, subsequent to molding the lead body around the plurality of conductors, removing the elongated member from the collar that remains at least partially fitted within the channel defined by the electrode assembly.

In another example, a system may include an electrode assembly that defines an attachment area configured to be electrically coupled to a conductor of a plurality of conductors for a medical lead, and an electrode fixture configured to at least partially retain an electrode assembly, wherein the electrode fixture is further configured to be positioned around at least the conductor of the plurality of conductors, and when the electrode assembly is at least partially retained by the electrode fixture, the electrode fixture is configured to facilitate access for electrical coupling of a portion of the conductor of the plurality of conductors to the attachment area of the electrode assembly.

The electrode assembly may be a first electrode assembly, the electrode fixture may be a first electrode fixture, the one conductor of the plurality of conductors may be a first conductor, and the attachment area may be a first attachment area. The system may also include a second electrode assembly that defines a second attachment area configured to be electrically coupled to a second conductor of the plurality of conductors and an second electrode fixture configured to at least partially retain the second electrode assembly, wherein the second electrode fixture is further configured to be positioned around at least the second conductor, and, when the second electrode assembly is at least partially retained by the second electrode fixture, the second electrode fixture is configured to facilitate access for electrical coupling of a portion of the second conductor of the plurality of conductors to the attachment area of the electrode assembly.

In some examples, the first electrode fixture comprises a distal surface, the second electrode fixture comprises a proximal surface, the first and second electrode fixtures are each configured to register the first electrode assembly to the second electrode assembly when the distal surface contacts the proximal surface, and the registration of the distal surface to the proximal surface fixes an axial distance between the first electrode assembly and the second electrode assembly and a circumferential position between the first electrode assembly and the second electrode assembly. The first electrode fixture may define a first cut-out portion, the second electrode fixture may define a second cut-out portion, and the registration of the distal surface of the first electrode fixture to the proximal surface of second electrode surface aligns the first cut-out portion to the second cut-out portion to define at least a portion of a port through which access to at least the first electrode assembly is achieved.

A system may include a spacer that includes a first surface and a second surface, wherein the first electrode fixture comprises a distal surface configured to register against the first surface of the spacer, and the second electrode fixture comprises a proximal surface configured to register against the second surface of the spacer, wherein the registration against the spacer fixes an axial distance between the first electrode assembly and the second electrode assembly and a circumferential position between the first electrode assembly and the second electrode assembly. The electrode fixture may include a collar at least partially fitted within a channel defined by the electrode assembly and an elongated member extending radially outward from a portion of the collar. The electrode fixture may define a channel, and wherein the electrode fixture is configured to at least partially retain the electrode assembly within the channel.

A system may include an orientation tool that includes a handle and a shaft, wherein the shaft is configured to be fixed to the electrode assembly and the handle is configured to insert and align the electrode assembly in the channel of the electrode fixture. The shaft of the orientation tool may be configured to be removed from the electrode assembly, the electrode assembly comprises a proximal portion, a central portion, and a distal portion, and the proximal portion and the distal portion are both configured to be removed from the central portion when the central portion is positioned within the electrode fixture.

An electrode assembly may include two or more electrodes disposed circumferentially around the electrode assembly, wherein respective positions of the two or more electrodes are fixed with respect to each other within the electrode assembly. An electrode fixture may include an electrode capture portion comprising an inner surface that defines a channel, wherein the electrode capture portion is configured to at least partially retain the electrode assembly against the inner surface of the channel, a collar coupled to the electrode capture portion and configured to contact another electrode fixture, and at least one connection member disposed between the electrode capture portion and the collar such that the electrode capture portion and the collar are disposed at opposing ends of the electrode fixture.

A system, or medical lead, may include a molded lead body that at least partially surrounds the lead structure and the plurality of conductors. The electrode fixture may be configured to be removed from the electrode assembly subsequent to the molded lead body being formed. The system may also include at least one fixture removal tool configured to contact a first removal surface and a second removal surface of the electrode fixture, wherein the at least one fixture removal tool is configured to apply a circumferential force in a first direction to the first removal surface and a circumferential force in a second direction to the second removal surface until the electrode fixture is fractured for removal from the electrode assembly, the first direction being substantially opposite the second direction. In some examples, the electrode fixture may include a collar and an elongated assembly extending radially outward from a portion of the collar, and, subsequent to the molded lead body being formed, the elongated member may be configured to be removed from the collar and the collar is configured to remain within at least a portion of the electrode assembly.

In another example, an assembly for fabricating a medical lead may include, an electrode fixture including an electrode capture portion comprising an inner surface that defines a channel, wherein the electrode capture portion is configured to at least partially retain an electrode assembly against the inner surface of the channel, a proximal surface configured to contact a first structure, a distal surface configured to contact a second structure, and a registration structure configured to circumferentially align the electrode fixture to at least one conductor of a medical lead. The electrode fixture may include a collar mechanically coupled to the electrode capture portion and comprising the proximal surface, wherein the collar is configured to contact another electrode fixture via the proximal surface, and at least one connection member disposed between the electrode capture portion and the collar such that the electrode capture portion and the collar are disposed at opposing ends of the electrode fixture, wherein the electrode capture portion comprises the distal surface.

In some examples, the electrode capture portion may include the registration structure on a circumferential surface of the electrode capture portion, wherein the electrode capture portion comprises a pair of substantially opposing surfaces (e.g., opposing or nearly opposing surfaces) within the electrode capture portion that at least partially define the registration structure. The collar may include the registration structure on a circumferential surface of the collar, wherein the collar also includes a pair of substantially opposing surfaces within the collar that at least partially define the registration structure. In some examples, the electrode fixture may be a first electrode fixture, the electrode assembly may be a first electrode assembly, the first structure may include a second electrode fixture configured to retain a second electrode assembly, the second structure may include a third electrode fixture configured to retain a third electrode assembly, and the registration structure is configured to circumferentially align the first electrode fixture to respective registration structures of the second and third electrode fixtures.

In some examples, the assembly may include a first structure, a second structure, a second electrode fixture, and a third electrode fixture, wherein the first structure comprises a first spacer configured to axially align the electrode fixture to a second electrode fixture and the second structure comprises a second spacer configured to axially align the electrode fixture to a third electrode fixture. The assembly may include a first removal surface disposed at a first circumferential location of the electrode fixture and a second removal surface disposed at a second circumferential location of the electrode fixture, wherein the first removal surface substantially opposes the second removal surface and the first removal surface and the second removal surface are configured to receive substantially opposing circumferential forces that fracture the fixture and facilitate removal of the electrode fixture from the electrode assembly.

In additional examples, a system may include means for at least partially retaining an electrode assembly, wherein the means for at least partially retaining the electrode assembly is configured to be positioned at least partially around at least one conductor of a plurality of conductors for a medical lead, and means for, when the means for at least partially retaining the electrode assembly at least partially retains the electrode assembly, electrically coupling a portion of the at least one conductor with at least a portion of the electrode assembly at an attachment area defined by the electrode assembly.

What is claimed is:

1. A method comprising:
positioning an electrode fixture at least partially around at least one conductor of a plurality of conductors for a medical lead, wherein the electrode fixture defines a radially inward facing surface and the radially inward facing surface defines a channel through the electrode fixture, wherein the channel defines a center axis, and wherein the radially inward facing surface retains at least a first portion of an electrode assembly within the channel and radially inward of the radially inward facing surface of the electrode fixture;
while the at least a first portion of the electrode assembly is retained within the channel by the electrode fixture and the electrode fixture is disposed completely around the center axis of the channel, attaching a portion of the at least one conductor with at least a second portion of the electrode assembly at an attachment area defined by the electrode assembly to electrically couple the portion of the at least one conductor to the second portion of the electrode assembly; and
removing the electrode fixture from the electrode assembly after attaching the portion of the at least one conductor with the second portion of the electrode assembly.

2. The method of claim 1, wherein the portion of the at least one conductor comprises a distal end of the at least one conductor, and wherein the method further comprises placing the distal end of the at least one conductor into the attachment area defined by the electrode assembly.

3. The method of claim 1, wherein the electrode assembly is a first electrode assembly, the electrode fixture is a first electrode fixture, the at least one conductor of the plurality of conductors is a first conductor, the channel is a first channel, the center axis is a first center axis, and the attachment area is a first attachment area, the method further comprising:
positioning a second electrode fixture at least partially around a second conductor of the plurality of conductors such that the second electrode fixture is circumferentially aligned with the first electrode fixture, wherein the second electrode fixture defines a radially inward facing surface of the second electrode fixture and the radially inward facing surface of the second electrode fixture defines a second channel through the second electrode fixture, wherein the second channel defines a second center axis and wherein the radially inward facing surface of the second electrode fixture retains at least a first portion of a second electrode assembly within the second channel and radially inward of the radially inward facing surface of the second electrode fixture; and
while the at least a first portion of the second electrode assembly is retained within the second channel by the second electrode fixture and the second electrode fixture is disposed completely around the second center axis, attaching a portion of the second conductor with at least a second portion of the second electrode assembly at a second attachment area defined by the second electrode assembly to electrically couple the portion of the second conductor to the second portion of the second electrode assembly.

4. The method of claim 3, further comprising positioning both the first electrode fixture and the second electrode fixture around the respective conductors prior to coupling the portion of the first conductor with the portion of the first electrode assembly and coupling the portion of the second conductor with the portion of the second electrode assembly.

5. The method of claim 3, further comprising registering a distal surface of the first electrode fixture to a proximal surface of the second electrode fixture to fix an axial distance between the first electrode assembly and the second electrode assembly and a circumferential position between the first electrode assembly and the second electrode assembly, wherein the distal surface contacts the proximal surface.

6. The method of claim 3, further comprising:
contacting a distal surface of the first electrode fixture to a first surface of a spacer, wherein the distal surface contacts the first surface;
contacting a proximal surface of the second electrode fixture to a second surface of the spacer to fix an axial distance between the first electrode assembly and the second electrode assembly, wherein the proximal surface contacts the second surface;
registering a first registration structure of the first electrode fixture to a registration bar to fix a circumferential position between the first electrode assembly and the second electrode assembly; and
registering a second registration structure of the second electrode fixture to the registration bar.

7. The method of claim 1, wherein the electrode fixture comprises a collar at least partially fitted within a channel defined by the electrode assembly, and wherein the electrode fixture comprises an elongated member extending radially outward from a portion of the collar and beyond the electrode assembly.

8. The method of claim 1, further comprising:
fixing a shaft of an orientation tool to the electrode assembly; and
inserting the electrode assembly in the channel of the electrode fixture, wherein the electrode fixture is configured to retain the electrode assembly.

9. The method of claim 8, further comprising:
removing the shaft of the orientation tool from the electrode assembly;
removing a distal portion of the electrode assembly from a central portion of the electrode assembly positioned within the electrode fixture; and
removing a proximal portion of the electrode assembly from the central portion of the electrode assembly positioned within the electrode fixture.

10. The method of claim 1, wherein positioning the electrode fixture around the at least one conductor further comprises circumferentially orienting the electrode fixture and the electrode assembly to the at least one connector.

11. The method of claim 1, wherein the electrode assembly comprises two or more electrodes disposed circumferentially around the electrode assembly.

12. The method of claim 1, further comprising molding a lead body around the plurality of conductors to form at least a portion of the medical lead.

13. The method of claim 12, wherein removing the electrode fixture from the electrode assembly comprises, subsequent to molding the lead body around the plurality of conductors, removing the electrode fixture from the electrode assembly and the lead body, wherein removing the electrode fixture comprises fracturing the electrode fixture at at least one location of the electrode fixture.

14. The method of claim 13, wherein removing the electrode fixture from the electrode assembly comprises applying circumferential forces in substantially opposing directions to the at least one location in order to fracture the electrode fixture at the at least one location.

15. The method of claim 14, wherein applying the circumferential forces in substantially opposing directions comprises:
applying a first force against a first removal surface defined by the electrode fixture and disposed at a first circumferential location of the electrode fixture; and
applying a second force against a second removal surface defined by the electrode fixture and disposed at a second circumferential location of the electrode fixture, wherein the first removal surface substantially opposes the second removal surface.

16. A system comprising:
an electrode fixture defining a radially inward facing surface that defines a channel through the electrode fixture and is configured to retain at least a portion of an electrode assembly within the channel and radially inward of the radially inward facing surface of the electrode fixture, wherein the channel defines a center axis, and wherein:
the electrode assembly defines an attachment area configured to be electrically coupled to a conductor of a plurality of conductors for a medical lead,
the electrode fixture is configured to be positioned around at least the conductor of the plurality of conductors,
the electrode fixture is configured to facilitate access for attaching a portion of the conductor of the plurality of conductors to the attachment area of the electrode assembly to electrically couple the portion of the conductor to the electrode assembly while the at least a portion of the electrode assembly is retained within the channel by the electrode fixture and the electrode fixture is disposed completely around the center axis of the channel; and
the electrode fixture is configured to be removed from the electrode assembly after the portion of the conductor is attached to the attachment area of the electrode assembly.

17. The system of claim 16, wherein the electrode fixture is a first electrode fixture and the electrode assembly is a first electrode assembly, the conductor is a first conductor, the channel is a first channel, the center axis is a first center axis, and the attachment area is a first attachment area, and wherein the system further comprises:
a second electrode fixture defining a radially inward facing surface of the second electrode fixture that defines a channel through the second electrode fixture and is configured to retain at least a portion of a second electrode assembly within the second channel and radially inward of the radially inward facing surface of the second electrode fixture, wherein the second channel defines a second center axis, wherein:
the second electrode assembly defines a second attachment area configured to be electrically coupled to a second conductor of the plurality of conductors for the medical lead,
the second electrode fixture is configured to be positioned around at least the first conductor and the second conductor of the plurality of conductors, and
the second electrode fixture is configured to facilitate access for attaching a portion of the second conductor of the plurality of conductors to the second attachment area of the second electrode assembly to electrically couple the portion of the second conductor to the second electrode assembly while the at least a portion of the second electrode assembly is retained within the second channel by the second electrode fixture and the second electrode fixture is disposed completely around the second center axis of the second channel.

18. The system of claim 17, wherein:
the first electrode fixture comprises a first proximal surface and a first distal surface;
the second electrode fixture comprises a second proximal surface and a second distal surface;
the first proximal surface of the first electrode fixture is configured to contact and register with the second distal surface of the second electrode fixture to fix an axial distance between the first electrode assembly and the second electrode assembly and a circumferential position between the first electrode assembly and the second electrode assembly.

19. The system of claim 17, further comprising:
a spacer defining a third proximal surface and a third distal surface; and
a registration bar, wherein:
the first electrode fixture comprises a first proximal surface, a first distal surface, and a first registration structure;
the second electrode fixture comprises a second proximal surface, a second distal surface, and a second registration structure;
the first proximal surface of the first electrode fixture is configured to contact the third distal surface of the spacer and the second distal surface of the second electrode fixture is configured to contact the third proximal surface of the spacer to fix an axial distance between the first electrode assembly and the second electrode assembly;
the first registration structure of the first electrode fixture is configured to register with the registration bar and the second registration structure of the second electrode fixture is configured to register with the registration bar to fix a circumferential orientation between the first electrode assembly and the second electrode assembly.

20. A system comprising:
means for retaining at least a portion of an electrode assembly within a channel and radially inward of the means for retaining the portion of the electrode assembly, wherein the channel defines a center axis, and wherein:
the electrode assembly defines an attachment area configured to be electrically coupled to a conductor of a plurality of conductors for a medical lead,
the means for retaining the at least a portion of the electrode assembly is configured to be positioned around at least the conductor of the plurality of conductors,
the means for retaining the at least a portion of the electrode assembly is configured to facilitate access for electrical coupling of a portion of the conductor of the plurality of conductors to the attachment area of the electrode assembly while the at least a portion of the electrode assembly is retained within the channel by the means for retaining the at least a portion of the electrode assembly and the means for retaining the at least a portion of the electrode assembly is disposed completely around the center axis of the channel, and the means for retaining the at least a portion of the electrode assembly is configured to be removed from the electrode assembly after the portion of the conductor is electrically coupled to the attachment area of the electrode assembly.

\* \* \* \* \*